US012685474B2

(12) United States Patent
Welsh et al.

(10) Patent No.: US 12,685,474 B2
(45) Date of Patent: Jul. 21, 2026

(54) CARDIAC MAPPING SYSTEM WITH EFFICIENCY ALGORITHM

(71) Applicant: ENCHANNEL MEDICAL, LTD., Irvine, CA (US)

(72) Inventors: Daniel Welsh, Encinitas, CA (US); Derrick Ren-yu Chou, San Diego, CA (US); Haizhe Zhang, San Diego, CA (US); Leo Mariappan, Oceanside, CA (US); Min Zhu, San Marcos, CA (US); Steven Anthony Yon, San Diego, CA (US); Xinwei Shi, San Diego, CA (US); Graydon Ernest Beatty, Carlsbad, CA (US); Nathan Angel, Oceanside, CA (US); Weiyi Tang, San Diego, CA (US); Christoph Scharf, Horgen (CH); Christopher J. Flaherty, Auburndale, FL (US); Ahmad Falahatpisheh, San Marcos, CA (US)

(73) Assignee: ENCHANNEL MEDICAL, LTD., Irvine, CA (US)

( * ) Notice: Subject to any disclaimer, the term of this patent is extended or adjusted under 35 U.S.C. 154(b) by 265 days.

(21) Appl. No.: 17/858,174

(22) Filed: Jul. 6, 2022

(65) Prior Publication Data

US 2024/0050009 A1 Feb. 15, 2024

Related U.S. Application Data

(63) Continuation of application No. 16/097,959, filed as application No. PCT/US2017/030922 on May 3, 2017, now Pat. No. 11,399,759.

(Continued)

(51) Int. Cl.
*A61B 5/339* (2021.01)
*A61B 5/05* (2021.01)
(Continued)

(52) U.S. Cl.
CPC ................ *A61B 5/339* (2021.01); *A61B 5/05* (2013.01); *A61B 5/107* (2013.01); *A61B 5/283* (2021.01);
(Continued)

(58) Field of Classification Search
CPC ........... A61B 5/25; A61B 5/296; A61B 5/318; A61B 5/339; A61B 5/291; A61B 5/30;
(Continued)

(56) References Cited

U.S. PATENT DOCUMENTS 5,041,973 A 8/1991 Lebron et al.
5,156,151 A 10/1992 Imran
(Continued)

FOREIGN PATENT DOCUMENTS

CA 2829626 9/2012
CN 1981710 6/2007
(Continued)

OTHER PUBLICATIONS

Japanese Office Action dated Aug. 23, 2022 issued in corresponding Japanese Application No. 2018-557371, with machine translation to English.

(Continued)

*Primary Examiner* — Michael J Lau
(74) *Attorney, Agent, or Firm* — Onello & Mello P.C.

(57) ABSTRACT

A cardiac information dynamic display system comprises: one or more electrodes configured to record sets of electric potential data representing cardiac activity at a plurality of time intervals; and a cardiac information console, comprising: a signal processor configured to: calculate sets of cardiac activity data at the plurality of time intervals using the recorded sets of electric potential data, wherein the cardiac activity data is associated with surface locations of one or more cardiac chambers; and a user interface module (Continued)

configured to display a series of images, each image comprising: a graphical representation of the cardiac activity. Methods of providing cardiac activity data are also provided.

18 Claims, 26 Drawing Sheets

Related U.S. Application Data

(60) Provisional application No. 62/413,104, filed on Oct. 26, 2016, provisional application No. 62/331,364, filed on May 3, 2016.

(51) Int. Cl.

| | |
|---|---|
| *A61B 5/107* | (2006.01) |
| *A61B 5/283* | (2021.01) |
| *A61B 5/296* | (2021.01) |
| *A61B 5/305* | (2021.01) |
| *A61B 5/308* | (2021.01) |
| *A61B 5/33* | (2021.01) |
| *A61B 8/00* | (2006.01) |
| *A61B 8/08* | (2006.01) |
| *A61B 8/12* | (2006.01) |
| *A61B 18/14* | (2006.01) |
| *A61B 34/20* | (2016.01) |
| *A61B 5/00* | (2006.01) |
| *A61B 5/361* | (2021.01) |
| *A61B 17/00* | (2006.01) |
| *A61B 18/00* | (2006.01) |
| *A61B 34/10* | (2016.01) |

(52) U.S. Cl.
CPC .............. *A61B 5/296* (2021.01); *A61B 5/305* (2021.01); *A61B 5/308* (2021.01); *A61B 5/33* (2021.01); *A61B 8/0883* (2013.01); *A61B 8/12* (2013.01); *A61B 8/4416* (2013.01); *A61B 8/4477* (2013.01); *A61B 18/14* (2013.01); *A61B 34/20* (2016.02); *A61B 5/361* (2021.01); *A61B 5/6858* (2013.01); *A61B 2017/00106* (2013.01); *A61B 2018/00267* (2013.01); *A61B 2018/00351* (2013.01); *A61B 2018/00839* (2013.01); *A61B 2034/105* (2016.02)

(58) Field of Classification Search
CPC ........... A61B 5/283; A61B 5/05; A61B 5/107; A61B 5/361; A61B 34/20; A61B 8/0883; A61B 8/12; A61B 8/4416; A61B 8/4477; A61B 8/14; A61B 2034/105; A61B 2017/00106; A61B 2018/00267; A61B 2018/00351; A61B 2018/00839
See application file for complete search history.

(56) References Cited

U.S. PATENT DOCUMENTS

| | | | |
|---|---|---|---|
| 5,482,472 | A | 1/1996 | Garoni et al. |
| 5,499,981 | A | 3/1996 | Kordis |
| 5,555,883 | A | 9/1996 | Avitall |
| 5,595,183 | A | 1/1997 | Swanson et al. |
| 5,601,084 | A | 2/1997 | Sheehan et al. |
| 5,622,174 | A | 4/1997 | Yamazaki |
| 5,647,367 | A | 7/1997 | Lum et al. |
| 5,662,108 | A | 9/1997 | Budd et al. |
| 5,687,737 | A | 11/1997 | Branham et al. |
| 5,722,402 | A | 3/1998 | Swanson et al. |
| 5,722,416 | A | 3/1998 | Swanson et al. |
| 5,740,808 | A | 4/1998 | Panescu et al. |
| 5,749,833 | A | 5/1998 | Hakki et al. |
| 5,759,158 | A | 6/1998 | Swanson |
| 5,795,298 | A | 8/1998 | Vesley et al. |
| 5,795,299 | A | 8/1998 | Eaton et al. |
| 5,820,568 | A | 10/1998 | Willis |
| 5,871,019 | A | 2/1999 | Belohlavek |
| 5,876,336 | A | 3/1999 | Swanson et al. |
| 5,928,228 | A | 7/1999 | Kordis et al. |
| 5,968,040 | A | 10/1999 | Swanson et al. |
| 6,014,582 | A | 1/2000 | He |
| 6,014,590 | A | 1/2000 | Whayne et al. |
| 6,024,703 | A | 2/2000 | Zanelli et al. |
| 6,066,096 | A | 5/2000 | Smith et al. |
| 6,086,532 | A | 7/2000 | Panescu et al. |
| 6,107,699 | A | 8/2000 | Swanson |
| 6,187,032 | B1 | 2/2001 | Ohyu et al. |
| 6,188,928 | B1 | 2/2001 | Noren et al. |
| 6,216,027 | B1 | 4/2001 | Willis et al. |
| 6,216,043 | B1 | 4/2001 | Swanson et al. |
| 6,223,072 | B1 * | 4/2001 | Mika ...................... A61B 5/346 |
| | | | 600/510 |
| 6,240,307 | B1 | 5/2001 | Beatty et al. |
| 6,301,496 | B1 | 10/2001 | Reisfeld |
| 6,400,981 | B1 | 6/2002 | Govari |
| 6,490,474 | B1 * | 12/2002 | Willis ................ A61B 18/1492 |
| | | | 606/41 |
| 6,514,249 | B1 | 2/2003 | Maguire et al. |
| 6,574,492 | B1 | 6/2003 | Ben-Haim et al. |
| 6,640,119 | B1 | 10/2003 | Budd et al. |
| 6,716,166 | B2 | 4/2004 | Govari |
| 6,728,562 | B1 | 4/2004 | Budd et al. |
| 6,772,004 | B2 | 8/2004 | Rudy |
| 6,773,402 | B2 | 8/2004 | Govari et al. |
| 6,824,515 | B2 | 11/2004 | Suorsa et al. |
| 6,826,420 | B1 | 11/2004 | Beatty et al. |
| 6,826,421 | B1 | 11/2004 | Beatty et al. |
| 6,839,588 | B1 | 1/2005 | Rudy |
| 6,869,403 | B2 | 3/2005 | Narimatsu et al. |
| 6,895,267 | B2 | 5/2005 | Panescu et al. |
| 6,939,309 | B1 | 9/2005 | Beatty et al. |
| 6,950,689 | B1 | 9/2005 | Willis et al. |
| 6,957,101 | B2 | 10/2005 | Porath et al. |
| 6,970,733 | B2 | 11/2005 | Willis et al. |
| 6,978,168 | B2 | 12/2005 | Beatty et al. |
| 6,990,370 | B1 | 1/2006 | Beatty et al. |
| 7,187,964 | B2 | 3/2007 | Khoury |
| 7,258,674 | B2 | 8/2007 | Hillstead et al. |
| 7,263,397 | B2 | 8/2007 | Hauck et al. |
| 7,285,119 | B2 | 10/2007 | Stewart et al. |
| 7,289,841 | B2 | 10/2007 | Johnson et al. |
| 7,289,843 | B2 | 10/2007 | Beatty et al. |
| 7,291,146 | B2 | 11/2007 | Steinke et al. |
| 7,433,730 | B1 | 10/2008 | Berrier |
| 7,479,141 | B2 | 1/2009 | Kleen et al. |
| 7,505,810 | B2 | 3/2009 | Harlev et al. |
| 7,515,954 | B2 | 4/2009 | Harlev et al. |
| 7,545,903 | B2 | 6/2009 | Koehler et al. |
| 7,573,182 | B2 | 8/2009 | Savage |
| 7,689,261 | B2 | 3/2010 | Mohr et al. |
| 7,729,752 | B2 | 6/2010 | Harlev et al. |
| 7,766,838 | B2 | 8/2010 | Yagi et al. |
| 7,806,825 | B2 | 10/2010 | Heim |
| 7,841,986 | B2 | 11/2010 | He et al. |
| 7,918,793 | B2 | 4/2011 | Altmann et al. |
| 7,953,475 | B2 | 5/2011 | Harlev et al. |
| 8,103,327 | B2 | 1/2012 | Harlev et al. |
| 8,103,338 | B2 | 1/2012 | Harlev et al. |
| 8,147,486 | B2 | 4/2012 | Honour et al. |
| 8,150,499 | B2 | 4/2012 | Gelbart et al. |
| 8,208,998 | B2 | 6/2012 | Beatty et al. |
| 8,346,339 | B2 | 1/2013 | Kordis et al. |
| 8,360,786 | B2 | 1/2013 | Duryea |
| 8,364,234 | B2 | 1/2013 | Kordis et al. |
| 8,388,547 | B2 | 3/2013 | Revishvili et al. |
| 8,401,625 | B2 | 3/2013 | Harlev et al. |
| 8,412,307 | B2 | 4/2013 | Willis et al. |
| 8,417,313 | B2 | 4/2013 | Scharf et al. |
| 8,428,690 | B2 | 4/2013 | Li et al. |
| 8,447,377 | B2 | 5/2013 | Harlev et al. |

(56)			References Cited

U.S. PATENT DOCUMENTS

| | | |
|---|---|---|
| 8,454,596 B2 | 6/2013 | Ma et al. |
| 8,463,368 B2 | 6/2013 | Harlev et al. |
| 8,465,433 B2 | 6/2013 | Zwirn |
| 8,512,255 B2 | 8/2013 | Scharf et al. |
| 8,532,753 B2 | 9/2013 | Makdissi |
| 8,597,193 B2 | 12/2013 | Grunwald et al. |
| 8,700,119 B2 | 4/2014 | Scharf et al. |
| 8,755,861 B2 | 6/2014 | Harlev et al. |
| 8,825,130 B2 | 9/2014 | Just et al. |
| 8,825,134 B2 | 9/2014 | Danehorn |
| 8,852,103 B2 | 10/2014 | Rothberg et al. |
| 8,918,158 B2 | 12/2014 | Scharf et al. |
| 8,934,988 B2 | 1/2015 | Persson et al. |
| 8,948,837 B2 | 2/2015 | Harlev et al. |
| 8,968,299 B2 | 3/2015 | Kauphusman et al. |
| 8,972,228 B2 | 3/2015 | Ghosh et al. |
| 8,979,839 B2 | 3/2015 | De La Rama et al. |
| 8,989,842 B2 | 3/2015 | Li et al. |
| 9,011,423 B2 | 4/2015 | Brewster et al. |
| 9,031,642 B2 | 5/2015 | Ghosh |
| 9,037,259 B2 | 5/2015 | Mathur |
| 9,044,245 B2 | 6/2015 | Condie et al. |
| 9,167,982 B2 | 10/2015 | Scharf et al. |
| 9,186,081 B2 | 11/2015 | Afonso et al. |
| 9,186,212 B2 | 11/2015 | Nabutovsky et al. |
| 9,192,318 B2 | 11/2015 | Scharf et al. |
| 9,241,687 B2 | 1/2016 | Mcgee |
| 9,259,166 B2 | 2/2016 | Rudy et al. |
| 9,351,789 B2 | 5/2016 | Novichenok et al. |
| D758,596 S | 6/2016 | Perryman et al. |
| 9,380,953 B2 | 7/2016 | Houben et al. |
| 9,474,486 B2 | 10/2016 | Eliason et al. |
| 9,480,525 B2 | 11/2016 | Lopes et al. |
| 9,486,355 B2 | 11/2016 | Gustus et al. |
| 9,492,227 B2 | 11/2016 | Lopes et al. |
| 9,492,228 B2 | 11/2016 | Lopes et al. |
| 9,504,395 B2 | 11/2016 | Scharf et al. |
| 9,510,763 B2 | 12/2016 | Ghosh et al. |
| 9,526,573 B2 | 12/2016 | Lopes et al. |
| 9,549,708 B2 | 1/2017 | Mercanzini et al. |
| 9,579,149 B2 | 2/2017 | Kelly et al. |
| D782,626 S | 3/2017 | Werneth et al. |
| D782,686 S | 3/2017 | Werneth et al. |
| 9,585,588 B2 | 3/2017 | Marecki et al. |
| 9,603,651 B2 | 3/2017 | Ghosh |
| 9,610,024 B2 | 4/2017 | Scharf et al. |
| 9,713,730 B2 | 7/2017 | Mathur et al. |
| 9,717,555 B2 | 8/2017 | Chan et al. |
| 9,717,559 B2 | 8/2017 | Ditter et al. |
| 9,757,044 B2 | 9/2017 | Scharf et al. |
| 9,820,666 B2 | 11/2017 | Bokan et al. |
| 9,827,039 B2 | 11/2017 | Dandler et al. |
| 9,913,589 B2 | 3/2018 | Scharf et al. |
| 9,918,652 B2 | 3/2018 | Zeng et al. |
| 9,962,097 B2 | 5/2018 | Ghosh et al. |
| 9,968,268 B2 | 5/2018 | Scharf et al. |
| 9,974,457 B2 | 5/2018 | Ghosh et al. |
| 10,004,459 B2 | 6/2018 | Werneth et al. |
| 10,039,464 B2 | 8/2018 | Dubois et al. |
| 10,049,771 B2 | 8/2018 | Voth et al. |
| 10,201,311 B2 | 2/2019 | Chou et al. |
| D851,774 S | 6/2019 | Werneth et al. |
| 10,321,890 B2 | 6/2019 | Grunwald et al. |
| 10,470,743 B2 | 11/2019 | Grunwald et al. |
| 10,667,753 B2 | 6/2020 | Werneth et al. |
| 10,796,801 B2 * | 10/2020 | Silverman .............. G16H 50/50 |
| 10,888,235 B2 | 1/2021 | Hagfors et al. |
| D954,970 S | 6/2022 | Werneth et al. |
| 11,399,759 B2 * | 8/2022 | Welsh ................... A61B 5/1107 |
| 12,053,258 B2 * | 8/2024 | Welsh ................... A61B 5/004 |
| 12,133,984 B2 | 11/2024 | Ghosh et al. |
| 2001/0007070 A1 | 7/2001 | Stewart et al. |
| 2002/0026118 A1 | 2/2002 | Govari |
| 2002/0128565 A1 | 9/2002 | Rudy |
| 2002/0165441 A1 | 11/2002 | Coleman et al. |
| 2003/0036696 A1 | 2/2003 | Willis et al. |
| 2003/0065271 A1 | 4/2003 | Khoury |
| 2003/0078494 A1 | 4/2003 | Panescu et al. |
| 2003/0153907 A1 | 8/2003 | Suorsa et al. |
| 2003/0158477 A1 | 8/2003 | Panescu |
| 2003/0176799 A1 | 9/2003 | Beatty et al. |
| 2003/0231789 A1 | 12/2003 | Willis et al. |
| 2003/0236465 A1 | 12/2003 | Narimatsu et al. |
| 2003/0236466 A1 | 12/2003 | Tarjan et al. |
| 2004/0039293 A1 * | 2/2004 | Porath .................... A61B 5/064 |
| | | 600/509 |
| 2004/0039312 A1 | 2/2004 | Hillstead et al. |
| 2004/0082846 A1 * | 4/2004 | Johnson ................. A61B 6/032 |
| | | 600/410 |
| 2004/0082948 A1 | 4/2004 | Stewart et al. |
| 2004/0122317 A1 | 6/2004 | Heim |
| 2004/0254437 A1 | 12/2004 | Hauck et al. |
| 2005/0059880 A1 | 3/2005 | Mathias et al. |
| 2005/0096647 A1 * | 5/2005 | Steinke ............. A61B 18/1815 |
| | | 606/41 |
| 2005/0101874 A1 | 5/2005 | Beatty et al. |
| 2005/0113665 A1 | 5/2005 | Mohr et al. |
| 2005/0148836 A1 | 7/2005 | Kleen et al. |
| 2005/0203375 A1 * | 9/2005 | Willis .................... A61B 5/287 |
| | | 600/407 |
| 2006/0052716 A1 | 3/2006 | Beatty et al. |
| 2006/0058663 A1 | 3/2006 | Willis et al. |
| 2006/0058676 A1 | 3/2006 | Yagi et al. |
| 2006/0058692 A1 | 3/2006 | Beatty et al. |
| 2006/0058693 A1 | 3/2006 | Beatty et al. |
| 2006/0084884 A1 | 4/2006 | Beatty et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0116576 A1 | 6/2006 | McGee et al. |
| 2007/0049817 A1 | 3/2007 | Preiss et al. |
| 2007/0053482 A1 | 3/2007 | Koehler et al. |
| 2007/0060832 A1 | 3/2007 | Levin |
| 2007/0083194 A1 | 4/2007 | Kunis et al. |
| 2007/0106146 A1 | 5/2007 | Altmann et al. |
| 2007/0232949 A1 | 10/2007 | Saksena |
| 2007/0244479 A1 | 10/2007 | Beatty et al. |
| 2007/0270703 A1 | 11/2007 | He et al. |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0009758 A1 | 1/2008 | Voth |
| 2008/0033312 A1 | 2/2008 | Nakai et al. |
| 2008/0287777 A1 | 11/2008 | Li et al. |
| 2009/0005675 A1 | 1/2009 | Grunwald et al. |
| 2009/0024086 A1 | 1/2009 | Zhang et al. |
| 2009/0076483 A1 | 3/2009 | Danehorn |
| 2009/0131930 A1 | 5/2009 | Gelbart et al. |
| 2009/0143651 A1 | 6/2009 | Kallback et al. |
| 2009/0171274 A1 | 7/2009 | Harlev et al. |
| 2009/0264781 A1 | 10/2009 | Scharf |
| 2010/0067753 A1 | 3/2010 | Visser |
| 2010/0076426 A1 | 3/2010 | De La Rama et al. |
| 2010/0094279 A1 | 4/2010 | Kauphusman et al. |
| 2010/0168578 A1 | 7/2010 | Garson, Jr. et al. |
| 2010/0191131 A1 | 7/2010 | Revishvili et al. |
| 2010/0249623 A1 | 9/2010 | Makdissi |
| 2010/0256627 A1 | 10/2010 | Ma et al. |
| 2010/0286550 A1 | 11/2010 | Harlev et al. |
| 2010/0298690 A1 | 11/2010 | Scharf |
| 2011/0045130 A1 | 2/2011 | Edens et al. |
| 2011/0077526 A1 | 3/2011 | Zwirn |
| 2011/0082378 A1 * | 4/2011 | Messier ................. G16H 50/30 |
| | | 600/509 |
| 2011/0118726 A1 | 5/2011 | De La Rama et al. |
| 2011/0125172 A1 | 5/2011 | Gelbart et al. |
| 2011/0144510 A1 * | 6/2011 | Ryu .................... A61B 5/1107 |
| | | 600/509 |
| 2011/0172658 A1 | 7/2011 | Gelbart et al. |
| 2011/0190649 A1 | 8/2011 | Rudy et al. |
| 2011/0213231 A1 | 9/2011 | Hall et al. |
| 2011/0245702 A1 * | 10/2011 | Clark ....................... G01R 5/28 |
| | | 600/523 |
| 2011/0270237 A1 | 11/2011 | Werneth et al. |

(56) References Cited

U.S. PATENT DOCUMENTS

| | | | |
|---|---|---|---|
| 2011/0275949 | A1 | 11/2011 | Harlev et al. |
| 2012/0078077 | A1 | 3/2012 | Harlev et al. |
| 2012/0082969 | A1 | 4/2012 | Schwartz et al. |
| 2012/0136231 | A1 | 5/2012 | Markel |
| 2012/0143298 | A1 | 6/2012 | Just et al. |
| 2012/0165667 | A1 | 6/2012 | Altmann et al. |
| 2012/0172859 | A1 | 7/2012 | Condie et al. |
| 2012/0184863 | A1 | 7/2012 | Harlev et al. |
| 2012/0197117 | A1 | 8/2012 | Picot et al. |
| 2012/0271138 | A1 | 10/2012 | Kordis et al. |
| 2012/0271139 | A1 | 10/2012 | Kordis et al. |
| 2012/0277567 | A1 | 11/2012 | Harlev et al. |
| 2012/0277574 | A1 | 11/2012 | Panescu |
| 2012/0283587 | A1 | 11/2012 | Ghosh et al. |
| 2012/0284003 | A1 | 11/2012 | Ghosh et al. |
| 2012/0310064 | A1 | 12/2012 | Mcgee |
| 2013/0006238 | A1 | 1/2013 | Ditter et al. |
| 2013/0066316 | A1* | 3/2013 | Steinke .............. A61B 18/1492 606/41 |
| 2013/0085361 | A1 | 4/2013 | Mercanzini et al. |
| 2013/0096432 | A1 | 4/2013 | Hauck |
| 2013/0116561 | A1 | 5/2013 | Rothberg et al. |
| 2013/0158537 | A1 | 6/2013 | Deladi et al. |
| 2013/0165916 | A1 | 6/2013 | Mathur |
| 2013/0172715 | A1 | 7/2013 | Just et al. |
| 2013/0190587 | A1 | 7/2013 | Lopes et al. |
| 2013/0197614 | A1 | 8/2013 | Gustus et al. |
| 2013/0225983 | A1 | 8/2013 | Willis et al. |
| 2013/0226017 | A1 | 8/2013 | Scharf et al. |
| 2013/0245621 | A1 | 9/2013 | Persson et al. |
| 2013/0253298 | A1 | 9/2013 | Harlev et al. |
| 2013/0267853 | A1 | 10/2013 | Dausch et al. |
| 2013/0274582 | A1 | 10/2013 | Afonso et al. |
| 2013/0282084 | A1 | 10/2013 | Mathur et al. |
| 2013/0289417 | A1 | 10/2013 | Grunwald et al. |
| 2013/0304062 | A1 | 11/2013 | Chan et al. |
| 2013/0304065 | A1 | 11/2013 | Lopes et al. |
| 2013/0310827 | A1 | 11/2013 | Brewster et al. |
| 2013/0330701 | A1 | 12/2013 | Rubinstein et al. |
| 2014/0024910 | A1 | 1/2014 | Scharf et al. |
| 2014/0121470 | A1* | 5/2014 | Scharf ................. A61B 5/6858 600/301 |
| 2014/0148677 | A1 | 5/2014 | Liempde et al. |
| 2014/0180150 | A1 | 6/2014 | Scharf et al. |
| 2014/0200822 | A1 | 7/2014 | Dubois et al. |
| 2014/0235988 | A1 | 8/2014 | Ghosh |
| 2014/0257069 | A1 | 9/2014 | Eliason et al. |
| 2014/0275921 | A1 | 9/2014 | Harlev et al. |
| 2014/0276733 | A1 | 9/2014 | VanScoy et al. |
| 2014/0276746 | A1 | 9/2014 | Nabutovsky et al. |
| 2014/0276789 | A1 | 9/2014 | Dandler et al. |
| 2014/0278129 | A1* | 9/2014 | Voth ....................... G16H 50/50 702/19 |
| 2014/0358143 | A1 | 12/2014 | Novichenok et al. |
| 2015/0011886 | A1 | 1/2015 | Radulescu et al. |
| 2015/0038862 | A1 | 2/2015 | Gijsbers et al. |
| 2015/0164357 | A1 | 6/2015 | Zeng et al. |
| 2015/0196219 | A1 | 7/2015 | Scharf et al. |
| 2015/0208938 | A1 | 7/2015 | Houben et al. |
| 2015/0216434 | A1 | 8/2015 | Ghosh et al. |
| 2015/0216438 | A1 | 8/2015 | Bokan et al. |
| 2015/0223757 | A1* | 8/2015 | Werneth .............. A61B 5/0205 600/301 |
| 2015/0223863 | A1 | 8/2015 | Ghosh |
| 2015/0257732 | A1 | 9/2015 | Ryan |
| 2015/0257825 | A1 | 9/2015 | Kelly et al. |
| 2015/0342491 | A1 | 12/2015 | Marecki et al. |
| 2015/0351701 | A1* | 12/2015 | Moxon ................ A61B 5/7282 607/45 |
| 2015/0366508 | A1* | 12/2015 | Chou ..................... A61N 1/056 600/467 |
| 2015/0374252 | A1 | 12/2015 | de la Rama et al. |
| 2016/0007869 | A1 | 1/2016 | Scharf et al. |
| 2016/0038051 | A1 | 2/2016 | Scharf et al. |
| 2016/0051321 | A1 | 2/2016 | Salahieh et al. |
| 2016/0100770 | A1 | 4/2016 | Afonso et al. |
| 2016/0128771 | A1 | 5/2016 | Ditter et al. |
| 2016/0128772 | A1 | 5/2016 | Reinders et al. |
| 2016/0192902 | A1 | 7/2016 | Werneth et al. |
| 2016/0228019 | A1 | 8/2016 | Grunwald et al. |
| 2016/0317093 | A1* | 11/2016 | Berenfeld .............. A61B 5/287 |
| 2017/0035486 | A1 | 2/2017 | Lopes et al. |
| 2017/0049347 | A1 | 2/2017 | Ghosh et al. |
| 2017/0100049 | A1 | 4/2017 | Scharf et al. |
| 2017/0202469 | A1* | 7/2017 | Scharf ................... A61B 5/339 |
| 2017/0258347 | A1 | 9/2017 | Scharf et al. |
| 2017/0274204 | A1* | 9/2017 | Gunderson ........... A61B 5/283 |
| 2017/0319180 | A1 | 11/2017 | Jenneken et al. |
| 2017/0360319 | A1 | 12/2017 | Hagfors et al. |
| 2018/0055374 | A1 | 3/2018 | Scharf et al. |
| 2018/0146948 | A1 | 5/2018 | Chou et al. |
| 2018/0242871 | A1 | 8/2018 | Ghosh et al. |
| 2019/0021673 | A1 | 1/2019 | Werneth et al. |
| 2019/0159729 | A1 | 5/2019 | Chou et al. |
| 2019/0246930 | A1 | 8/2019 | Zhu et al. |
| 2021/0000423 | A1 | 1/2021 | Werneth et al. |
| 2021/0290960 | A1 | 9/2021 | Ghosh et al. |
| 2023/0218231 | A1 | 7/2023 | Chou et al. |
| 2025/0010080 | A1 | 1/2025 | Ghosh et al. |

FOREIGN PATENT DOCUMENTS

| | | | |
|---|---|---|---|
| CN | 201033076 | 3/2008 | |
| CN | 101254096 | 9/2008 | |
| CN | 201223445 | 4/2009 | |
| CN | 201275144 | 7/2009 | |
| CN | 101854853 | 10/2010 | |
| CN | 102481108 | 5/2012 | |
| CN | 103561642 | 2/2014 | |
| CN | 103829941 | 6/2014 | |
| CN | 104812297 | 7/2015 | |
| CN | 105358070 | 2/2016 | |
| EP | 1166714 | 1/2002 | |
| EP | 1760661 | 3/2007 | |
| EP | 1779787 | 5/2007 | |
| EP | 2051625 | 4/2009 | |
| EP | 2252203 | 11/2010 | |
| EP | 2683293 | 1/2014 | |
| EP | 2848191 | 3/2015 | |
| JP | 08501477 | 2/1996 | |
| JP | 10137207 | 5/1998 | |
| JP | 2001070269 | 3/2001 | |
| JP | 2002113004 | 4/2002 | |
| JP | 2002522106 | 7/2002 | |
| JP | 2003511098 | 3/2003 | |
| JP | 2004350702 | 12/2004 | |
| JP | 2005131367 | 5/2005 | |
| JP | 2005536313 | 12/2005 | |
| JP | 2006511296 | 4/2006 | |
| JP | 2009539566 | 11/2009 | |
| JP | 2011504363 | 2/2011 | |
| JP | 2011507656 | 3/2011 | |
| JP | 2015528352 | 9/2015 | |
| JP | 2016510683 | 4/2016 | |
| WO | 9406349 | 3/1994 | |
| WO | 9905971 | 2/1999 | |
| WO | 200007501 | 2/2000 | |
| WO | 200245608 | 6/2002 | |
| WO | 2002045608 | 6/2002 | |
| WO | 2003026722 | 4/2003 | |
| WO | 2004026134 | 4/2004 | |
| WO | 2006060613 | 6/2006 | |
| WO | WO-2007015199 A2 * | 2/2007 | ............. G06T 12/10 |
| WO | 2007146864 | 12/2007 | |
| WO | 2008014629 | 2/2008 | |
| WO | 2009065042 | 5/2009 | |
| WO | 2009090547 | 7/2009 | |
| WO | 2011136867 | 11/2011 | |
| WO | 2012092016 | 7/2012 | |
| WO | 2012100184 | 7/2012 | |
| WO | 2012100185 | 7/2012 | |
| WO | 2012110942 | 8/2012 | |
| WO | 2012122517 | 9/2012 | |

(56)                References Cited

FOREIGN PATENT DOCUMENTS

| WO | WO-2012122517 A2 * | 9/2012 | ........... A61B 5/0036 |
|----|----|----|----|
| WO | 2014124231 | 2/2013 | |
| WO | 2014036439 | 3/2014 | |
| WO | 2014130169 | 8/2014 | |
| WO | 2015073962 | 5/2015 | |
| WO | 2015148470 | 10/2015 | |
| WO | 2015171393 | 11/2015 | |
| WO | 2016020800 | 2/2016 | |
| WO | WO-2016020800 A1 * | 2/2016 | ............. A61B 5/285 |
| WO | 2016061384 | 4/2016 | |
| WO | WO-2016068923 A1 * | 5/2016 | ......... A61B 18/1492 |
| WO | 2017192769 | 11/2017 | |

OTHER PUBLICATIONS

Australian Office Action dated Nov. 2, 2023 issued in Australian Application No. 2022241612.
Japanese Office Action dated Jan. 31, 2017 issued in corresponding Japanese Application No. 2013-557-926, with English language summary.
Japanese Office Action dated Jun. 27, 2017 issued in corresponding Japanese Application No. 2015-530101. with English language translation.
Japanese Office Action dated Sep. 26, 2017 issued in corresponding Japanese Application No. 2017-155346, with English translation.
Office Action dated Nov. 7, 2017, issued in European Application No. 15768711.
Office Action dated Oct. 10, 2017, issued in Application No. 2015-557091 with machine translation to English.
Office Action issued on Mar. 9, 2016 in corresponding European Patent Application No. 13176658.6.
Office Action issued on May 30, 2016 in related Australian Patent Application No. 2012225250.
Office Action issued on Oct. 4, 2013 in corresponding Canadian Patent Application No. 2,659,898.
PCT ISRWO dated Jun. 5, 2014, issued in corresponding PCT Application No. PCT/US2013/057579.
Della Bella et al. "Non-contact mapping to guide catheter ablation of untolerated ventrical tachycardia" European Heart Journal, May 2002, 23(9)742-752.
Examination report dated Jul. 6, 2017 issued in Australian Patent Application No. 2014214756.
Examination Report dated Jun. 27, 2017 issued in Australian Application No. 2013308531.
Examiner's Report Dated Dec. 22 2015 in related Canadian Application No. 2656898.
Extended European Search Report for related U.S. Appl. No. 13/176,658 dated Sep. 29, 2014.
Extended European Search Report issued Jul. 8, 2016 in related European Application No. 14748567.6.
Gulrajani, Ramesh M. The Forward and Inverse Problems of Electrocardiograma, IEEE Engineering in Medicine and Biology Magazine, IEEE Service Center, Piscataway, NJ, U.S., vol. 17, No. 5, Sep. 1, 1998, pp. 84-101, 122.
Gupta et al. "Point of view cardiac mapping; utility or futility? Non-contact endocardial mapping" Indian Pacing and Electrophysiology Journal2:2Q-32 (2002).
He et al. "An equivalent body surface charge model representing three-dimensional bioelectrical activity" IEEE Transactions on Biomedical Engineering, 42.7 (Jul. 7, 1995) pp. 637-646.
International Search Report and Written Opinion in related Application No. PCT/US2012/028593 dated Mar. 5, 2013.
International Search Report in related Application No. PCT/IB2009/000071 dated Oct. 7, 2009.
Jackson JD, "Classical Electrodynamics", 3rd edition, Dec. 1998, pp. 31-34.
Jackson, JD, "Surface Distributions of Charges and Dipoles and Discontinuities in the Electric Field and Potential", Classical Electrodynamics, 3rd edition, Dec. 1998, pp. 31-34.

Leif et al., "Geometric modeling based on polygonal meshes". Eurographics 2000 Tutorial, Aug. 21, 2000.
Liu, Zhongming et al. "Noninvasive Reconstruction of Three-Dimensional Ventricular Activation Sequence From the Inverse Solution of Distributed Equivalent Current Density", IEEE Transactions on Medical Imaging, IEEE Service Center, Piscataway, NJ, U.S., vol. 25, No. 10, Oct. 1, 2006, pp. 1307-1318.
Martin, David R. et al. "Projected Tikhonov Regularization of Large-Scale Discrete Ill-Posed Problems", Journal of Scientific Computing, Springer U.S., Boston, MA vol. 56, No. 3, Feb. 10, 2013, pp. 471-493.
Office Action issued on Mar. 9, 2016 in corresponding European Patent Application No. 09702094.5.
Partial European Search Report dated Apr. 29, 2014 in corresponding European U.S. Appl. No. 13/176,658.
Patent Examination Report No 3 issued on Sep. 21, 2016 in related Australian Application No. 2012225250.
Pullan et al. "The inverse problem of electrocardiology" Northeastern University Electrical and Computer Engineering, Feb. 23, 2007.
Ramanathan, C. et al. "Noninvasive Electrocardiogramaging (ECGI): Application of the Generalized Minimal Residual (GMRes) Method", Annals of Biomedical Engineering, vol. 31 No. 8 (2003), pp. 981-994.
Van Oosterom A: "Solidifying the solid angle." 2002 Journal of Electrocardiology 2002 vol. 35 SUPPL pp. 181-192 ISSN: 0022-0736.
William G. Stevenson et al: "Recording Techniques for Clinical Electrophysiology" Journal of Cardiovascular Electrophysiology. vol. 16 No. 91, Sep. 2005, pp. 1017-1022.
William G. Stevenson et al; "Recording Techniques for Clinical Electrophysiology", Journal of Cardiovascular Electrophysiology, vol. 16, No. 9, Sep. 1, 2005, pp. 1017-1022, XP55222320.
Wolfgang Nolting: Elektrodynamik—Grundkurs Theoretische Physik 3 Springer Spektrum pp. D 89-91.
Wolfgang Nolting: Elektrodynamik—Grundkurs Theoretische Physik 3, Springer Spectrum, p. 89-91, XP009188752.
Copy of Chinese Office Action dated Jun. 28, 2024 issued in Chinese Application No. 202111503914.6, with machine translation to English.
Copy of European Office Action dated Mar. 27, 2024 issued in European Application No. 21192952.6.
Japanese Notice of Allowance dated Aug. 3, 2021 issued in corresponding Japanese Application No. 2018-557371, with machine translation to English.
Office Action issued on Apr. 27, 2016 in corresponding Canadian Application No. 2,747,859.
Anoop Kumar Gupta, et al., "Point of View Cardiac Mapping: Utility or Futility?", Non-contact Endocardial Mapping Indian Pacing and Electrophysiology Journal, vol. 2, No. 1, Jan. 1, 2002, pp. 20-32 XP055128732.
Christoph Scharft et al. Declaration under 37 C.F.R. 1.132, Nov. 15, 2012.
Coll-Font et al. "New Additions to the Toolkit for Forward/Inverse Problems in Electrocardiogramathin the SCIRun Problem Solving Environment", Computing in Cardiology, 2014, vol. 41, pp. 213-216.
Australian Examination Report dated Jun. 28, 2018, issued in corresponding Australian Patent Application No. 2014318872.
Australian Office Action dated Feb. 26, 2018 issued in Australian Application No. 2017201560.
Australian Office Action dated Jun. 14, 2018 issued in Australian Application No. 2014214756.
Australian Office Action dated Mar. 17, 2018 issued in corresponding Australian Application No. 2013308531.
Canadian Office Action dated Apr. 26, 2017 issued in corresponding Canadian Application No. 2932956.
Canadian Office Action dated Jan. 22, 2018 issued in corresponding Canadian Application No. 2932956.
Canadian Office Action dated Mar. 30, 2017 issued in corresponding Canadian Application No. 2747859.
Canadian Office Action dated Nov. 27, 2017 issued in corresponding Canadian Application No. 2829626.

(56)         References Cited

OTHER PUBLICATIONS

Canadian Office Action dated Oct. 29, 2018 issued in corresponding Canadian Application No. 2829626.
Chinese Office Action dated Apr. 17, 2017 issued in corresponding Chinese Application No. 201480018328.4.
Chinese Office Action dated Mar. 3, 2021 issued in corresponding Chinese Application No. 201780040472.1.
Decision dated Jan. 16, 2018 issued for European Patent Application No. 09702094.5.
Decision dated Jan. 18 issued for European Patent Application No. 13176658.6.
Decision dated Jan. 18, 2018 issued for European Patent Application No. 13176658.6.
European Office Action dated Apr. 23, 2018 issued in corresponding European Application No. 07785075.8.
European Office Action dated Apr. 28, 2014, issued in corresponding European Application No. 09 702 094.5-1660.
European Office Action dated Feb. 29, 2016 issued in corresponding European Application No. 07 785 075.8-1657.
European Office Action dated Jan. 31, 2018, issued in corresponding European Application No. 13763151.1.
European Office Action dated Jul. 21, 2020 issued in corresponding European Application No. 17793291.0.
European Office Action dated Mar. 21, 2017 issued in corresponding European Application No. 07785075.8.
Extended European Search Report dated Feb. 25, 2022 issued in corresponding European Application No. 21192952.6.
Extended European Search Report dated Mar. 14, 2017 issued in corresponding European Application No. EP14843283.4.
Extended European Search Report dated Oct. 18, 2017, issued in European Application No. 15768711.
Extended European Search Report dated Oct. 23, 2019 issued in corresponding European Application No. 17793291.0.
Extended European Search Report dated Oct. 4, 2018 issued in corresponding European Application No. 16793503.0.
Extended European Search Report dated Sep. 13, 2019 issued in corresponding European Application No. 17793286.0.
International Search Report and Written Opinion dated Aug. 4, 2017 issued in corresponding International Application No. PCT/US17/30915.
International Search Report and Written Opinion dated Dec. 12, 2017 issued in corresponding International Application No. PCT/US2017/056064.
International Search Report and Written Opinion dated Jun. 26, 2015 issued in International Application No. PCT/US2015/022187.
International Search Report and Written Opinion dated Sep. 25, 2017, issued in corresponding Application No. PCT/US17/30922.
International Search Report dated Mar. 10, 2015 issued in corresponding International Application No. PCT/US14/54942.
International Search Report issued Apr. 14, 2008 in related International Application No. PCT/CH2007/000380.

Invitation to Pay Additional Fees issued on Jan. 8, 2014 in corresponding International Application No. PCT/US2013/057579.
Israel Office Action dated Oct. 21, 2021 issued in corresponding Israel Application No. 262730, with English translation.
ISRWO dated Aug. 8, 2016 issued in corresponding European Application No. PCT/US2016/031823.
ISRWO dated Aug. 11, 2016 issued in corresponding International Application No. PCT/US2016/032017.
ISRWO dated Aug. 18, 2016 issued in corresponding International Application No. PCT/US16/32420.
ISRWO issued on May 20, 2014 in International application No. PCT/US14/15261.
Japanese Notice of Allowance dated Feb. 27, 2018 issued in corresponding Japanese Application No. 2015-530101, with English language translation.
Japanese Notice of Allowance dated Jan. 16, 2018 issued in corresponding Japanese Application No. 2017-155346, with English translation.
Japanese Notice of Allowance dated Jul. 11, 2017 issued in corresponding Japanese Application No. 2013-557-926, with English language summary.
Japanese Notice of Allowance dated Sep. 18, 2018 issued in corresponding Japanese Application No. 2015-557091, with English language translation.
Japanese Office Action dated Apr. 6, 2021 issued in corresponding Japanese Application No. 2018-557371 (Docket No. ACU-040JP), with machine translation to English.
Japanese Office Action dated Aug. 28, 2018 issued in corresponding Japanese Application No. 2016-542062, with machine translation to English.
Japanese Office Action dated Feb. 16, 2016 issued in corresponding Japanese Application No. 2013-557-926, with English language summary.
European Office Action dated Jan. 13, 2025 issued in European Application No. 21192952.6.
European Office Action dated Apr. 15, 2025 issued in European Application No. 17793286.0.
European Office Action dated Jul. 20, 2022 issued in European Application No. 17793286.0.
Gepstein et al. "Electroanatomical Mapping of the Heart: Basic Concepts and Implications for the Treatment of Cardiac Arrhythmias", PACE—Pacing and Clinical Electrophysiology, vol. 21, No. 6, Jun. 1, 1998, pp. 1268-1278, XP093268784, US ISSN: 0147-8389, DOI: 10.1111/j.1540-8159.1998.tb00187.x.
Sy et al. "Modern Electrophysiology Mapping Techniques", Heart, Lung and Circulation, vol. 21, No. 6 , pp. 364-375, XP028429030, ISSN: 1443-9506, DOI: 10.1016/J.HLC.2012.04.007, retrieved on Apr. 20, 2012.
Chinese Office Action dated Feb. 27, 2025 issued in Chinese Application No. 202111503914.6, with machine translation to English.
Summons to Attend Oral Proceedings dated Jul. 23, 2025 issued in European Application No. 21192952.6.

* cited by examiner

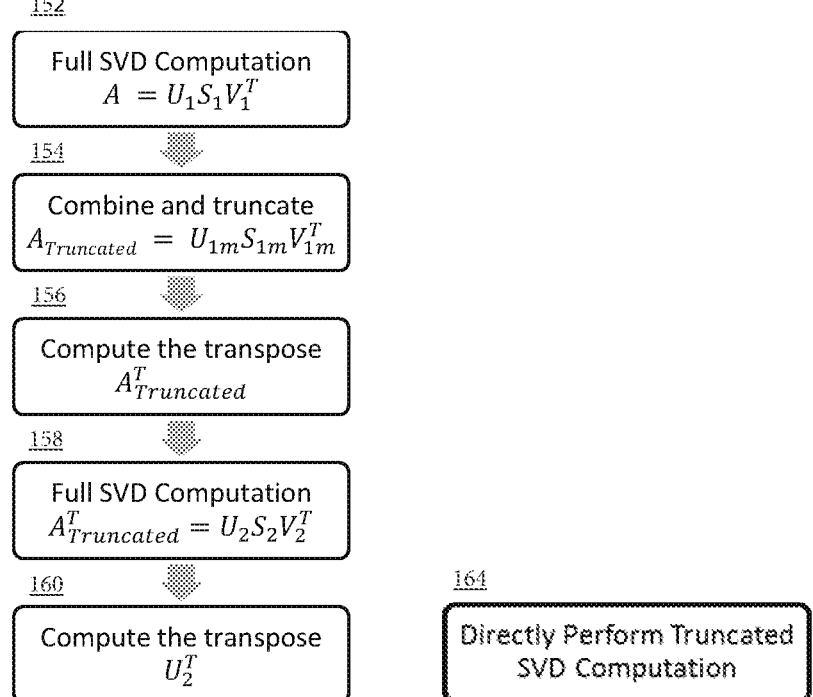
152
Full SVD Computation
$A = U_1 S_1 V_1^T$
154
Combine and truncate
$A_{Truncated} = U_{1m} S_{1m} V_{1m}^T$
156
Compute the transpose
$A_{Truncated}^T$
158
Full SVD Computation
$A_{Truncated}^T = U_2 S_2 V_2^T$
160
Compute the transpose
$U_2^T$
164
Directly Perform Truncated
SVD Computation
FIG. 1A          FIG. 1B

300

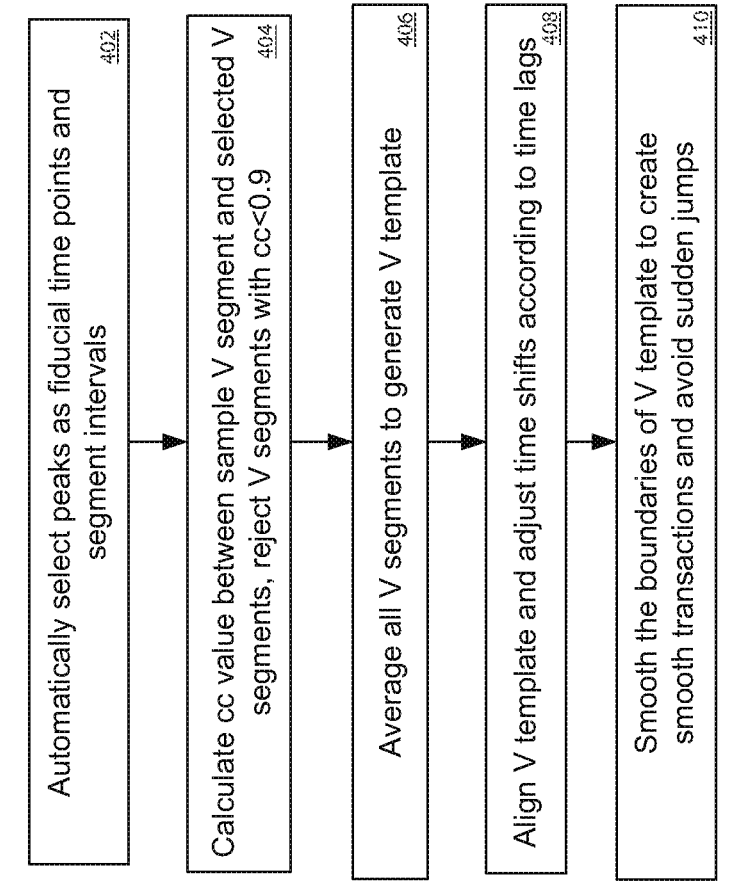

400

Automatically select peaks as fiducial time points and segment intervals
402

Calculate cc value between sample V segment and selected V segments, reject V segments with cc<0.9
404

Average all V segments to generate V template
406

Align V template and adjust time shifts according to time lags
408

Smooth the boundaries of V template to create smooth transactions and avoid sudden jumps
410

FIG. 4

Block diagram for flow control, field estimation and aux. localization

Integration Path to Target Frame.

Line A shows the direct path between the origin and the target frame.

Intermediate centriods (with attached local reference frames) are labeled 1-4.

Position vectors between frames are shown by line B, and labeled (1)-(4).

IFE Algorithm

A point (X, Y, Z) is shown relative to three local references frames and the origin.

Position vectors from the local frames to the point are shown by A.

Position vectors from the origin to the local frames are shown by B.

Block Diagram of a scaling algorithm.

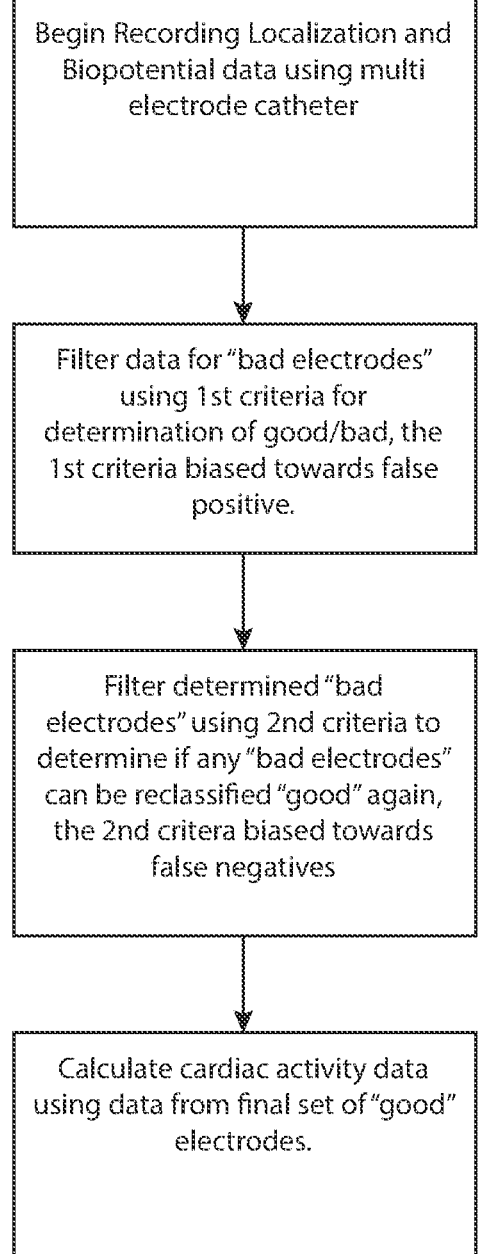

Begin Recording Localization and Biopotential data using multi electrode catheter Filter data for "bad electrodes" using 1st criteria for determination of good/bad, the 1st criteria biased towards false positive.

Filter determined "bad electrodes" using 2nd criteria to determine if any "bad electrodes" can be reclassified "good" again, the 2nd critera biased towards false negatives Calculate cardiac activity data using data from final set of "good" electrodes.

FIG. 10

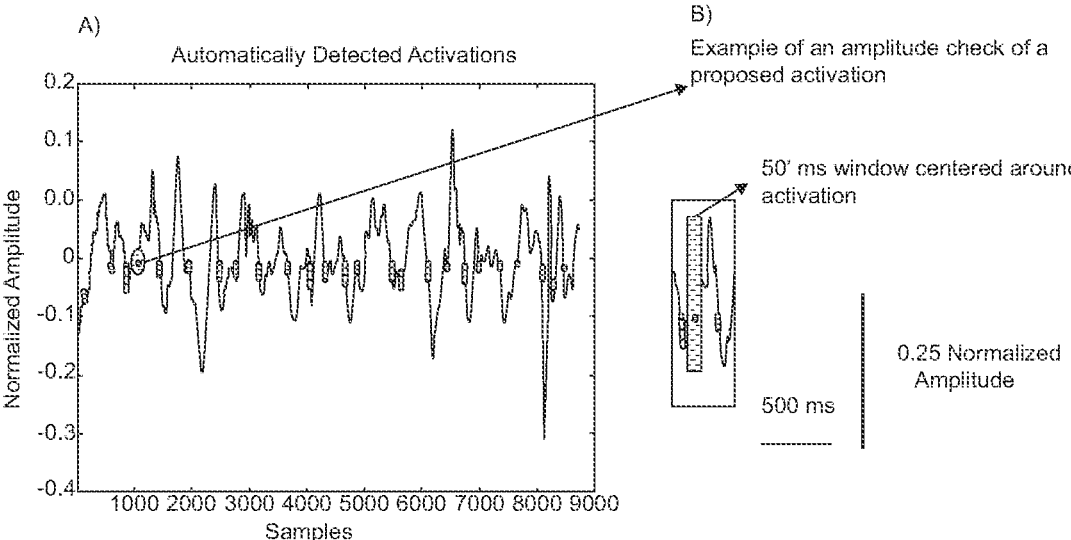
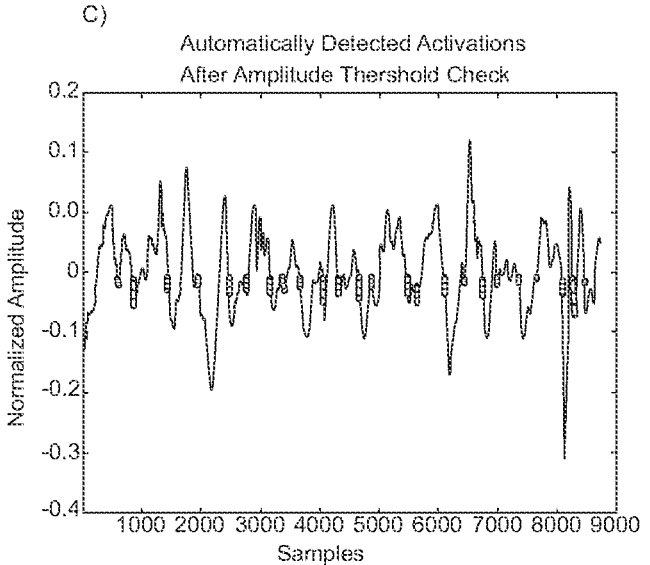
FIG. 14

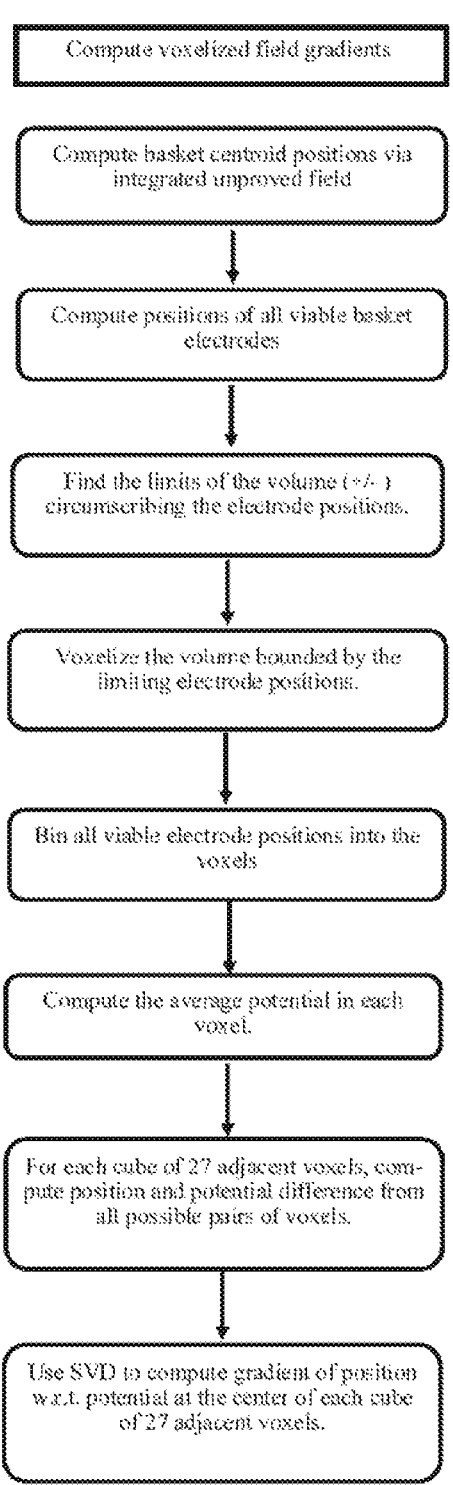
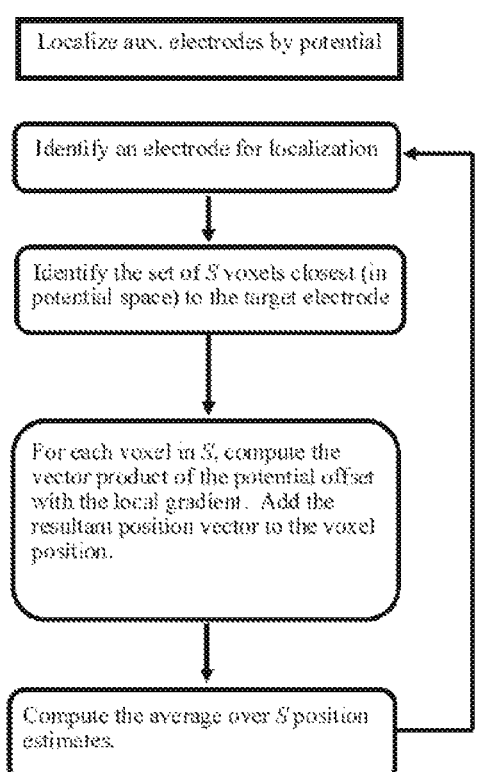
FIG. 18B
FIG. 18A

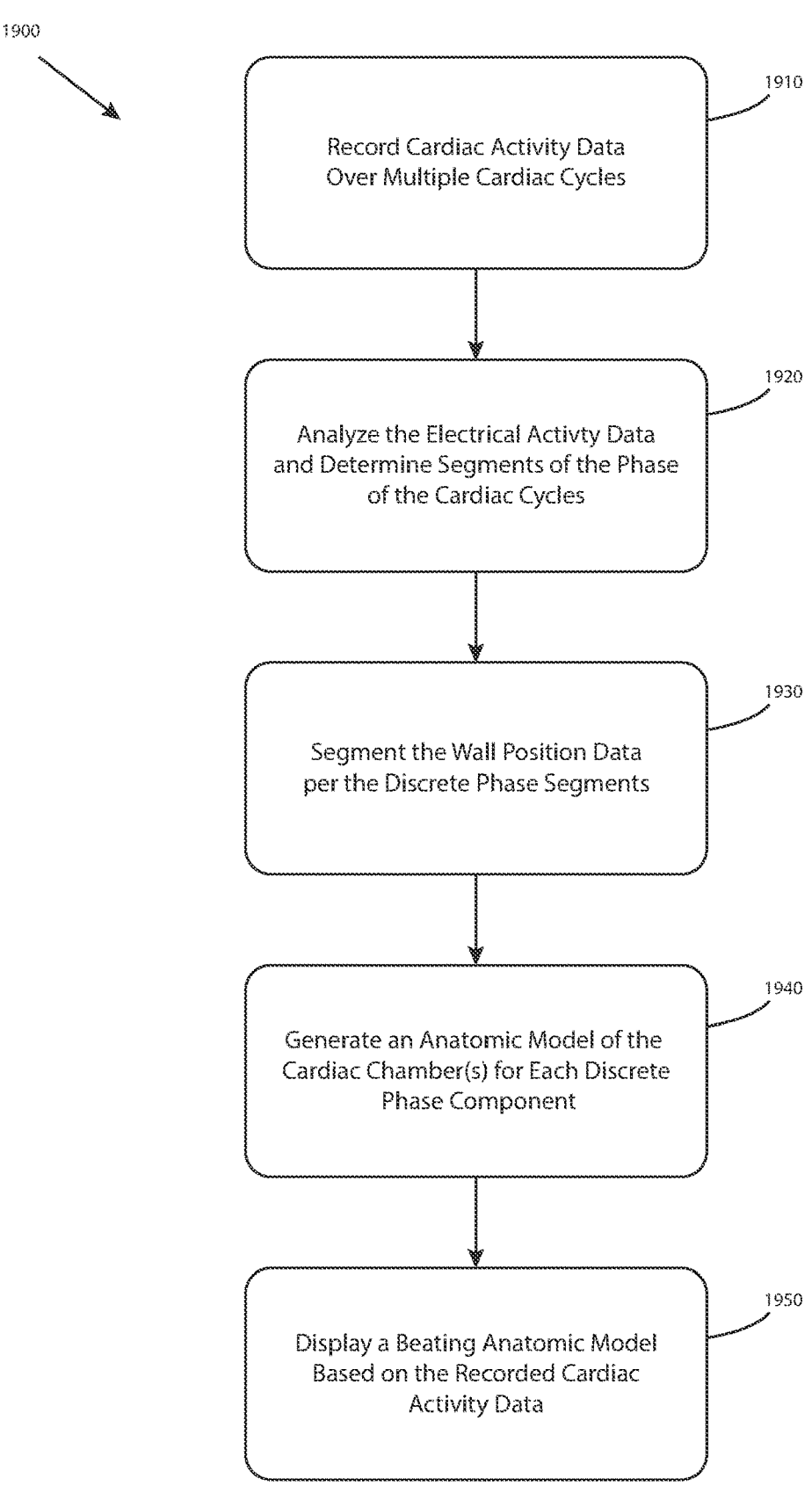

1900

Record Cardiac Activity Data
Over Multiple Cardiac Cycles                    1910

Analyze the Electrical Activty Data
and Determine Segments of the Phase
of the Cardiac Cycles                           1920

Segment the Wall Position Data
per the Discrete Phase Segments                 1930

Generate an Anatomic Model of the
Cardiac Chamber(s) for Each Discrete
Phase Component                                 1940

Display a Beating Anatomic Model
Based on the Recorded Cardiac
Activity Data                                   1950

FIG. 19

CARDIAC MAPPING SYSTEM WITH EFFICIENCY ALGORITHM

RELATED APPLICATIONS

The present application is a continuation of U.S. patent application Ser. No. 16/097,959, entitled "CARDIAC MAPPING SYSTEM WITH EFFICIENCY ALGORITHM", filed Oct. 31, 2018, which is a 35 USC 371 national stage entry of Patent Cooperation Treaty Application No. PCT/US2017/030922, entitled "CARDIAC MAPPING SYSTEM WITH EFFICIENCY ALGORITHM," filed May 3, 2017, which claims priority to U.S. Provisional Patent Application Ser. No. 62/413,104, entitled "CARDIAC MAPPING SYSTEM WITH EFFICIENCY ALGORITHM," filed Oct. 26, 2016, and U.S. Provisional Patent Application Ser. No. 62/331,364, entitled "CARDIAC MAPPING SYSTEM WITH EFFICIENCY ALGORITHM," filed May 3, 2016, each of which is incorporated herein by reference in its entirety.

The present application, while not claiming priority to, may be related to U.S. patent application Ser. No. 14/865, 435, entitled "Method and Device for Determining and Presenting Surface Charge and Dipole Densities on Cardiac Walls", filed Sep. 25, 2015, which is a continuation of U.S. Pat. No. 9,167,982, entitled "Method and Device for Determining and Presenting Surface Charge and Dipole Densities on Cardiac Walls", filed Nov. 19, 2014, which is a continuation of U.S. Pat. No. 8,918,158 (hereinafter the '158 patent), entitled "Method and Device for Determining and Presenting Surface Charge and Dipole Densities on Cardiac Walls", issued Dec. 23, 2014, which is a continuation of U.S. Pat. No. 8,700,119 (hereinafter the '119 patent), entitled "Method and Device for Determining and Presenting Surface Charge and Dipole Densities on Cardiac Walls", issued Apr. 15, 2014, which is a continuation of U.S. Pat. No. 8,417,313 (hereinafter the '313 patent), entitled "Method and Device for Determining and Presenting Surface Charge and Dipole Densities on Cardiac Walls", issued Apr. 9, 2013, which was a 35 USC 371 national stage filing of PCT Application No. CH2007/000380, entitled "Method and Device for Determining and Presenting Surface Charge and Dipole Densities on Cardiac Walls", filed Aug. 3, 2007, published as WO 2008/014629, which claimed priority to Swiss Patent Application No. 1251/06 filed Aug. 3, 2006, each of which is hereby incorporated by reference.

The present application, while not claiming priority to, may be related to U.S. patent application Ser. No. 14/886, 449, entitled "Device and Method for the Geometric Determination of Electrical Dipole Densities on the Cardiac Wall", filed Oct. 19, 2015, which is a continuation of U.S. Pat. No. 9,192,318, entitled "Device and Method for the Geometric Determination of Electrical Dipole Densities on the Cardiac Wall", filed Jul. 19, 2013, which is a continuation of U.S. Pat. No. 8,512,255, entitled "Device and Method for the Geometric Determination of Electrical Dipole Densities on the Cardiac Wall", issued Aug. 20, 2013, published as US2010/0298690 (hereinafter the '690 publication), which was a 35 USC 371 national stage application of Patent Cooperation Treaty Application No. PCT/IB09/00071 filed Jan. 16, 2009, entitled "A Device and Method for the Geometric Determination of Electrical Dipole Densities on the Cardiac Wall", published as WO2009/090547, which claimed priority to Swiss Patent Application 00068/08 filed Jan. 17, 2008, each of which is hereby incorporated by reference.

The present application, while not claiming priority to, may be related to U.S. application Ser. No. 14/003,671, entitled "Device and Method for the Geometric Determination of Electrical Dipole Densities on the Cardiac Wall", filed Sep. 6, 2013, which is a 35 USC 371 national stage filing of Patent Cooperation Treaty Application No. PCT/US2012/028593, entitled "Device and Method for the Geometric Determination of Electrical Dipole Densities on the Cardiac Wall", published as WO2012/122517 (hereinafter the '517 publication), which claimed priority to US Patent Provisional Application Ser. No. 61/451,357, each of which is hereby incorporated by reference.

The present application, while not claiming priority to, may be related to U.S. Design application Ser. No. 29/475, 273, entitled "Catheter System and Methods of Medical Uses of Same, Including Diagnostic and Treatment Uses for the Heart", filed Dec. 2, 2013, which is a 35 USC 371 national stage filing of Patent Cooperation Treaty Application No. PCT/US2013/057579, entitled "Catheter System and Methods of Medical Uses of Same, Including Diagnostic and Treatment Uses for the Heart", filed Aug. 30, 2013, which claims priority to U.S. Patent Provisional Application Ser. No. 61/695,535, entitled "System and Method for Diagnosing and Treating Heart Tissue", filed Aug. 31, 2012, which is hereby incorporated by reference.

The present application, while not claiming priority to, may be related to Patent Cooperation Treaty Application No. PCT/US2014/15261, entitled "Expandable Catheter Assembly with Flexible Printed Circuit Board (PCB) Electrical Pathways", filed Feb. 7, 2014, which claims priority to U.S. Patent Provisional Application Ser. No. 61/762,363, entitled "Expandable Catheter Assembly with Flexible Printed Circuit Board (PCB) Electrical Pathways", filed Feb. 8, 2013, which is hereby incorporated by reference.

The present application, while not claiming priority to, may be related to Patent Cooperation Treaty Application No. PCT/US2015/11312, entitled "Gas-Elimination Patient Access Device", filed Jan. 14, 2015, which claims priority to U.S. Patent Provisional Application Ser. No. 61/928,704, entitled "Gas-Elimination Patient Access Device", filed Jan. 17, 2014, which is hereby incorporated by reference.

The present application, while not claiming priority to, may be related to Patent Cooperation Treaty Application No. PCT/US2015/22187, entitled "Cardiac Analysis User Interface System and Method", filed Mar. 24, 2015, which claims priority to U.S. Patent Provisional Application Ser. No. 61/970,027, entitled "Cardiac Analysis User Interface System and Method", filed Mar. 28, 2014, which is hereby incorporated by reference.

The present application, while not claiming priority to, may be related to Patent Cooperation Treaty Application No. PCT/US2014/54942, entitled "Devices and Methods for Determination of Electrical Dipole Densities on a Cardiac Surface", filed Sep. 10, 2014, which claims priority to U.S. Patent Provisional Application Ser. No. 61/877,617, entitled "Devices and Methods for Determination of Electrical Dipole Densities on a Cardiac Surface", filed Sep. 13, 2013, which is hereby incorporated by reference.

The present application, while not claiming priority to, may be related to U.S. Patent Provisional Application Ser. No. 62/161,213, entitled "Localization System and Method Useful in the Acquisition and Analysis of Cardiac Information", filed May 13, 2015, which is hereby incorporated by reference.

The present application, while not claiming priority to, may be related to U.S. Patent Provisional Application Ser. No. 62/160,501, entitled "Cardiac Virtualization Test Tank and Testing System and Method", filed May 12, 2015, which is hereby incorporated by reference.

The present application, while not claiming priority to, may be related to U.S. Patent Provisional Application Ser. No. 62/160,529, entitled "Ultrasound Sequencing System and Method", filed May 12, 2015, which is hereby incorporated by reference.

FIELD

The present invention is generally related to systems and methods that may be useful for the diagnosis and treatment of cardiac arrhythmias or other abnormalities, in particular, the present invention is related to systems, devices, and methods useful in displaying cardiac activities associated with diagnosing and treating such arrhythmias or other abnormalities.

BACKGROUND

Cardiac signals (e.g., charge density, dipole density, voltage, etc.) vary across the endocardial surface in magnitude. The magnitude of these signals is dependent on several factors, including local tissue characteristics (e.g., healthy vs. disease/scar/fibrosis/lesion) and regional activation characteristics (e.g., "electrical mass" of activated tissue prior to activation of the local cells). A common practice is to assign a single threshold for all signals at all times across the surface. The use of a single threshold can cause low-amplitude activation to be missed or cause high-amplitude activation to dominate/saturate, leading to confusion in interpretation of the map. Failure to properly detect activation can lead to imprecise identification of regions of interest for therapy delivery or incomplete characterization of ablation efficacy (excess or lack of block).

The continuous, global mapping of atrial fibrillation yields a tremendous volume of temporally- and spatially-variable activation patterns. A limited, discrete sampling of map data may be insufficient to provide a comprehensive picture of the drivers, mechanisms, and supporting substrate for the arrhythmia. Clinician review of long durations of AF can be challenging to remember and piece together to complete the "bigger picture."

SUMMARY

According to one aspect of the present inventive concepts, a cardiac information dynamic display system, comprises: one or more electrodes configured to record sets of electric potential data representing cardiac activity at a plurality of time intervals; and a cardiac information console, comprising: a signal processor configured to: calculate sets of cardiac activity data at the plurality of time intervals using the recorded sets of electric potential data, wherein the cardiac activity data is associated with surface locations of one or more cardiac chambers; and a user interface module configured to display a series of images, each image comprising: a graphical representation of the cardiac activity; wherein the signal processor comprises: an automated orientation system configured to orient one or more localization axes in a desired direction and/or rotate a localization coordinate system toward a physiologic orientation.

According to another aspect of the present inventive concepts, a cardiac information dynamic display system, comprises: one or more electrodes configured to record sets of electric potential data representing cardiac activity at a plurality of time intervals; and a cardiac information console, comprising: a signal processor configured to: calculate sets of cardiac activity data at the plurality of time intervals using the recorded sets of electric potential data, wherein the cardiac activity data is associated with surface locations of one or more cardiac chambers; and a user interface module configured to display a series of images, each image comprising: a graphical representation of the cardiac activity; wherein the signal processor comprises: a cardiac information algorithm that directly performs a truncated SVD computation to calculate the sets of cardiac activity data.

According to another aspect of the present inventive concepts, a cardiac information dynamic display system, comprises: one or more electrodes configured to record sets of electric potential data representing cardiac activity at a plurality of time intervals; and a cardiac information console, comprising: a signal processor configured to: calculate sets of cardiac activity data at the plurality of time intervals using the recorded sets of electric potential data, wherein the cardiac activity data is associated with surface locations of one or more cardiac chambers; and a user interface module configured to display a series of images, each image comprising: a graphical representation of the cardiac activity; wherein the signal processor comprises: a non-functional electrode detection algorithm configured to assess the one or more electrodes for adequate functionality.

In some embodiments, the signal processor is further configured to not include voltages measured from electrodes identified by the non-functional electrode detection algorithm to calculate the sets of cardiac activity data.

According to another aspect of the present inventive concepts, a cardiac information dynamic display system, comprising: one or more electrodes configured to record sets of electric potential data representing cardiac activity at a plurality of time intervals; and a cardiac information console, comprising: a signal processor configured to: calculate sets of cardiac activity data at the plurality of time intervals using the recorded sets of electric potential data, wherein the cardiac activity data is associated with surface locations of one or more cardiac chambers; and a user interface module configured to display a series of images, each image comprising: a graphical representation of the cardiac activity; wherein the console comprises: an analog-to-digital converter; and a subsystem configured to automatically turn off the analog-to-digital converter under certain conditions.

According to another aspect of the present inventive concepts, a cardiac information dynamic display system, comprises: one or more electrodes configured to record sets of electric potential data representing cardiac activity at a plurality of time intervals; and a cardiac information console, comprising: a signal processor configured to: calculate sets of cardiac activity data at the plurality of time intervals using the recorded sets of electric potential data, wherein the cardiac activity data is associated with surface locations of one or more cardiac chambers; and a user interface module configured to display a series of images, each image comprising: a graphical representation of the cardiac activity; wherein the signal processor comprises: an algorithm configured to reduce the effects of ventricular far field signals.

According to another aspect of the present inventive concepts, a cardiac information dynamic display system, comprises: one or more electrodes configured to record sets of electric potential data representing cardiac activity at a plurality of time intervals; and a cardiac information console, comprising: a signal processor configured to: calculate sets of cardiac activity data at the plurality of time intervals using the recorded sets of electric potential data, wherein the cardiac activity data is associated with surface locations of one or more cardiac chambers; and a user interface module configured to display a series of images, each image comprising: a graphical representation of the cardiac activity; wherein the signal processor comprises: a registration handling subsystem configured to correlate voltage measurements to locations.

According to another aspect of the present inventive concepts, a cardiac information dynamic display system, comprising: one or more electrodes configured to record sets of electric potential data representing cardiac activity at a plurality of time intervals; and a cardiac information console, comprising: a signal processor configured to: calculate sets of cardiac activity data at the plurality of time intervals using the recorded sets of electric potential data, wherein the cardiac activity data is associated with surface locations of one or more cardiac chambers; and a user interface module configured to display a series of images, each image comprising: a graphical representation of the cardiac activity; wherein the signal processor comprises: an improved field estimation algorithm.

According to another aspect of the present inventive concepts, a cardiac information dynamic display system, comprising: one or more electrodes configured to record sets of electric potential data representing cardiac activity at a plurality of time intervals; and a cardiac information console, comprising: a signal processor configured to: calculate sets of cardiac activity data at the plurality of time intervals using the recorded sets of electric potential data, wherein the cardiac activity data is associated with surface locations of one or more cardiac chambers; and a user interface module configured to display a series of images, each image comprising: a graphical representation of the cardiac activity; wherein the signal processor comprises: a forward matrix and an inverse solution; and a scaling algorithm comprising a pre-scaling portion configured to reduce distance influence on the forward matrix and a post-scaling portion to adjust the output of the inverse solution.

BRIEF DESCRIPTION OF THE DRAWINGS

FIG. 1A and FIG. 1B are two flow charts showing methods for performing SVD computation, in accordance with aspects of the inventive concept.

FIG. 4 is a flow chart of performing V-wave removal, in accordance with aspects of the inventive concept.

FIG. 10 shows a flow chart of the steps to reclassify non-functional electrodes for use in calculating cardiac activity, in accordance with aspects of the inventive concept.

FIG. 14 shows one example implementation of false positive activation annotations removal, in accordance with aspects of the inventive concept.

FIGS. 18A and 18B show two examples using voxels, in accordance with aspects of the inventive concept.

FIG. 19 is a flow chart of an embodiment of a method for generating a beating anatomic model of the heart, in accordance with aspects of the inventive concept.

DETAILED DESCRIPTION

Figure 1:
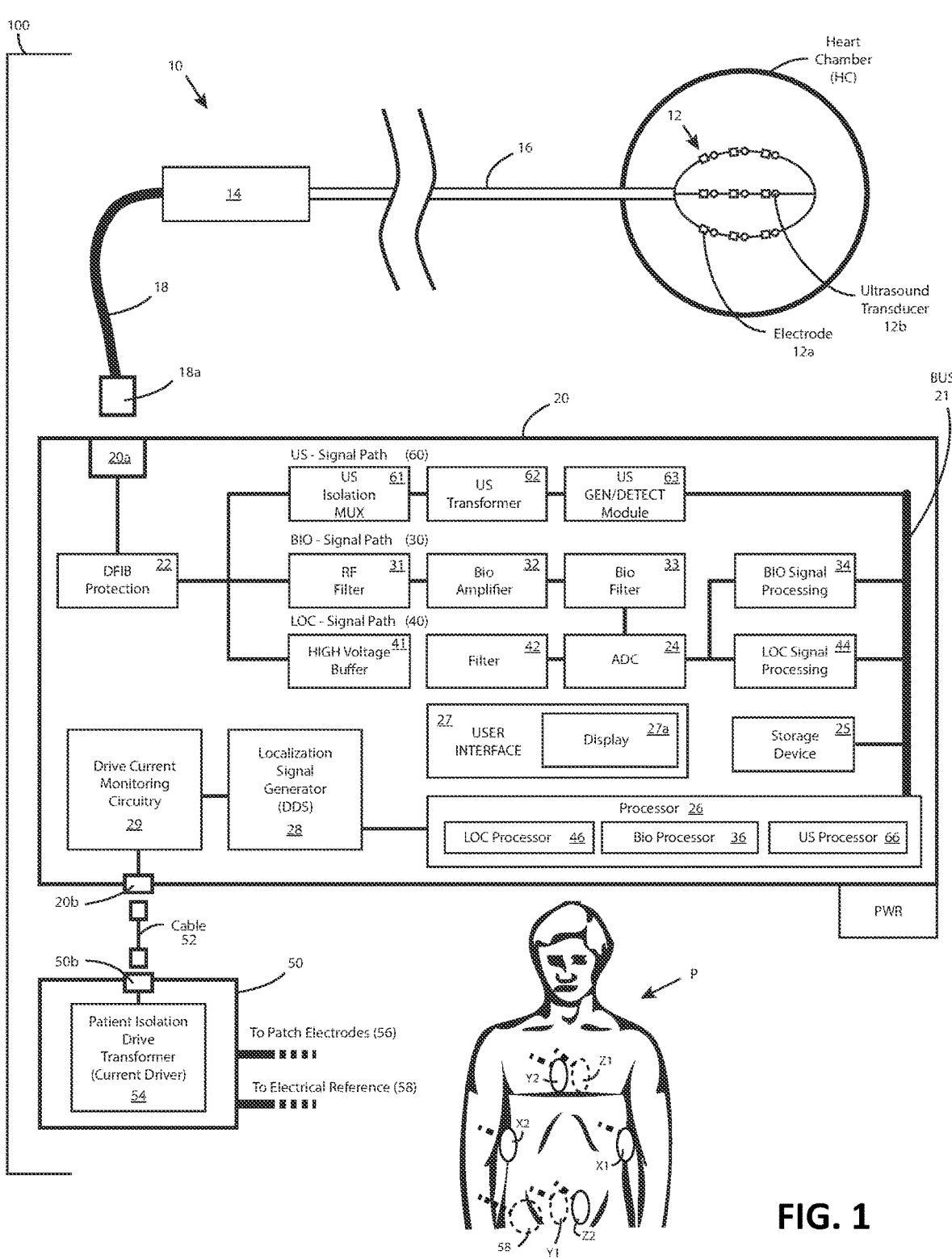
FIG. 1 is a block diagram of an embodiment of a cardiac information processing system, in accordance with aspects of the inventive concept.

Various exemplary embodiments will be described more fully hereinafter with reference to the accompanying drawings, in which some exemplary embodiments are shown. The present inventive concept can, however, be embodied in many different forms and should not be construed as limited to the exemplary embodiments set forth herein.

It will be understood that, although the terms first, second, etc. are used herein to describe various elements, these elements should not be limited by these terms. These terms are used to distinguish one element from another, but not to imply a required sequence of elements. For example, a first element can be termed a second element, and, similarly, a second element can be termed a first element, without departing from the scope of the present invention. As used herein, the term "and/or" includes any and all combinations of one or more of the associated listed items. And a "combination" of associated listed items need not include all of the items listed, but can include all of the items listed.

It will be understood that when an element is referred to as being "on" or "attached", "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

Spatially relative terms, such as "beneath," "below," "lower," "above," "upper" and the like can be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in the figures is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

Localization describes the process of establishing a coordinate system, and using one or more signals, such as electronic signals, to determine the position of one or more objects within that system. In some embodiments, the process of localization incorporates one or more signals generated from one or more sources that change as a function of space and/or time and a sensor, detector, or other transducer that measures the generated signal from a location. The location of the sensor can be on the object being localized or can be separate from the object being localized. Analysis of and/or calculation on the measured signal can be used to determine a positional relationship of the sensor and/or the object to the one or more sources of the generated signal. The method of localization can incorporate two or more generated signals to increase the number or accuracy of positional relationships between the sensor and the source. The source, sensor, and/or object can be co-located or can be the same device. In some embodiments, the change as a function of time and/or space includes the interaction of the generated signal with the measurement environment. In other embodiments, the process of localization measures an intrinsic or existing property or characteristic of the object, sensor, or environment, such as measuring a signal from an accelerometer positioned on the object or sensor.

Various exemplary embodiments are described herein with reference illustrations of idealized or representative structures and intermediate structures. As such, variations from the shapes of the illustrations as a result, for example, of manufacturing techniques and/or tolerances, are to be expected. Thus, exemplary embodiments should not be construed as limited to the particular shapes of regions illustrated herein but are to include deviations in shapes that result, for example, from manufacturing.

To the extent that functional features, operations, and/or steps are described herein, or otherwise understood to be included within various embodiments of the inventive concept, such functional features, operations, and/or steps can be embodied in functional blocks, units, modules, operations and/or methods. And to the extent that such functional blocks, units, modules, operations and/or methods include computer program code, such computer program code can be stored in a computer readable medium, e.g., such as non-transitory memory and media, that is executable by at least one computer processor.

Referring now to FIG. 1, provided is a block diagram of an embodiment of a cardiac information processing system 100, in accordance with aspects of the inventive concept. The cardiac information processing system 100 can be or include a system configured to perform cardiac mapping, diagnosis, and/or treatment, such as for treating a disease or disorder of a patient, such as an arrhythmia. Additionally or alternatively, the system can be a system configured for teaching and or validating devices and methods of diagnosing and/or treating cardiac abnormalities or disease of a patient P. The system can further be used for generating displays of cardiac activity, such as dynamic displays of active wave fronts propagating across surfaces of the heart.

The cardiac information processing system 100 includes a catheter 10, a cardiac information console 20, and a patient interface module 50 that can be configured to cooperate to accomplish the various functions of the cardiac information processing system 100. The cardiac information processing system 100 can include a single power supply (PWR), which can be shared by the cardiac information console 20 and the patient interface module 50. Use of a single power supply in this way can greatly reduce the chance for leakage currents to propagate into the patient interface module 50 and cause errors in localization, i.e., the process of determining the location of one or more electrodes within the body of patient P. Cardiac information console 20 includes bus 21 which electrically or operatively connects various components of console 20 to each other, as shown in FIG. 1.

The catheter 10 includes an electrode array 12 that can be percutaneously delivered to a heart chamber (HC). In this embodiment, the array of electrodes 12 has a known spatial configuration in three-dimensional (3D) space. For example, in an expanded state the physical relationship of the electrode array 12 can be known or reliably assumed. Diagnostic catheter 10 also includes a handle 14, and an elongate flexible shaft 16 extending from handle 14. Attached to a distal end of shaft 16 is the electrode array 12, such as a radially expandable and/or compactable assembly. In this embodiment, the electrode array 12 is shown as a basket array, but the electrode array 12 could take other forms in other embodiments. In some embodiments, expandable electrode array 12 can be constructed and arranged as described in reference to applicant's International PCT Patent Application Serial Number PCT/US2013/057579, titled "System and Method for Diagnosing and Treating Heart Tissue," filed Aug. 30, 2013, and International PCT Patent Application Serial Number PCT/US2014/015261, titled "EXPANDABLE CATHETER ASSEMBLY WITH FLEXIBLE PRINTED CIRCUIT BOARD," filed Feb. 7, 2014, the content of which are incorporated herein by reference in their entirety. In other embodiments, expandable electrode array 12 can comprise a balloon, radially deployable arms, spiral array, and/or other expandable and compactible structure (e.g. a resiliently biased structure).

Shaft 16 and expandable electrode array 12 are constructed and arranged to be inserted into a body (e.g. an animal body or a human body, such as the body of Patient P), and advanced through a body vessel, such as a femoral vein and/or other blood vessel. Shaft 16 and electrode array 12 can be constructed and arranged to be inserted through an introducer (not shown), such as when electrode array 12 is in a compacted state, and slidingly advanced through a lumen of the introducer into a body space, such as a chamber of the heart (HC), such as the right atrium or the left atrium, as examples.

Expandable electrode array 12 can comprise multiple splines (e.g. multiple splines resiliently biased in the basket shape shown in FIG. 1), each spline having a plurality of bio-potential electrodes 12a and/or a plurality of ultrasound (US) transducers 12b. Three splines are visible in FIG. 1, but the basket array is not limited to three splines, more or less splines can be included in the basket array. Each electrode 12a can be configured to record a bio-potential (or voltage), such as the voltage determined, e.g., measured or sensed, at a point on a surface of the heart or at a location within a heart chamber HC. Each US transducer 12b can be configured to transmit an ultrasound signal and receive ultrasound reflections to determine the range to a reflecting target, e.g., a point on the surface of a heart chamber (HC), used in the digital model creation of the anatomy.

As a non-limiting example, three electrodes 12a and three US transducers 12b are shown on each spline in this embodiment. However, in other embodiments, the basket array can include more or less electrodes and/or more or less US transducers. Furthermore, the electrodes 12a and transducers 12b can be arranged in pairs. Here, one electrode 12a is paired with one transducer 12b, with multiple electrode-transducer pairs per spline. The inventive concept is not, however, limited to this particular electrode-transducer arrangement. In other embodiments, not all electrodes 12a and transducers 12b need to be arranged in pairs, some could be arranged in pairs while others are not arranged in pairs. Also, in some embodiments, not all splines need to have the same arrangement of electrodes 12a and transducers 12b. Additionally, in some embodiments, electrodes 12a could be arranged on some splines, while transducers 12b could be arranged on other splines.

Catheter 10 can comprise a cable or other conduit, such as cable 18, configured to electrically, optically, and/or electro-optically connect catheter 10 to the cardiac information console 20 via connectors 18a and 20a, respectively. In some embodiments, cable 18 comprises a mechanism selected from the group consisting of: a cable such as a steering cable; a mechanical linkage; a hydraulic tube; a pneumatic tube; and combinations of one or more of these.

The patient interface module 50 can be configured to electrically isolate one or more components of the cardiac information console 20 from patient P (e.g., to prevent undesired delivery of a shock or other undesired electrical energy to patient P). The patient interface module 50 can be integral with cardiac information console 20 and/or it can comprise a separate discrete component (e.g. separate housing), as is shown. The cardiac information console 20 comprises one or more connectors 20b, each comprising a jack, plug, terminal, port, or other custom or standard electrical, optical, and/or mechanical connector. In some embodiments, the connectors 20b are terminated to maintain desirable input impedance over RF frequencies, such as 10 kilohertz to 20 megahertz. In some embodiments, the termination can be achieved by terminating the cable shield with a filter. In some embodiments, the terminating filters can provide high input impedance in one frequency range, for example to minimize leakage at localization frequencies, and low input impedance in a different frequency range, for example to achieve maximum signal integrity at ultrasound frequencies. Similarly, the patient interface module 50 includes one or more connectors 50b. At least one cable 52 connects the patient interface module 50 with the cardiac information console 20, via connectors 20b and 50b.

In this embodiment, the patient interface module 50 includes an isolated localization drive system 54, a set of patch electrodes 56, and one or more reference electrodes 58. The isolated localization drive system 54 isolates localization signals from the rest of system to prevent current leakage, e.g., signal loss—resulting in performance degradation. In some embodiments, the isolation of the localization signals from the remainder of the system comprises a range of impedance greater than 100 kilohms, such as approximately 500 kilohms at the localization frequencies. The isolation of the localization drive system 54 can minimize drift in localization positions and maintain a high degree of isolation between axes. The localization drive system 54 can operate as a current, voltage, magnetic, acoustic, or other type of energy modality drive. The set of patch electrodes 56 and/or one or more reference electrodes 58 can consist of conductive electrodes, magnetic coils, acoustic transducers, and/or other type of transducer or sensor based on the energy modality employed by the localization drive system 54. Additionally, the isolated localization drive system 54 maintains simultaneous output on all axes, e.g., a localization signal is present on each axis electrode pair, while also increasing the effective sampling rate at each electrode position. In some embodiments, the localization sampling rate comprises a rate between 10 kHz and 20 MHz, such as a sampling rate of approximately 625 kHz.

In this embodiment, the set of patch electrodes 56 include three (3) pairs of patch electrodes: an "X" pair having two patch electrodes placed on opposite sides of the ribs (X1, X2); a "Y" pair having one patch electrode placed on the lower back (Y1) and one patch electrode placed on the upper chest (Y2); and a "Z" pair having one patch electrode placed on the upper back (Z1) and one patch electrode placed on the lower abdomen (Z2). The patch electrode 56 pairs can be placed on any orthogonal and/or non-orthogonal sets of axes. In the embodiment of FIG. 1, the placement of electrodes is shown on patient P, where electrodes on the back are shown in dashed lines. (See also FIG. 2)

Figure 2:
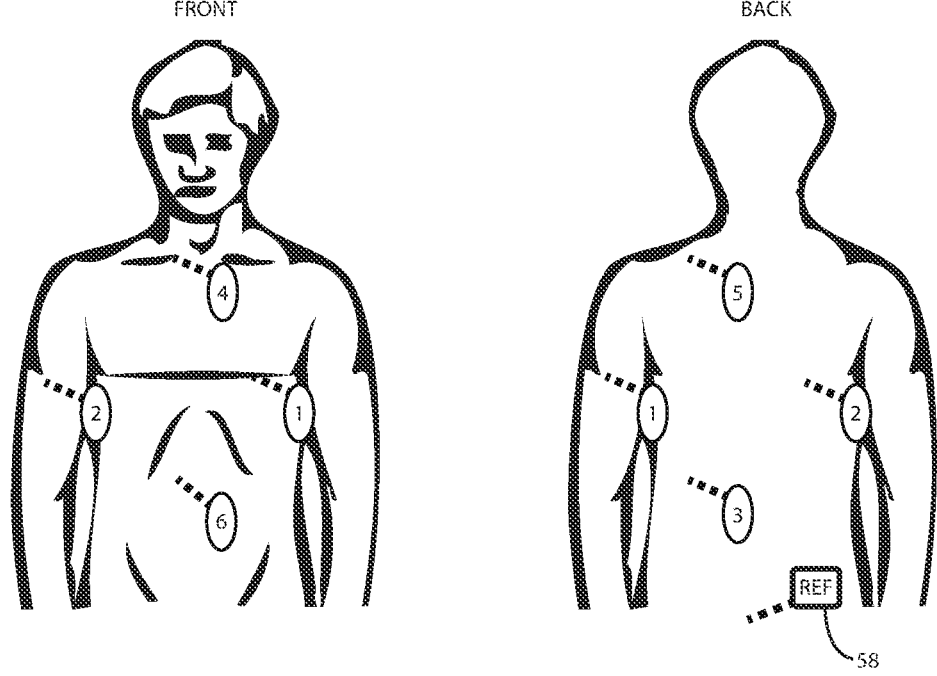
FIG. 2 is a drawing providing a front view and a back view of a patient and relative electrode placement, in accordance with aspects of the inventive concept.

FIG. 2 is a drawing providing a front view and a back view of a patient P and relative electrode placement, in accordance with aspects of the inventive concept. This figure demonstrates a preferred patch electrode placement, as discussed above. In FIG. 1, for example, the X electrodes X1 and X2 are shown as patch electrodes 1 and 2, respectively; the Z electrodes Z1 and Z2 are shown as patch electrodes 3 and 4, respectively; and the Y electrodes Y1 and Y2 are shown as patch electrodes 5 and 6, respectively. Thus, patches 1 and 2 are placed on the ribs, forming the X axis within the body; patches 3 and 4 are placed on the lower back and upper chest (respectively), forming the Z axis; and patches 5 and 6 are placed on the upper back and lower abdomen (torso), respectively, forming the Y Axis. The three axes are of similar length, and not aligned with the "natural" axis of the body (i.e., head to toe, chest to back, and side to side).

The reference patch electrode 58 can be placed on the lower back/buttocks. Additionally, or alternatively, a reference catheter can be placed within a body vessel, such as a blood vessel in and/or proximate the lower back/buttocks.

The placement of electrodes 56 defines a coordinate system made up of three axes, one axis per pair of patch electrodes 56. In some embodiments, e.g., as shown in FIG. 2, the axes are non-orthogonal to a natural axis of the body, i.e., non-orthogonal to head-to-toe, chest-to-back, and side-to-side (i.e., rib-to-rib). The electrodes can be placed such that the axes intersect at an origin, such as an origin located in the heart. For instance, the origin of the three intersecting axes can be centered in an atrial volume. System 100 can be configured to provide an "electrical zero" that is positioned outside of the heart, such as by locating a reference electrode 58 such that the resultant electrical zero is outside of the heart (e.g. to avoid crossing from a positive voltage to a negative voltage at one or more locations being localized).

As described above, a patch pair can operate differentially, i.e. neither patch 56 in a pair operates as a reference electrode, and are both driven by system 100 to generate the electrical field between the two. Alternatively or additionally, one or more of the patch electrodes 56 can serve as the reference electrode 58, such that they operate in a single ended mode. One of any pair of patch electrodes 56 can serve as the reference electrode 58 for that patch pair, forming a single-ended patch pair. One or more patch pairs can be configured to be independently single-ended. One or more of the patch pairs can share a patch as a single-ended reference or can have the reference patches of more than one patch pair electrically connected.

Through processing performed by the cardiac information console 20, the axes can be transformed, e.g., rotated, from a first orientation, e.g., a non-physiological orientation based on the placement of electrodes 56, to a second orientation. The second orientation can comprise a standard Left-Posterior-Superior (LPS) anatomical orientation, i.e., the "x" axis is oriented from right to left of the patient, the "y" axis is oriented from the anterior to posterior of the patient, and the "z" axis is oriented from caudal to cranial of the patient. Placement of patch electrodes 56 and the non-standard axes defined thereby can be selected to provide improved spatial resolution when compared to patch electrode placement resulting in a normal physiological orientation of the resulting axes, e.g. due to preferred tissue characteristics between electrodes 56 in the non-standard orientation. For example, non-standard electrode 56 placement can result in reducing the negative effects of the low-impedance volume of the lungs on the localization field. Furthermore, electrode 56 placement can be selected to create axes which pass through the body of the patient along paths of equivalent, or at least similar, lengths. Axes of similar length will possess more similar energy density per unit distance within the body, yielding a more uniform spatial resolution along such axes. Transforming the non-standard axes into a standard orientation can provide a more straightforward display environment for the user. Once the desired rotation is achieved, each axis can be scaled, i.e., made longer or shorter, as needed. The rotation and scaling are performed based on comparing pre-determined, e.g., expected or known, electrode array 12 shape and relative dimensions, with measured values that correspond to the shape and relative dimensions of the electrode array in the patch electrode established coordinate system. For example, rotation and scaling can be performed to transform a relatively inaccurate, e.g., uncalibrated, representation into a more accurate representation. Shaping and scaling the representation of the electrode array 12 can adjust, align, and/or otherwise improve the orientation and relative sizes of the axes for far more accurate localization.

The electrical reference electrode(s) 58 can be or at least include a patch electrode and/or an electrical reference catheter, which functions as a patient "analog ground" reference. A patch electrode 58 can be placed on the skin, and can act as a return for current for defibrillation (i.e. provide a secondary purpose). An electrical reference catheter can include a unipolar reference electrode used to enhance common mode rejection. The unipolar reference electrode, or other electrodes on a reference catheter, can be used to measure, track, correct, and/or calibrate physiological, mechanical, electrical, and/or computational artifacts in a cardiac signal. In some embodiments, these artifacts can be due to respiration, cardiac motion, and/or artifacts induced by applied signal processing, such as filters. Another form of an electrical reference catheter can be an internal analog reference electrode, which can act as a low noise "analog ground" for all internal catheter electrodes. Each of these types of reference electrodes can be placed in relatively similar locations, such as near the lower back in an internal blood vessel (as a catheter) and/or on the lower back (as a patch). In some embodiments, system 100 comprises a reference catheter 58 including a fixation mechanism (e.g. a user activated fixation mechanism), which can be constructed and arranged to reduce displacement (e.g. accidental or otherwise unintended movement) of one or more electrodes of the reference catheter 58. The fixation mechanism can comprise a mechanism selected from the group consisting of: spiral expander; spherical expander; circumferential expander; axially actuated expander; rotationally actuated expander; and combinations of two or more of these.

In FIG. 1, aspects of the receiver components of the cardiac information console 20 are depicted. The cardiac information console 20 includes a defibrillation (DFIB) protection module 22 connected to connector 20a, which is configured to receive cardiac information from the catheter 10. The DFIB protection module 22 is configured to have a precise clamping voltage and a minimum capacitance. Functionally, the DFIB protection module 22 acts a surge protector, configured to protect the circuitry of console 20 during application of high energy to the patient, such as during defibrillation of the patient (e.g. using a standard defibrillation device).

The DFIB protection module 22 is coupled to three signal paths, a bio-potential (BIO) signal path 30, a localization (LOC) signal path 40, and an ultrasound (US) signal path 60. Generally, the BIO signal path 30 filters noise and preserves the measured bio-potential data, and also enables the bio-potential signals to be read (e.g. successfully recorded) while ablating, which is not the case in other systems. Generally, the LOC signal path 40 allows high voltage inputs, while filtering noise from received localization data. Generally, the US signal path 60 acquires range data from the physical structure of the anatomy using the ultrasound transducers 12b for generation of a 2D or 3D digital model of the heart chamber HC, which can be stored in memory.

The BIO signal path 30 includes an RF filter 31 coupled to the DFIB protection module 22. In this embodiment, the RF filter 31 operates as a low-pass filter having a high input impedance. The high input impedance is preferred in this embodiment because it minimizes the loss of voltage from the source, e.g., catheter 10, thereby better preserving the received signals, e.g., during RF ablation. The RF filter 31 is configured to allow bio-potential signals from the electrodes 12a on catheter 10 to pass through RF filter 31, e.g., passing frequencies less than 500 Hz, such as frequencies in the range of 0.5 Hz to 500 Hz. However, high frequencies, such as high voltage signals used in RF ablation, are filtered out from the bio-potential signal path 30. RF filter 31 can comprise a corner frequency between 10 kHz and 50 kHz, in some embodiments.

A BIO amplifier 32 can comprise a low noise single-ended input amplifier that amplifies the RF filtered signal. A BIO filter 33 (e.g. a low pass filter) filters noise out of the amplified signal. BIO filter 33 can comprise an approximately 3 kHz filter. In some embodiments, BIO filter 33 comprises an approximately 7.5 kHz filter, such as when system 100 is configured to accommodate pacing of the heart (e.g. avoid significant signal loss and/or degradation during pacing of the heart).

BIO filter 33 can include differential amplifier stages used to remove common mode power line signals from the bio-potential data. This differential amplifier can implement a baseline restore function which removes DC offsets and/or low frequency artifacts from the bio-potential signals. In some embodiments, this baseline restore function comprises a programmable filter which can comprise one or more filter stages. In some embodiments, the filter can include a state dependent filter. Characteristics of the state dependent filter can be based on a threshold and/or other level of a parameter (e.g. voltage), with the filter rate varied based on the filter state. Components of the baseline restore function can incorporate noise reduction techniques such as dithering and/or pulse width modulation of the baseline restore voltage. The baseline restore function can also determine, by measurement, feedback, and/or characterization, the filter response of one or more stages. The baseline restore function can also determine and/or discriminate the portions of the signal representing a physiological signal morphology from an artifact of the filter response and computationally restore the original morphology, or a portion thereof. In some embodiments, the restoration of the original morphology can include subtraction of the filter response directly and/or after additional signal processing of the filter response, e.g., via static, temporally-dependent, and/or spatially-dependent weighting, multiplication, filtering, inversion, and combinations of these. In some embodiments, the baseline restore function can be implemented in BIO filter 33, BIO processor 36, or both.

The LOC signal path 40 includes a high voltage buffer 41 coupled to the DFIB protection module 22. In this embodiment, the high voltage buffer 41 is configured to accommodate the relatively high voltages used in treatment techniques, such as RF ablation voltages. For example, the high voltage buffer can have ±100V power-supply rails. In some embodiments, each high voltage buffer 41 has a high input impedance, such as an impedance of 100 kilohms to 10 megohms at the localization frequencies. In some embodiments, all high voltage buffers 41, taken together as a total parallel electrical equivalent, also has a high input impedance, such as an impedance of 100 kilohms to 10 megohms at the localization frequencies. In some embodiments, the high voltage buffer 41 has a bandwidth that maintains good performance over a range of high frequencies, such as frequencies between 100 kilohertz and 10 megahertz, such as frequencies of approximately 2 megahertz. In some embodiments, the high voltage buffer 41 does not include a passive RF filter input stage, such as when the high voltage buffer 41 has a ±100V power-supply. A high frequency bandpass filter 42 can be coupled to the high voltage buffer 41, and can have a passband frequency range of about 20 kHz to 80 kHz for use in localization. In some embodiments, the filter 42 has low noise with unity gain, e.g., a gain of 1 or about 1.

The US signal path 60 comprises an US isolation multiplexer, MUX 61, a US transformer with a Tx/Rx switch, US transformer 62, a US generation and detection module 63, and an US signal processor 66. The US isolation MUX 61 is connected to the DFIB protection module 22, and is used for turning on/off the US transducers 12b, such as in a predetermined order or pattern. The US isolation MUX 61 can be a set of high input impedance switches that, when open, isolate the US system and remaining US signal path elements, decoupling the impedance to ground (through the transducers and the US signal path 60) from the input of the LOC and BIO paths. The US isolation MUX 61 also multiplexes one transmit/receive circuit to one or more multiple transducers 12b on the catheter 10. The US transformer 62 operates in both directions between the US isolation MUX 61 and the US generation and detection module 63. US transformer 62 isolates the patient from the current generated by the US transmit and receive circuitry in module 63 during ultrasound transmission and receiving by the US transducers 12b. The US transformer 62 can be configured to selectively engage the transmit and/or receive electronics of module 63 based on the mode of operation of the transducers 12b, for example by using a transmit/receive switch. That is, in a transmit mode, the module 63 receives a control signal from a US processor 66 (within a data processor 26) that activates the US signal generation and connects an output of the Tx amplifier to US transformer 62. The US transformer 62 couples the signal to the US isolation MUX 61 which selectively activates the US transducers 12b. In a receive mode, the US isolation MUX 61 receives reflection signals from one or more of the transducers 12b, which are passed to the US transformer 62. The US transformer 62 couples signals into receive electronics of the US generation and detection module 63, which in-turn transfers reflection data signals to the US processor 66 for processing and use by the user interface system 27 and display 27a. In some embodiments, processor 66 commands MUX 61 and US transformer 62 to enable transmission and reception of ultrasound to activate one or more of the associated transducers 12b, such as in a predetermined order or pattern. The US processor 66 can include, as examples, detection of a single, first reflection, the detection and identification of multiple reflections from multiple targets, the determination of velocity information from Doppler methods and/or from subsequent pulses, the determination of tissue density information from the amplitude, frequency, and/or phase characteristics the reflected signal, and combinations of one or more of these.

An analog-to-digital converter (ADC) 24 is coupled to the BIO filter 33 of the BIO signal path 30 and to the high frequency filter 42 of the LOC signal path 40. Received by the ADC 24 is a set of individual time-varying analog bio-potential voltage signals, one for each electrode 12a. These bio-potential signals have been differentially referenced to a unipolar electrode for enhanced common mode rejection, filtered, and gain-calibrated on an individual channel-by-channel basis, via BIO signal path 30. Received by the ADC is also a set of individual time-varying analog localization voltage signals for each axis of each patch electrode 56, via LOC signal path 40, which are output to the ADC 24 as a collection of 48 (in this embodiment) localization voltages measured at a single time for the electrodes 12a. The ADC 24 has high oversampling to allow noise shaping and filtering, e.g., with an oversampling rate of about 625 kHz. In some embodiments, sampling is performed at or above the Nyquist frequency of system 100. The ADC 24 is a multi-channel circuit that can combine BIO and LOC signals or keep them separate. In one embodiment, as a multi-channel circuit, the ADC 24 can be configured to accommodate 48 localization electrodes 12a and 32 auxiliary electrodes (e.g., for ablation or other processes), for a total of 80 channels. In other embodiments, more or less channels can be provided. In FIG. 1, for example, almost all of the elements of the cardiac information console 20 can be duplicated for each channel, e.g., except for the UI system 27. For example, the cardiac information console 20 can include a separate ADC for each channel, or an 80 channel ADC. In this embodiment, signal information from the BIO signal path 30 and the LOC signal path 40 are input to and output from the various channels of the ADC 24. Outputs from the channels of the ADC 24 are coupled to either the BIO signal processing module 34 or the LOC signal processing module 44, which pre-process their respective signals for subsequent processing as described herein below. In each case, the preprocessing prepares the received signals for the processing by their respective dedicated processors discussed below. The BIO signal processing module 34 and the LOC signal processing module 44 can be implemented in firmware, in whole or in part, in some embodiments.

The bio-potential signal processing module 34 can provide gain and offset adjustment and/or digital RF filtering having a non-dispersive low pass filter and an intermediate frequency band. The intermediate frequency band can eliminate ablation and localization signals. The bio-potential signal processing module 34 can also include digital bio-potential filtering, which can optimize the output sample rate.

Additionally, the bio-potential signal processing module 34 can also include "pace blanking", which is the blanking of received information during a timeframe when, for example, a physician is "pacing" the heart. Temporary cardiac pacing can be implemented via the insertion or application of intracardiac, intraesophageal, or transcutaneous pacing leads, as examples. The goal in temporary cardiac pacing is to interactively test and/or improve cardiac rhythm and/or hemodynamics. To accomplish the foregoing, active and passive pacing trigger and input algorithmic trigger determinations can be performed, e.g., by system 100. The algorithmic trigger determination can use subsets of channels, edge detection and/or pulse width detection to determine if pacing of the patient has occurred. Optionally, pace blanking can be applied on all channels or subsets of channels, including channels on which detection did not occur.

Pace Blanking

Figure 17A:
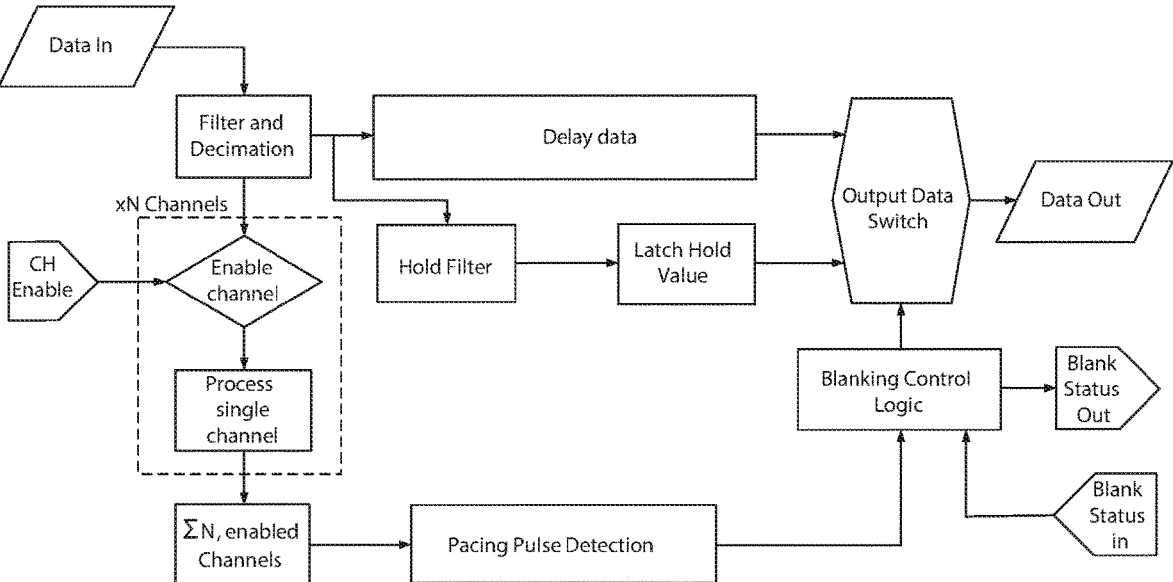
FIGS. 17A-17C diagrams examples of a pace blanking method for one or more channels, in accordance with aspects of the inventive concept.
Figure 17B:
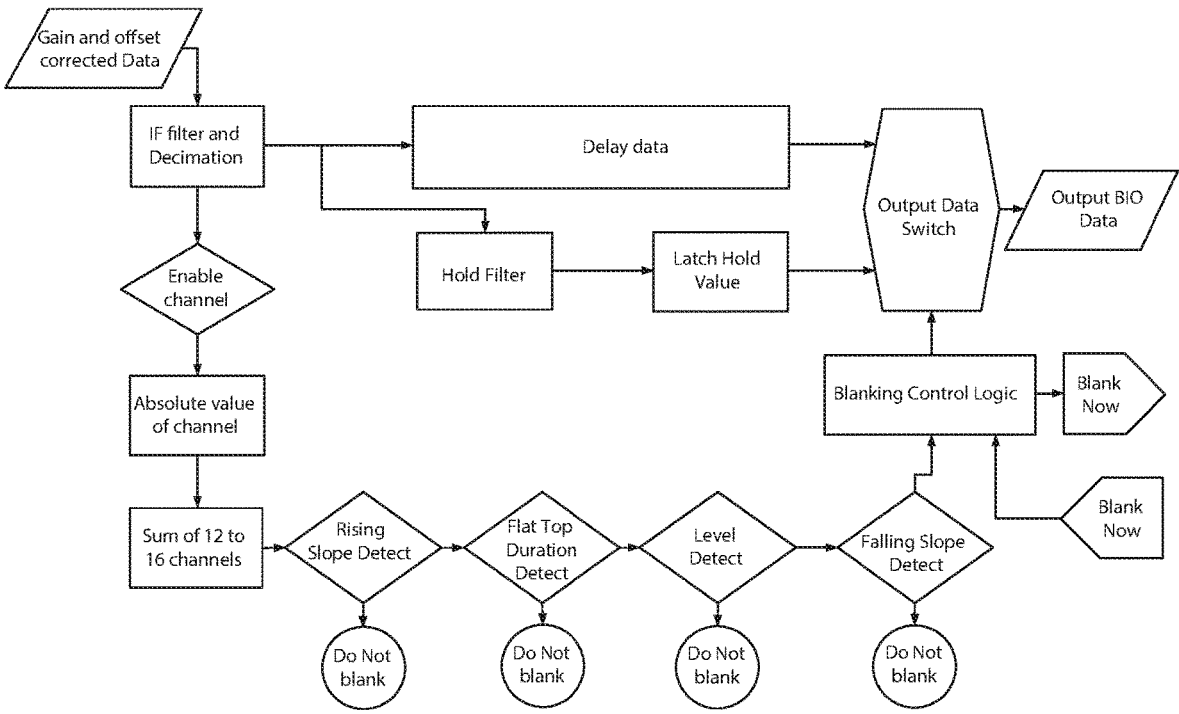
Figure 17C:
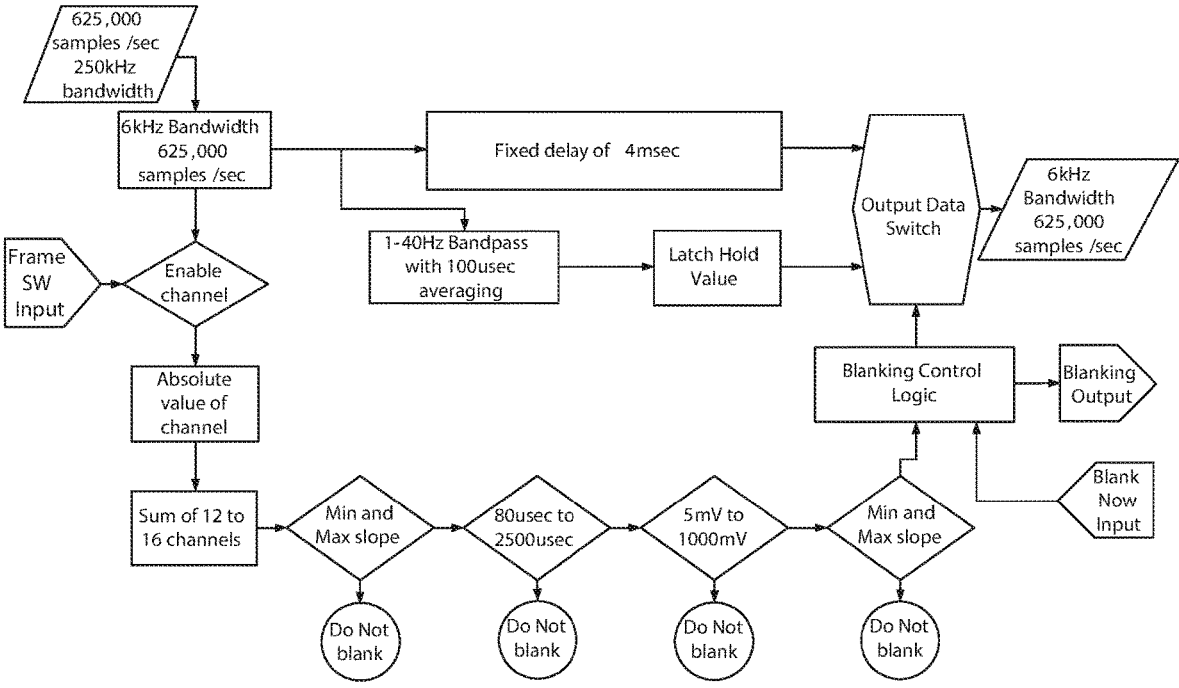

FIG. 17A-17C diagrams a non-limiting example of an embodiment of a pace blanking method for one or more channels. The one or more channels can be grouped for a number of reasons, including, but not limited to, similarity of function, such as surface ECGs, similarity of location, such as channels sharing a physical system board per the system architecture, or convenience. In the figures, the blocks in the dashed box (in FIG. 17A and labeled "xN Channels") operate on individual channels, remaining blocks (FIGS. 17A-C) operate on the group of channels.

The incoming data is, optimally, corrected for channel-specific gain and offset. The input data can also be filtered or decimated at the input, for example, to reduce computational complexity and/or to meet an output data rate requirement. The data stream is then divided into two paths—a delay path and a hold path—converging at an output data switch.

The delay path is delayed by a duration similar or equal to the data width and processing time for the window of data that is processed to detect for a pacing pulse, such as a delay of 0.1-100 ms, such as 0.5-10 ms, such as 4 ms.

The hold path includes a filter and a data latch. The hold filter is configured with a frequency response to exclude variation in the low frequency baseline and higher frequency components of the signal or power line frequencies, such as a bandpass filter with a passband range of 1-40 Hz. The hold filter can also include averaging over a time duration of data to smooth any discontinuous transitions in the output signal of the output data switch, such as a duration between 1 microsecond to 1 sec, such as 10-500 microseconds, such as 100 microseconds. The data latch of the hold path is configured to hold a value of its input for a specified duration or until commanded to release by a control input.

The output data switch is configured to switch its output between the resulting signal from the delay path and the resulting signal of the hold path, based on the configuration determined by the blanking control logic. When the output data switch outputs the hold path signal, the signal is considered to be blanked. When the output data switch outputs the delay path signal, the signal is considered not to be blanked.

The blanking control logic is the end-stage of a pace detection path which uses the input data to determine the presence or lack of a pacing pulse within the current window of input data. For each channel of the group comprising the input data, channels are individually included or excluded from a subset used to detect a pacing pulse. An enable signal for each channel is received from external input and used to include or exclude each channel from the subset. The external input can be determined automatically by the system 100 or configured manually by the user. For each channel that is included in the subset, the signal is processed using a processing algorithm. The processing algorithm can include, but is not limited to, one or more of the following: a filter, a derivative, an integration, a down-sampling, an up-sampling, an absolute value, an averaging, a statistical calculation such as a median, etc.

Each channel of the subset is brought together into a summing node, which operates an algorithm to combine information from all channels of the subset into a representative output. The algorithm used by the summing node can include, but is not limited to, one or more of the following: a sum, an average, a difference, an interleave, etc.

The representative output of the summing node is passed to a pacing pulse detection algorithm. The pacing pulse detection algorithm can include, but is not limited to, one or more of the following: a slope detector, a time-duration measurement, an amplitude detector, a threshold, a derivative, an absolute value, an average, a filter, etc. The sequence of criteria for the pacing pulse detection can be arranged in a logic or decision tree based on the status of each criterion. One or more criteria can be enabled to allow pace blanking, one or more criteria can be enabled to disallow pace blanking, or a combination of these. The result of the pacing pulse detection algorithm is passed to the blanking control logic to control the output of the output data switch.

The blanking control logic includes a communication function to communicate the status of pacing pulse detection between groups of channels. The output status reports to all other groups the presence or lack of a detected pacing pulse for the current channel group. The input status receives the status of one or more other channel groups. The blanking control logic can be configured to incorporate the received status with the result of the pacing pulse detection in the blanking control logic, to overrule the result of the pacing pulse detection, and/or to ignore the received status.

Additionally, the bio-potential signal processing module 34 can also include specialized filters that remove ultrasound signals and/or other unwanted signals, e.g., artifacts, from the bio-potential data. In some embodiments, to perform this filtering, edge detection, threshold detection and/or timing correlations can be used.

The localization signal processing module 44 can provide individual channel/frequency gain calibration, IQ demodulation with tuned demodulation phase, synchronous and continuous demodulation (without MUXing), narrow band R filtering, and/or time filtering (e.g. interleaving, blanking, etc.), as discussed herein below. The localization signal processing module can also include digital localization filtering, which optimizes the output sample rate and/or frequency response.

In this embodiment, the algorithmic computations for the BIO signal path 30, LOC signal path 40, and US signal path 60 are performed in the cardiac information console 20. These algorithmic computations include but are not limited to: processing multiple channels at one time, measuring propagation delays between channels, turning x, y, z data into a spatial distribution of electrode locations, including computing and applying corrections to the collection of positions, combining individual ultrasound distances with electrode locations to calculate detected endocardial surface points, and constructing a surface mesh from the surface points. The number of channels processed by the cardiac information console 20 can be between 1 and 500, such as between 24 and 256, such as 48, 80, or 96 channels.

A data processor 26, which can include one or more of a plurality of types of processing circuits (e.g., a microprocessor) and memory circuitry, executes computer instructions necessary to perform the processing of the pre-processed signals from the BIO signal processing module 34, localization signal processing module 44, and US TX/RX MUX 61. The data processor 26 can be configured to perform calculations, as well as perform data storage and retrieval, necessary to perform the functions of the cardiac information processing system 100.

In this embodiment, data processor 26 includes a bio-potential (BIO) processor 36, a localization (LOC) processor 46, and an ultrasound (US) processor 66. The bio-potential processor 36 can perform processing of recorded, measured, or sensed bio-potentials, e.g., from electrodes 12a. The LOC processor 46 can perform processing of localization signals. And the US processor 66 can perform image processing of the reflected US signals, e.g., from transducers 12b.

The bio-potential processor 36 can be configured to perform various calculations. For example, the BIO processor 36 can include an enhanced common mode rejection filter, which can be bidirectional to minimize distortion and which can be seeded with a common mode signal. The BIO processor 36 can also include an optimized ultrasound rejection filter and be configured for selectable bandwidth filtering. Processing steps for data in signal path 60 can be performed by bio signal processor 34 and/or bio processor 36.

The localization processor 46 can be configured to perform various calculations. As discussed in more detail below, the LOC processor 46 can electronically make (calculate) corrections to an axis based on the known shape of electrode array 12, make corrections to the scaling or skew of one or more axes based on the known shape of the electrode array 12, and perform "fitting" to align measured electrode positions with known possible configurations, which can be optimized with one or more constraints (e.g. physical constraints, such as distance between two electrodes 12a on a single spline, distance between two electrodes 12a on two different splines, maximum distance between two electrodes 12a, minimum distance between two electrodes 12a, and/or minimum and/or maximum curvature of a spline, and the like).

The US processor 66 can be configured to perform various calculations associated with generation of the US signal via the US transducers 12b and processing US signal reflections received by the US transducers 12b. The US processor 66, can be configured to interact with the US signal path 60 to selectively transmit and receive US signals to and from the US transducers 12b. The US transducers 12b can each be put in a transmit mode or a receive mode under control of the US processor 66. The US processor 66 can be configured to construct a 2D and/or 3D image of the heart chamber (HC) within which the electrode array 12 is disposed, using reflected US signals received from the US transducers 12b via the US path 60.

The cardiac information console 20 can also include localization driving circuitry, including a localization signal generator 28 and a localization drive current monitor circuit 29. The localization driving circuitry provides high frequency localization drive signals (e.g., 10 kHz-1 MHz, such as 10 kHz-100 kHz). Localization using drive signals at these high frequencies reduces the cellular response effect on the localization data, e.g., from blood cell deformation, and/or allows higher drive currents, e.g., to achieve a better signal-to-noise ratio. The signal generator 28 produces a high resolution digital synthesis of a drive signal, e.g., sine wave, with ultra-low phase noise timing. The drive current monitoring circuitry provides a high voltage, wide bandwidth current source, which is monitored to measure impedance of the patient P.

The cardiac information console can also include at least one data storage device 25, for storing various types of recorded, measured, sensed, and/or calculated information and data, as well as program code embodying functionality available from the cardiac information console 20.

The cardiac information console 20 can also include a user interface (UI) system 27 configured to output results of the localization, bio-potential, and US processing. The UI system 27 can include at least one display 27a to graphically render such results in 2D, 3D, or a combination thereof. In some embodiments, the display 27a can include two simultaneous views of the 3D results with independently configurable view/camera properties, such as view directions, zoom level, pan position, and object properties, such as color, transparency, brightness, luminance, etc. UI System 27 can include one or more user input components, such as a touch screen, a keyboard and/or a mouse.

Auto-Orientation

As described hereabove, system 100 can use a combination of: voltages measured on electrodes 12a (placed in an intra-cardiac volume such as the left atrium or other chamber of the heart), the measured locations of these electrodes 12a, and an electronic model of the cardiac surface, to create a map. System 100 can include a localization system used to determine the position of the electrodes 12a. Also, signals from ultrasound transducers 12b can be used in combination with the localization information to estimate the cardiac surface (e.g. create the electronic model of the cardiac surface). System 100 can include multiple sets (e.g. three sets) of patch electrodes 56, placed nominally orthogonal to each other to create three localization axes, the X axis (X1-X2), Y axis (Y1-Y2) and Z axis (Z1-Z2) shown in FIG. 1. Each set of patch electrodes 56 comprises a pair of skin electrodes placed across the body. Patch electrodes 56 shown with dotted outlines are positioned on the back of the patient. System 100 can be configured to provide currents (e.g. AC currents) that flow between pairs of patch electrodes 56 through the distributed impedance between them, creating a variable voltage distribution in space (e.g. in the tissue of the patient between the patch electrodes 56). This voltage can vary with time, based on the morphology of the waveform (e.g. an amplitude modulated waveform, a phase modulated waveform, a frequency swept waveform and/or a chirp) applied by system 100. The resultant time-varying signals are synchronously demodulated (in-phase and quadrature) with a fixed phase relationship between the interrogating demodulation signal and the source applied to patch electrodes 56. This demodulation results in a one-to-one correspondence between the three sets of signal measurements (e.g. measured voltages) created by the patches, and their position along the three axes. This configuration allows for localizing the electrodes 12a in space.

The localization coordinate system can be at a different orientation than a standard (normal) physiological orientation, in other words different than anterior-posterior, cranial-caudal and left-right. In some embodiments, system 100 is configured to perform an automated orientation of the localization coordinate system that orients one or more localization axes based on a desired direction. This automated orientation is achieved by comparing the localization voltages measured from electrodes with a known orientation relative to patch electrodes 56 (e.g. ECG electrodes on the body and/or other electrodes of system 100) and information regarding the actual orientation (user-placed) of patch electrodes 56 on the body of the patient. Alternatively or additionally, system 100 can be configured to perform an auto-orientation that rotates the localization coordinate system to match a standard physiological orientation. The ability to deterministically orient (e.g. via a transfer function) the localization coordinate system to match a standard physiological orientation is useful, particularly, when a differential drive localization system is used wherein measured voltages can vary as a function of the location (position) of a reference patch or electrode on or in the body.

System 100 can be configured to orient one or more localization axes in a desired direction according to the following steps:

In a first step, the direction of change in voltage between two or more electrodes placed in a known orientation with respect to the localization axis can be used to establish the desired direction of the localization axis, as defined by each pair of patch electrodes 56.

In some embodiments, ECG leads are placed at various fixed locations on the body with respect to the heart. This placement gives a collection of electrodes in a known orientation with respect to the cardiac chamber, and can be used to establish the directions of the localization axes. In some embodiments, the localization X axis spans the left-right direction of the body, and two ECG leads (e.g. V5 and V6) are positioned to the left of the heart chamber. The voltages from these ECG leads are then compared to the voltage of an electrode from within or nearby the cardiac volume (e.g. an electrode 12a), to establish the direction of the X axis.

Reference electrode 58 can be positioned on the patient's lower back, proximate one of the patch electrodes 56, creating the Y axis (e.g. proximate Y1 shown on FIG. 1). This placement of reference electrode 58 positions the origin of the Y axis on the lower back. The voltage at reference electrode 58 can be set to zero volts (e.g. reference electrode 58 is grounded); and, from comparison to the voltages measured from electrodes placed in the vicinity of the heart (e.g. electrodes 12a and/or other electrodes), the orientation of this localization axis can be established.

In a second step, system 100 can utilize a coordinate system that satisfies the right-hand rule. This utilization provides an additional constraint to establish the orientation of the axes of the localization coordinate system. The currents flowing between the patch electrodes 56 indicate the direction of the patch electrodes 56 orientation, which in-turn establishes the direction of the localization axis. The direction of the current flow can also be established using the direction of change (e.g. a gradient) in voltage. In a three-axis system that injects currents in nominally orthogonal directions, the principal components of the voltage distribution also indicate or approximate the directional orientation of the patches. In some embodiments, the right-handedness condition is used with the estimated direction of the currents from the three axes in the cardiac chamber to fix the direction of the Z axis.

Once a desired orientation of the localization axes (e.g. the axes defined by pairs of patch electrodes 56) is established, system 100 can perform a rotation of the localization coordinate system to a physiological orientation, based on the knowledge of the nominal location of the patch electrodes 56. In some embodiments, the Y-Z plane is rotated by approximately 45° to align with a physiological orientation (e.g. a natural physiological coordinate system).

Dipole Density Algorithm with Increased Speed

In order to obtain a surface distribution of cardiac information (e.g. surface charge density and/or dipole density), system 100 can map the information measured from electrodes 12a to the endocardial surface of the atrium. This mapping can be performed as an inverse problem, and the number of measured points (approximately 48 points from 48 electrodes 12a on the array 12) is much less than the number of points on which a solution is desired to be based (e.g. a solution comprising more than 3000 points on the atrium surface). Inverse problems are ill-posed problems and need special approaches to seek the solution. In some embodiments, system 100 solves the inverse problem using Tikhonov regularization [1] according to the following objective function:

$$\min \|As - \phi\|_2^2 + \lambda^2 \|s\|_2^2 \tag{1}$$

where $$\|As - \phi\|_2^2$$

is the data fitting term, $$\|s\|_2^2$$

is the regularization term, $\lambda$ is the regularization parameter, s is the sources on the surface, $\phi$ is the measured potentials, and A is a m×n matrix where m≪n.

Related to a Singular Value Decomposition (SVD), a singular value decomposition of matrix A is $$A = U\Sigma V \tag{2}$$

where $U \in R^{m \times m}$, $V \in R^{n \times n}$ are singular vector matrices and $\Sigma \in R^{m \times n}$ is a diagonal matrix with diagonal elements as descending singular values. SVD can be used for computation of pseudo-inverse for least-squares solution of linear systems).

Related to a Minimum Norm Estimate (MNE), system 100 can be configured to use SVD of matrix A, such that the regularized solution of the inverse problem defined by equation 1 will be:

$$\hat{s}_{MNE} = V_m \sum_m \left( \sum_m^2 + \lambda^2 I_m \right)^{-1} U^T \phi \qquad (3)$$

where $V_m = V(:,1:m)$, $\Sigma_m = \Sigma(:,1:m)$ contains the first m columns from V and $\Sigma$.

In an early design, system 100 implemented the MNE of equation 3, typically requiring approximately 3000 milliseconds (3 seconds).

Continuous mapping of electrical activity of the heart is achievable due to the following EP-specific improvements in the method of finding the solution of the inverse problem, as described later in this document.

In some embodiments, system 100 is configured to operate more efficiently (e.g. to calculate the solution to an inverse problem in near-real time or real time, "real time" herein), such as by using a truncated SVD computation (e.g. instead of the full SVD computation of above) and/or a CPU-optimized memory allocation algorithm.

System 100 can comprise an inverse solution algorithm comprising C++ codes including the function Calculate TikhonovinverseDouble, as shown in Chart 1. SVD computation is performed with Intel Math Kernel C++ Library (MKL), which is a highly efficient and fast library especially for Intel-based CPUs. Using MKL, all the singular values of matrix $A_{m \times n}$ are computed at each time frame in which bio-potentials are measured by system 100. Later in the algorithm, the number of singular values can be truncated in order to find the solution of equation 3. The interface of the algorithm's C++ function that computes the solution to equation 3 is provided below:

```
DllExport CEDeviceError FastCall
CalculateTikhonovInverseDouble
    (
        double          *targetMatrix,
        int             numberOfRows,
        int             numberOfColumns,
        int             numberOfSingularValue,
        double          lambda,
        ACMMatrix2D<double> *& tikhonovInverse,
        bool            enablePrePostScaling
    )
```

In an early design, system 100 implemented a method for performing SVD computations, as shown in FIG. 1A. In step 152, a full SVD is performed on a matrix:

$$A = U_1 S_1 V_1^T$$

In step 154, a result of the computations performed is combined and also truncated, according to the following equation:

$$A_{Truncated} = U_{1m} S_{1m} V_{1m}^T$$

In step 156, the transpose is computed, represented as:

$$A_{Truncated}^T$$

In step 158, again, another full SVD computation is performed on the result from step 156, according to the following equation:

$$A_{Truncated}^T = U_2 S_2 V_2^T$$

Then, in step 160, a transpose is found, which is represented as:

$$U_2^T$$

The truncated Tikhonov is computed from the result in step 160.

The implementation shown in FIG. 1A, is computationally expensive and there is room for performance improvement. Since equation 3 only needs m number of singular values, there is no need to compute all singular values of A, and the truncated SVD of A can be found directly, in a single step 164 (by using MKL, as shown in FIG. 1B. Therefore, the method of FIG. 1B is significantly more efficient, e.g., less computationally intensive, that the method of FIG. A.

The implementation of FIG. 1B makes several mathematical computations in the previous implementation unnecessary, which enhances the processor performance even further. This improvement includes safe elimination of transposition and extra SVD computation (step 158 of the flowchart in FIG. 1A). In other words, with the new implementation, there is no need for performing transposition and SVD computation twice. In summary, the flowchart shown in FIG. 1A, can be reduced to a single step of directly computing the singular values, as shown in FIG. 1B.

The below code segment represents an approach to performing step 164 of FIG. 1B discussed above:

```
info = LAPACKE_dgesvd(
    LAPACK_ROW_MAJOR,
    'S', 'S',
    n, n,
    inputMatrix->GetMatrix( ),
    Ida, S, U, Idu, V, Idvt, superb);
```

In this above improved SVD implementation, only the singular values that are needed for equation 3 are computed directly.

As described above, early designs implemented the MNE of equation 3, which resulted in approximately 3000 milliseconds in inverse solution computation time. In some embodiments, system 100 includes an algorithm with improved memory allocation, such as is shown in Chart 4. In experimentation, it was found that in the previous algorithm, memory allocation takes 70% of the entire function time, whereas SVD takes about 30%. Due to the size of the matrix for SVD computation, it is possible to efficiently and in a serial manner (rather than using a GPU) perform the computation and eliminate the high cost of memory allocation by using ACMMatrix2D class. For continuous mapping (e.g. changes in dipole density and/or surface charge information shown in real time), system 100 can use MKL memory allocation (i.e. mkl_malloc, which is optimized for Intel CPUs) as shown in Chart 5.

In some embodiments, system 100 includes the improvements described hereabove and achieves approximately 40 times faster performance with the same accuracy (e.g. the computational time for inverse solution will be less than 100 milliseconds, such as approximately 70 milliseconds).

Below is an example of code to provide improved memory allocation for SVD computation, A=UΣV, using the ACMMatrix2D C++ class:

```
if (U != NULL) delete U;
U = new ACMMatrix2D <double>( );
U->SetSize(OnMainMemory,m, m, true);
if (V != NULL) delete V;
V = new ACMMatrix2D <double>( );
V->SetSize(OnMainMemory,n, n, true);
if (S != NULL) delete S;
S = new ACMMatrix2D <double>( );
S->SetSize(OnMainMemory, 1, minDim, true);
```

The below code provides an improved method for efficient memory allocation for SVD computation:

```
void*mkl_malloc (size_t allot size, int alignment);
```

See, as examples, the following references can provide information related to the above approaches for mathematically solving such problems:
1. A. N. Tikhonov and V. Y. Arsenin, "Solutions of Ill-Posed Problems," *Math. Comput.*, vol. 32, pp. 1320-1322, 1978.
2. Intel, "Intel® Math Kernel Library Reference Manual," 2007.

Mapping with Multiple Basket Positions

Some embodiments use a single electrode array 12 (also referred to as "basket" herein) position for computing the transfer matrix in the inverse mapping, which can restrict the length of the mapping segment and the accuracy of the mapping. In other embodiments, every basket position can be used for computing the transfer matrix in the inverse mapping. Using every position of the basket for the transfer matrix can introduce significant computation cost that would slow down the mapping workflow—a subset of those positions for which only a minimal improvement in accuracy can be realized. In another embodiment, the subset of positions for which a substantive improvement in accuracy can be realized can be determined algorithmically—for example, based on the relative change in position of the basket.

Figure 9:
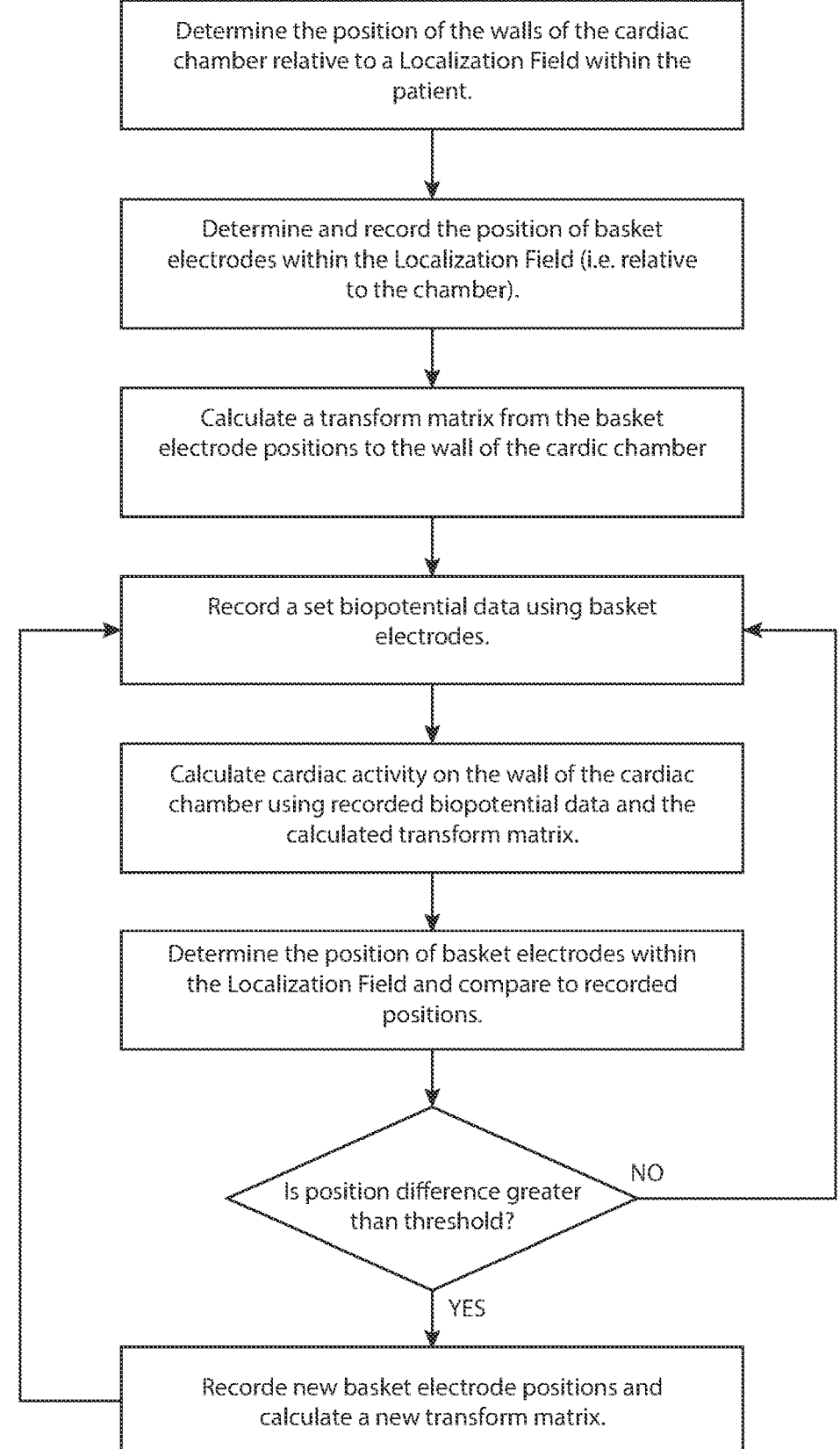
FIG. 9 shows a flow chart for mapping multiple basket positions, in accordance with aspects of the inventive concept.

For multiple basket positions, the current position of the basket is monitored relative to a previous, reference position of the basket, and if the basket changes position past a desired threshold, the position of the basket is updated in the calculations based on the current position of the basket, such as shown in FIG. 9. In one embodiment, the reference position of the basket can be the position in the preceding time sample. In another embodiment, the reference position can be the position at some preceding interval that is updated, dynamically, as the position change exceeds the threshold. In yet another embodiment, the reference position can be the position at some determined point in time, held static throughout the calculation. This algorithm provides accuracy in mapping and at the same time saves processing power, which correlates to faster calculations. Over a 1-5 second recording, there can be 3-4 mm (or more) of uncertainty associated with the position of the basket (which the clinician is generally trying to hold still during recording). In one embodiment, for an input mapping segment, the algorithm uses one position, for example the first position, as the reference position, then checks for a change in the position (e.g. to determine if the reference position should be adjusted). For example, if a 1 mm change in position is detected, that can trigger a position update to the calculations. This process repeats till the end of the mapping segments. The intracardiac electrograms (EGM) and time are aligned with the basket positions so that accurate mapping is calculated in the inverse solution. In another embodiment, the first position can be used as an initial reference position. When the change in position is detected that triggers a position update in the calculations, the reference position is updated. In yet another embodiment, the reference position can be updated continuously, such as when as a new position is acquired and its position is compared to the reference position, the reference position can be updated to be the newly acquired position for the next measurement.

Non-Functional Electrode Detection

System 100 utilizes measured voltages at the location of electrodes 12a (e.g. at least 24 electrodes and/or approximately 48 electrodes in a basket or other array configuration) for the purpose of recording sets of voltages to calculate surface charge density and/or dipole density on an endocardial surface. Unreliable voltage measurements can deleteriously influence any calculation involving localization and/or bio-potential recordings, resulting in poorly localized and/or anomalous cardiac information estimates. For this reason, system 100 can include an automated procedure for identifying any electrode 12a from which anomalous voltage measurements are suspected (a "non-functional" electrode).

System 100 can include the algorithm described below, algorithm NFE, for identification of non-functional electrodes 12a. The NFE algorithm employs three distinct strategies for identifying measured localization potentials which may not accurately reflect the true electrode environment at the time of the measurement. This procedure can be performed during anatomic reconstruction so that each frame (e.g. video frame or other anatomical image, such as a frame representing a time increment of between approximately 25 and 100 milliseconds) of the anatomy recording is associated with a list of electrodes 12a determined to be non-functional during the data collection associated with that frame. Subsequent calculations involving localization or bio-potential recordings can access the stored list of non-functional electrodes 12a, associated with each frame, so that unreliable recordings can be eliminated from critical calculations.

In some embodiments, system 100 comprises a non-functional electrode identifying NFE algorithm that operates (at a minimum) during data recordings made for digital cardiac model creation and/or re-creation ("creation" herein). The NFE algorithm can be configured to process both continuous data and data interleaved with ultrasound data. The NFE algorithm can be configured to assess measured voltages, prior to their association to spatial coordinates. The NFE algorithm can be configured to produce a list of non-functional electrodes 12a that are distinct to each frame containing a list of electrodes 12a from which measured potentials are unreliable.

Figure 3:
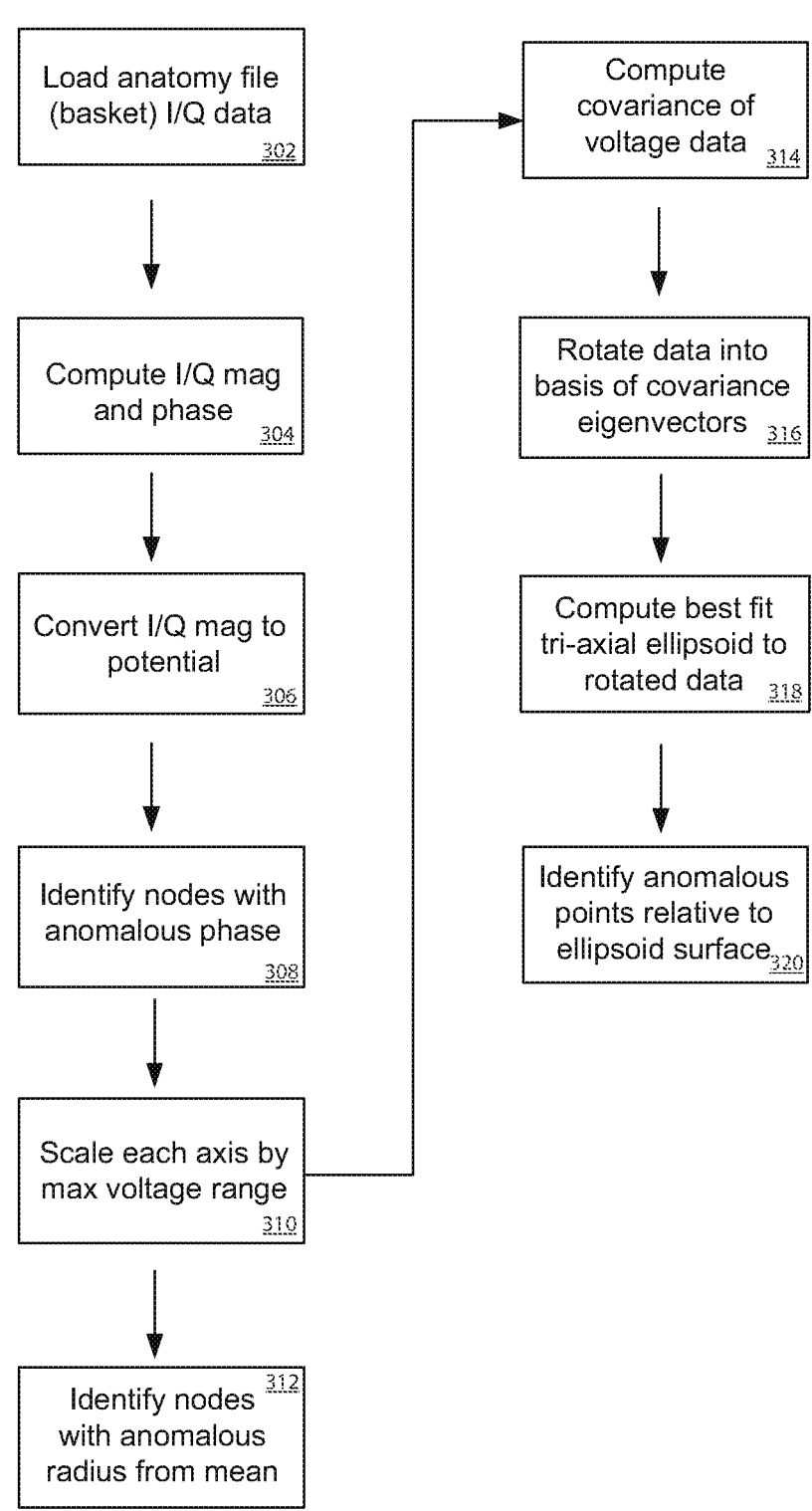
FIG. 3 is a flow chart of identifying non-functional electrodes, in accordance with aspects of the inventive concept.

Referring now to FIG. 3, details of a method 300 comprising a sequence of steps of an NFE algorithm to detect non-functional electrodes 12a is illustrated.

In a first step 302, an anatomy file comprising I/Q data is loaded, e.g., of at least one cardiac chamber. In a second step 304, the system 100 computes I/Q magnitude and phase from the I/Q data. In a third step 306, the I/Q magnitude data is converted to potential data. In step 308, nodes from the anatomy having an anomalous phase are identified. In step 310, each axis is scaled by the maximum voltage range, in view of the potential data. In step 312, nodes having an anomalous radius with respect to a mean are identified. In step 314, covariance of the voltage data are calculated. In step 316, the data is rotated into basis of covariance eigenvectors. In step 318, a best fit tri-axial ellipsoid is computed to the rotated data. In step 320, anomalous points relative to the ellipsoid surface are identified. From this, NFEs can be identified.

More specifically, the NFE algorithm includes various inputs, such as (data and Qdata, each an array of integers of size N by the number of channels (numCH)×3. The first dimension comprises the number of samples, the second dimension comprises the number of channels, and the third dimension comprises the 3 localization axis frequencies. The I/Q data (complex voltages measured at electrodes 12a) can originate from recorded files or from real-time streaming data. Another input can be gain rawdataToVolts, which comprises a float that defines the ADC count to voltage conversion gain of the system 100 hardware. A typical value for gain rawdataToVolt can be 0.52074e-6. Another input can be refnodes aux, an integer array. The contents of the array designate indices of an auxiliary catheter's electrodes that can be used for motion correction.

The non-functional electrode NFE algorithm can comprise one or more outputs. The output of the NFE algorithm can be an array specific to each frame, containing a list of non-functional electrodes 12a from which measured voltage is unreliable. In some embodiments, the user is informed of the list of non-functional electrodes identified. In some embodiments, the user can manually select any electrode 12a for removal, whether or not the electrodes selected are a part of the list of identified non-functional electrodes. In some embodiments, the system 100 allows the user to accept the removal of the identified non-functional electrodes—an opt-in condition. In some embodiments, the system 100 allows the user to accept the removal of a subset of the identified non-functional electrodes—a partial opt-in condition—wherein the subset is determined by user input. In some embodiments, the system 100 recommends a subset of the identified non-functional electrodes 12a for removal, where the subset is determined by an algorithm that identifies electrodes 12a that have been identified as non-functional with a set of temporal conditions, such as the consecutive time duration and/or the duty cycle of functionality over a duration of time. In some embodiments, the list of non-functional electrodes 12a is removed automatically from the display, from subsequent calculations, or a combination of both, by the system 100. In some embodiments, the list of non-functional electrodes 12a is removed automatically by the system 100 from the calculation of a position, orientation, and/or a shape fitting of a device.

In some embodiments, identification of unreliable electrode voltage measurements in each frame occurs through one, two or three distinct procedures, described individually below.

Identify Outliers Based on Anomalies of I/Q Phase

Each electrode 12a can be associated with a magnitude and phase (i.e. the angle in the complex plane subtended by the real and imaginary components of a localization voltage measurement) related to a localization potential on each of the three localization axes. Localization phase can be set (e.g. adjusted) at the start of a procedure (e.g. a clinical procedure or a portion of a clinical procedure) such that all functioning electrodes 12a exhibit a phase close to the set value (e.g. somewhere away from 0 and/or pi). From each electrode 12a's phase values, the mean and standard deviation can be computed. Electrodes 12a which exhibit a phase above a threshold, such as a phase different from the mean by more than a constant multiplied by the standard deviation, are identified as non-functional and loaded into the non-functional electrode list associated with the current frame.

Identify Outliers Based on Potential Relative to Mean

In some embodiments, the voltage of a subset of electrodes 12a which exhibit phase consistent with the selected value is adjusted to zero mean, and the maximum range along each localization axis is computed. Electrode 12a potentials on each localization axis are scaled to the maximum range on that axis, and the radius of the scaled points (relative to the vanishing mean) is computed. Any point exhibiting a radius greater than a threshold, such as a specified constant multiplied by the mean radius, is identified as anomalous and loaded into the non-functional electrode list associated with the current frame.

Identify Points which Deviate from Best Fit Ellipsoidal Surface

The remaining electrodes 12a voltages are again adjusted to zero mean. The covariance of the data array is computed via:

$$C_{ij} = P_{ik} P_{kj}$$

in which the repeated index implies summation over the number of electrodes 12a remaining after elimination of non-functional electrodes 12a identified in either or both steps described immediately hereabove.

The Eigenvectors of the covariance matrix are computed by singular value decomposition:

$$C = U \, S \, V^t$$

in which the columns of the square array U are the desired Eigenvectors.

Voltage data is transformed into the basis of Eigenvectors:

$$P'_k = U_{kl} P_l$$

in which $P_l$ is the 3-D potential associated with a particular electrode 12a.

With scaled voltage represented relative to an orthogonal basis, the data are fitted to a generalized tri-axial ellipsoid with semi-major axes aligned with the basis vectors:

$$\frac{p_x^2}{a^2} + \frac{p_y^2}{b^2} + \frac{p_z^2}{a^2} = 1$$

with a, b, and c being the semi-major axes along the three coordinate directions respectively. The fit can be executed by an explicit LLS method or by computation of the pseudo-inverse using singular value decomposition (SVD).

With the semi-major axes defined, each set of three potentials associated with a particular electrode k can be assigned an error:

$$\varepsilon_k = abs \left[ \frac{p_{k,x}^2}{a^2} + \frac{p_{k,y}^2}{b^2} + \frac{p_{k,z}^2}{c^2} - 1 \right]$$

The mean error is computed, and any point exhibiting error greater than a threshold, such as a specified constant multiplied by the mean error, is identified as a non-functional electrode and loaded into the non-functional electrode list associated with the current frame.

The concatenation of non-functional electrodes 12a identified by one or more (e.g. all) of the three steps above comprises the list of non-functional electrodes 12a associated with the current frame which exhibit voltages deemed unreliable for inclusion in either field estimation (e.g. for localization) or cardiac information (e.g. dipole density and/or surface charge density) calculation.

Recursive Identification

Following identification of non-functional electrodes or "bad" electrodes (w.r.t. localization potential) and computation of the local field estimate/scale matrix, localization of all electrodes 12a (including those Identified as non-functional) and alignment with the standard basket definition (e.g. geometry of the array of electrodes 12a) allows subsequent assessment of electrode separation from the corresponding 'standard' location. Electrodes 12a identified as non-functional can in fact still localize close to the corresponding 'standard' position. Such "good" electrodes 12a can be removed from the list of non-functional electrodes 12a in order to provide the largest number of electrodes for computation of, for example, field estimates and/or auxiliary electrode localization.

FIG. 10 is a flow chart showing one example of the steps to reclassify non-functional electrodes or "bad" electrodes for use in calculating cardiac activity. Step 1 includes Recording Localization and Biopotential data using a multi electrode catheter, such as catheter 10. Step 2 filters the data for non-functional electrodes or "bad" electrodes, using the criteria discussed above (first criteria) for determination of good/bad. In some embodiments, the first criteria is biased towards identifying an electrode as bad. Step 3 then filters the identified non-functional electrodes or "bad" electrodes using 2nd criteria to determine if any "bad" electrodes can be reclassified "good" again. In some embodiments, the 2nd criteria is biased towards identifying an electrode as bad. If some of the non-functional electrodes or "bad" electrodes are reclassified as "good", the cardiac activity data is then calculated using data from final set of "good" electrodes. In one embodiment, the Step 3 that filters the identified non-functional electrodes to be reclassified "good" again can be performed by a) replacing a test subset (one or more) of the identified non-functional electrodes into the "good" classification, b) determining the contribution of the electrodes in the test subset to the error in the basket position, c) repeating steps (a) and (b) through all (or a subset of) permutations/ combinations of electrodes included in the test subset. The repeating can be performed, for example, by a recursive method. The final set of electrodes returned to the "good" classification can be determined by a comparative method, for example, the largest test subset with a total error contribution below a threshold or the test subset with the lowest error contribution among all tested subsets. The determining of the contribution of the electrodes in the test subset to the error in the basket position can be performed, for example, by quantifying the change in the basket position with and without the electrodes in the test subset as a translation, rotation, a general affine transformation, or the sum, mean, and/or RMS of pair-wise distances between the matching electrodes in both basket positions (e.g. array of electrode 12a positions). The basket positions for which error is determined can be the raw, localized electrode positions or the electrode positions from a geometric fit, such as an SVD fit.

ADC Card On/Off

In some embodiments, system 100 comprises a subsystem which turns off ADC 24 under certain conditions, such as to improve efficiency of the system or to reset the data stream to clear a data repository, such as a buffer, filter, or memory. For example, system 100 can be configured to turn off ADC 24 to decrease load, thereby decreasing the amount of data throughput into processor 26 or other component of system 100. In some embodiments, system 100 is configured to turn off ADC 24 when calculating an inverse solution to determine dipole density and/or surface charge density from voltage data. In some embodiments, system 100 is configured to turn off ADC 24 whenever exiting an acquisition mode, such as a mode in which data is collected (e.g. actively collected) from electrodes 12a and/or ultrasound transducers 12b. System 100 can be configured to turn off ADC 24 automatically, based on user input, or a combination of these. In some embodiments, system 100 is configured to turn off ADC 24 and, after a period of time, turn on ADC 24 automatically, as a reset function. The reset can be automatic based on time (periodic), automatic based on a detected input (triggered), or manual based on user input. In some embodiments, processes in parallel or in series to ADC 24, such as filtering, buffering, blanking algorithms, interleaving, etc. can be configured to be disabled in an appropriate sequence to minimize artifacts resulting from the transient state change of ADC 24, such as turning on from an off state, or turning off from an on state. In some embodiments, after ADC 24 has been reset, the processes disabled to minimize artifacts can be automatically returned to their operating state prior to the ADC 24 reset.

V-Wave Removal (VWR)

System 100 can be configured to at least partially remove ventricular far field signals (V-waves) that may be imposed on an atrial signal of interest (e.g. to assess an arrhythmia such as atrial flutter and/or atrial fibrillation). For example, system 100 can comprise an algorithm, VWR algorithm, configured to identify and remove components of the intracardiac electrograms (EGM) due to ventricular activation. The VWR algorithm can employ a process which analyzes recordings from electrodes 12a and a user's input. The ventricular far field signals (V-waves) can be subtracted significantly from the EGM while the atrial activities are well preserved.

The VWR algorithm can operate (e.g. at a minimum) on recorded data after at least some signal filtering. The VWR algorithm can assume the user selected proper segment(s) on the EGM that correspond to a V-wave. The VWR algorithm can assume that the V-wave is consistent through the recording.

Referring to FIG. 4, a block diagram is illustrated that details the overall sequence of steps of a method 400 required for the V-Wave Removal (VWR) algorithm.

The VWR algorithm can comprise one or more inputs. An input of the VWR algorithm can comprise an EGM of a data recording, such as an EGM that includes both atrial activity and ventricular components. An input of the VWR algorithm can comprise Start and End sample numbers, which can represent one ventricular segment and can define a user selected ventricular example for the V-wave in the EGM.

The VWR algorithm can comprise one or more outputs. An output of the VWR algorithm can comprise estimated V-components in the input EGM. An output of the VWR algorithm can comprise an EGM with a V-wave subtracted.

The V-Wave Removal (VWR) algorithm can be configured as a filter or pseudo-filter ("filter" herein) and/or comprise a filter. The start and end sample points can be the input parameters for this filter. The filter can be used to remove the ventricular components in the EGM.

In some embodiments, VWR algorithm comprises three steps: 1) automatic identification of a V-wave segment, steps

402 and 404; 2) creation of a V-wave template (e.g. a channel-specific V-wave template), steps 406 and 408; and 3) subtraction of V-wave from the EGM, and smoothing of the boundary, step 410.

For example, referring to FIG. 4, in a first step 402, the system (e.g., processor 10) automatically select peaks as fiducial time points and segment intervals. In step 404, the system calculates a cross-correlation value ("cc value") between sample V segment and selected V segments is calculated, V segments with cc<0.9 are rejected. In step 406, all V segments averaged to generate V template. In step 408, the system aligns the V template and adjusts time shifts according to time lags. And in step 410, the system smooths the boundaries of V template to create smooth transactions and avoid sudden jumps.

In some template based V-wave removal algorithms for intracardiac electrograms (EGM), large atrial signals with amplitudes comparable to ventricular signals can result in the detection of some atrial signals as ventricular segments, which could lead to the removal or alteration of atrial signals desired for mapping. By using a simultaneous recording of EGM and ECG, ventricular timings from surface ECG channels by peak detection can be identified. ECG channels can be preferred as a secondary reference for the selection of ventricular timing due to the smaller proportional amplitude of atrial to ventricular signals, typically seen in ECGs as compared to intracardiac EGMs. Peaks detected from ECG channels are then used as a timing reference to retain timings from EGM (e.g. timing differences<=50 ms). Timings associated to ventricle activities are then retained and timings associated to atrial activities are then removed from further ventricle template generation and subtraction.

Figure 11A:
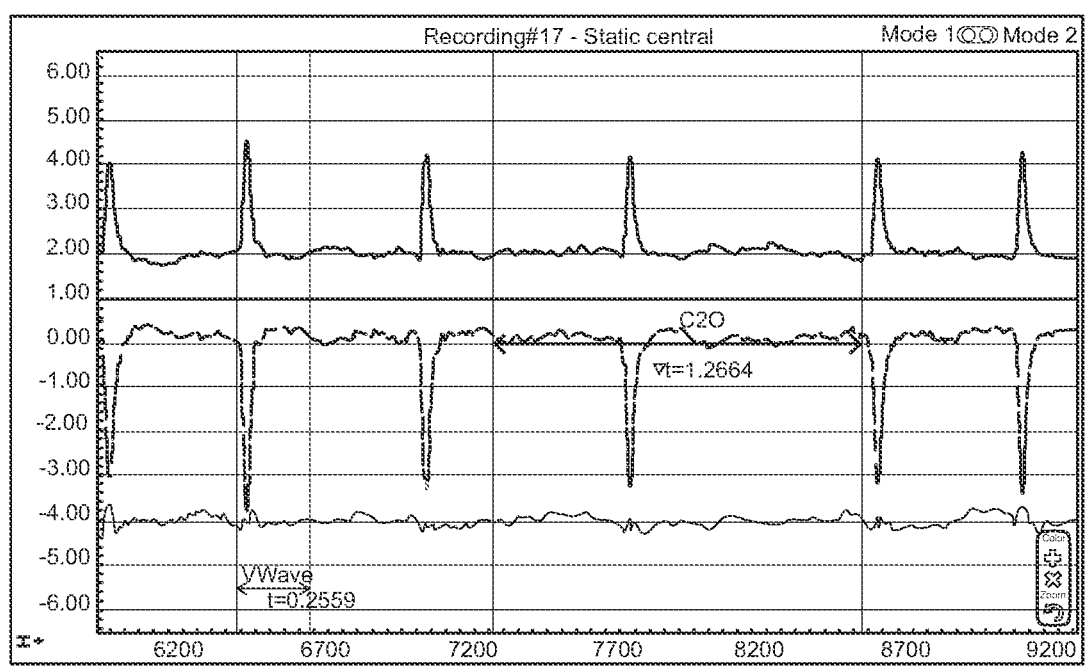
FIGS. 11A and 11B show two examples of V-Wave Removal (VWR).
Figure 11B:
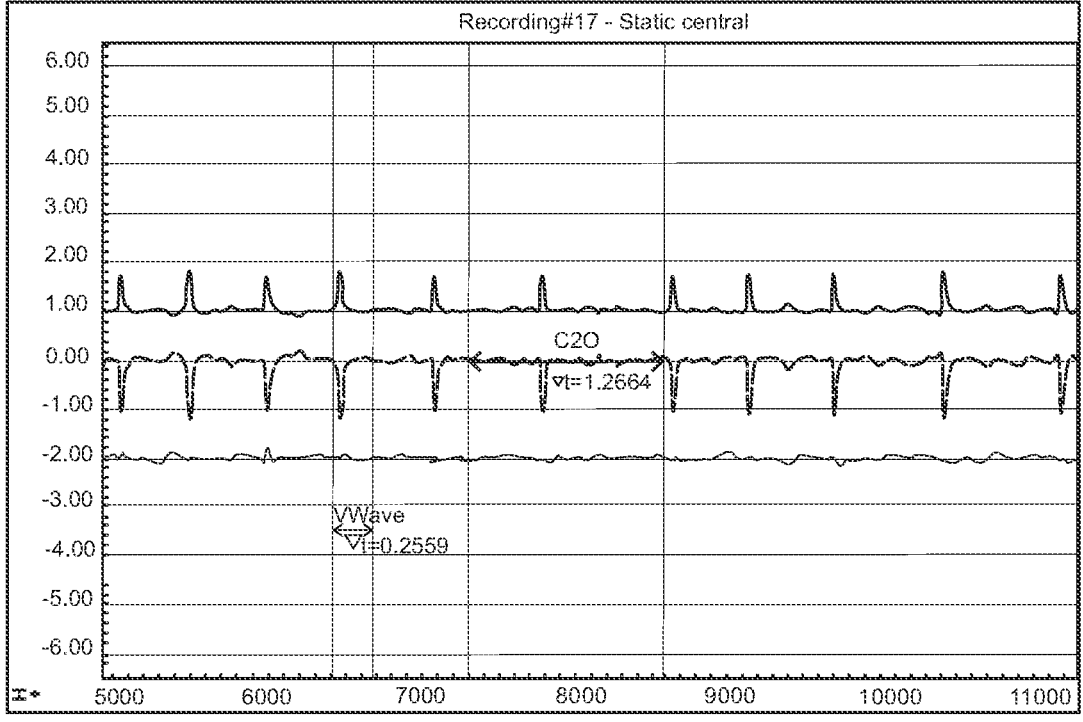

FIGS. 11A and 11B show two examples of V-Wave Removal (VWR). In each figure, the top trace is collected from an ECG lead showing the large atrial signals, the middle trace is an electrogram of system 100, the bottom trace is the V-wave removed electrogram. In these examples, the V-wave and the high pass filter artifact following have been selected for removal.

V-Wave Segment Identification

In order to remove the V-Wave signal from the EGM, an initial step is to identify the segment that includes the V-Wave component(s). As the V-Wave measured on the bio-potential channels (e.g. voltage measurements on electrodes 12a) has consistent waveform and amplitude, a BCT voltage (estimated voltage at geometric center of array of electrodes 12a) can be calculated by averaging all the channels at each time point. The peaks in the BCT then can be used as fiducial time points of a V-Wave.

The user specified V-wave sample can then be used to find a V-wave segment. The peaks in the V-wave samples can be aligned with the fiducial time points. The maximum cross-correlation between the V-wave sample and the segment at the fiducial point can be calculated. The initial alignment can then be adjusted according to the time lag generated from the maximum cross-correlation. The aligned segments in the EGM can then be marked as the V-wave segments.

Create Channel Specific V-Wave Template

Once the V-Segments are identified in each of 48 channels, the channel specified V-wave template can be created by aligning the V-segment(s) within that channel, and taking the average of them. The plots "A" in FIG. 4A show an example of the V-wave template for a single channel.

Figure 4A:
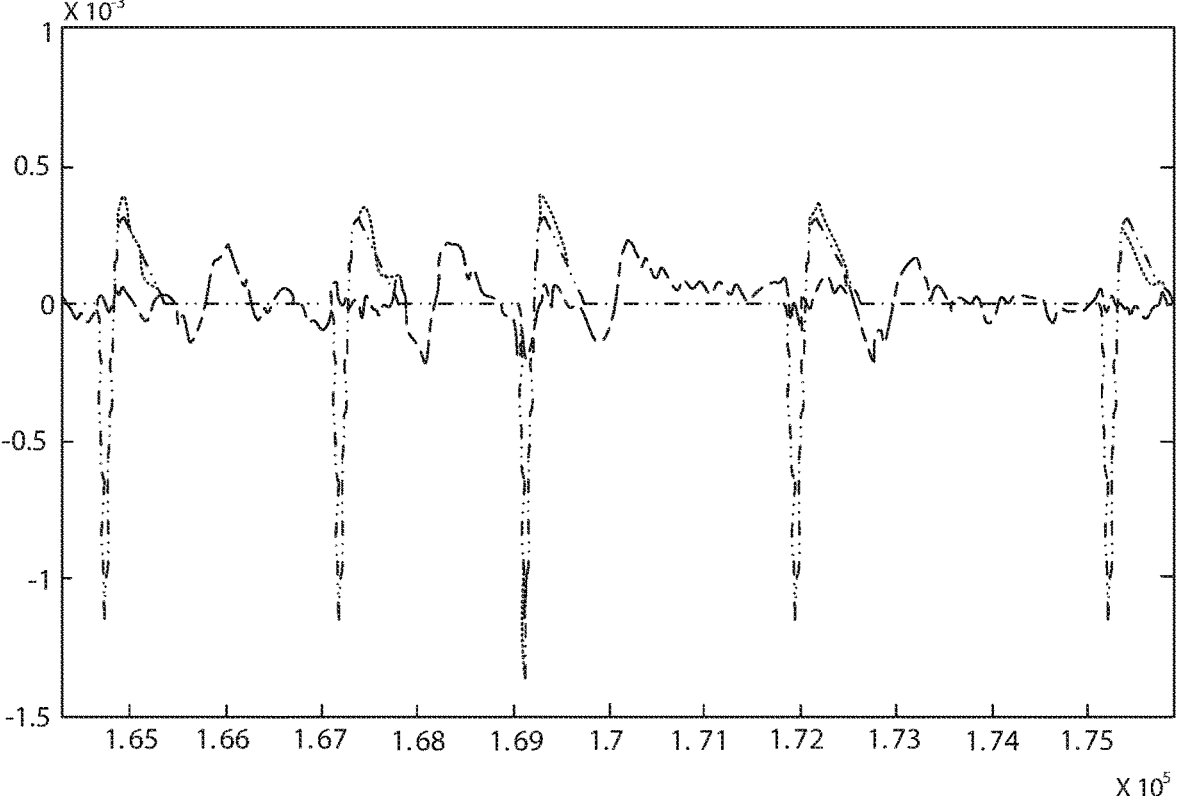
FIGS. 4A through 4C show various example of V-wave removal plots, in accordance with aspects of the inventive concept.
Figure 4B:
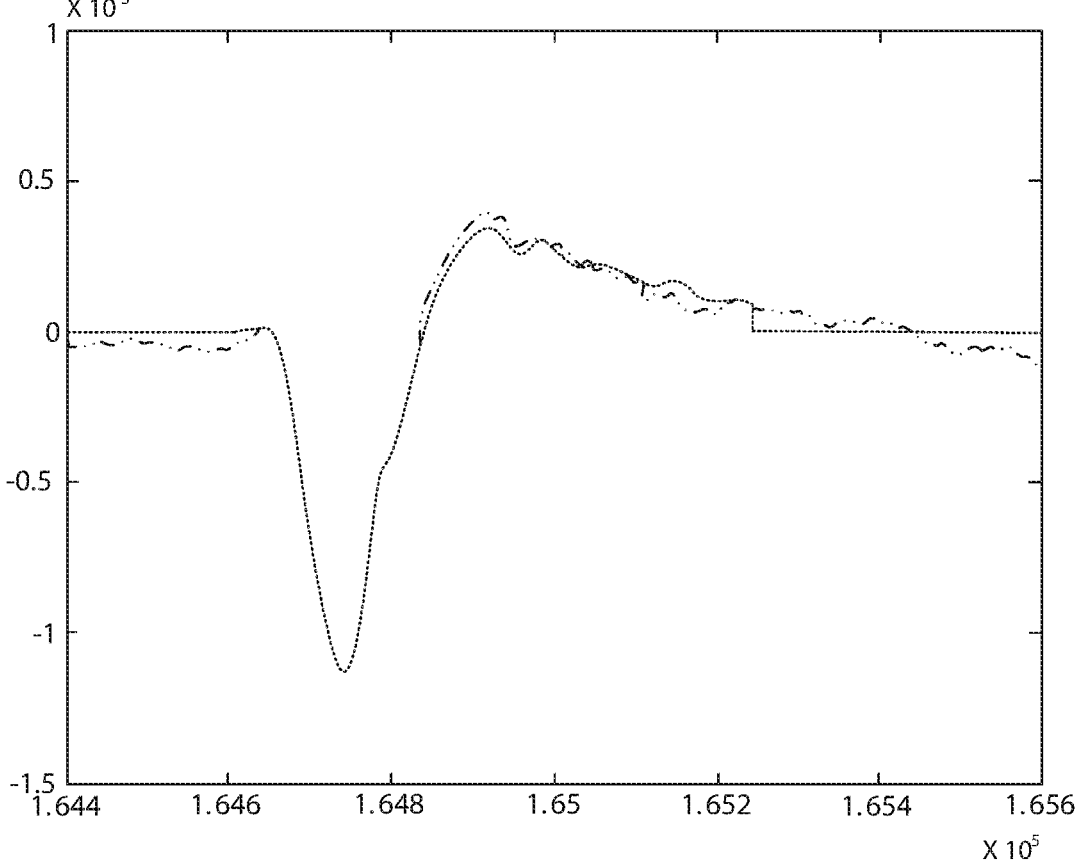

The plot "B" in FIG. 4A illustrates one example of the EGM after removing the V-wave. The ventricular far field signal is reduced up to 80%. The atrial activities and baseline are preserved.

Subtract V-Wave and Smooth Out the Boundary

Figure 4C:
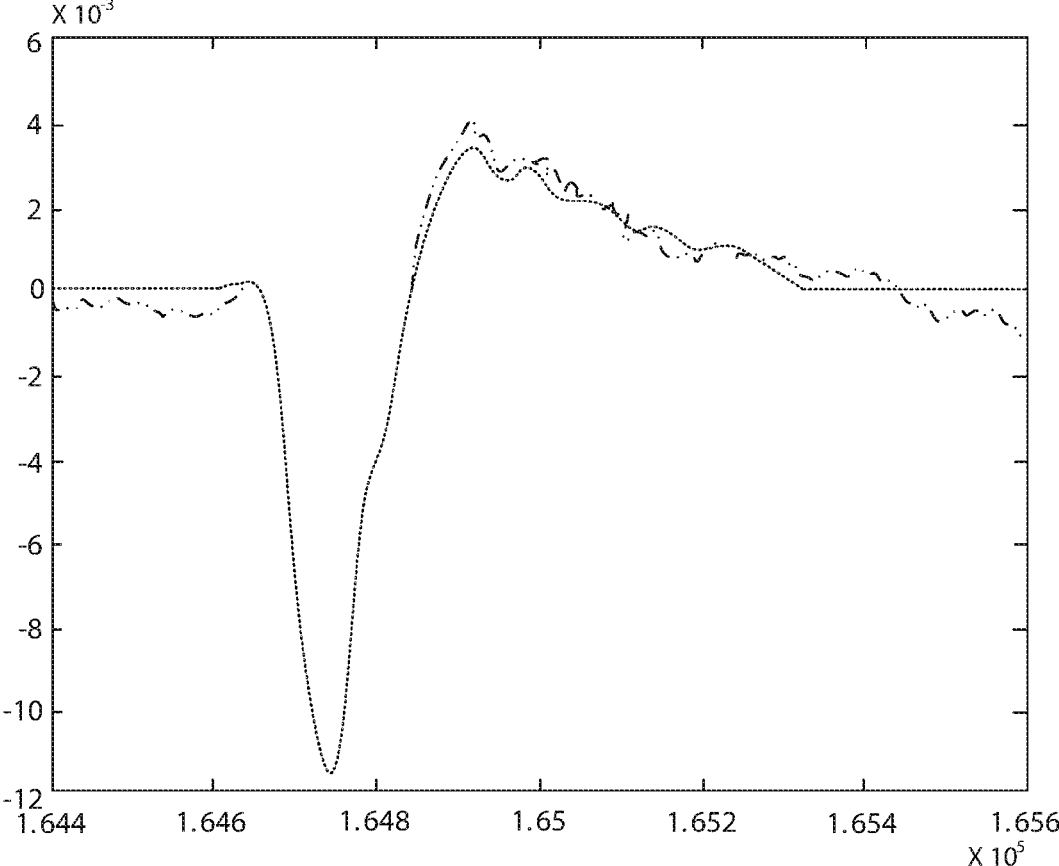

Once the channel specified V-wave template is created, data from the V-wave template is subtracted from the V-wave segment in the EGM. However, at the start and end point of the V-wave template, there can be "jumps" in the signal from the V-segment. See FIG. 4B for an example of this phenomenon. A Hanning window can be used to smooth the boundary, such as is shown in FIG. 4C.

V-Wave Blanking or Zeroing

In other embodiments, blanking or zeroing of the V-wave in the EGM can be used in place of the subtraction of the V-wave, such that any ventricular contribution is removed from the signal, accepting a concurrent loss of atrial signal. In some embodiments, the segment of the signal containing the V-wave data can be manually selected (e.g. a selection made using on-screen "calipers"), and/or selected using a template based detection method (e.g. system 100 automatically detects the V-wave using a signal template). The segment can be blanked or "zeroed" by setting all values in the segment to a set value (e.g. zero) and/or via an interpolation across the segment duration (e.g. linear interpolation between the data values just prior to and just after the selected time segment) Smoothing of the boundary at or near the beginning and end samples of the segment can be used to minimize transition artifacts from interaction with other filters.

V-Wave Blanking or Zeroing with Reduced Baseline Offset

In some embodiments, blanking or zeroing of the V-wave in the EGM is performed using the raw signal (e.g. prior to the application of filters, such as a high pass filter (HPF)). As described hereabove, V-wave zeroing performed after the application of a HPF can result in an offset of the atrial baseline and/or morphology-like artifact due to the inclusion of large and imbalanced signals (e.g. V-waves) in the HPF processing.

Alternatively, V-wave zeroing performed prior to the application of a HPF can prevent an offset of the atrial baseline by removing the large and imbalanced signals (e.g. V-waves) prior to the application and processing of a HPF. In some embodiments, interpolation of V-wave zeroing prior to the application of a HPF matches the slope and curvature of any low-frequency components (e.g. respiration or drift).

Activation Detection for Propagation History Maps

Figure 12:
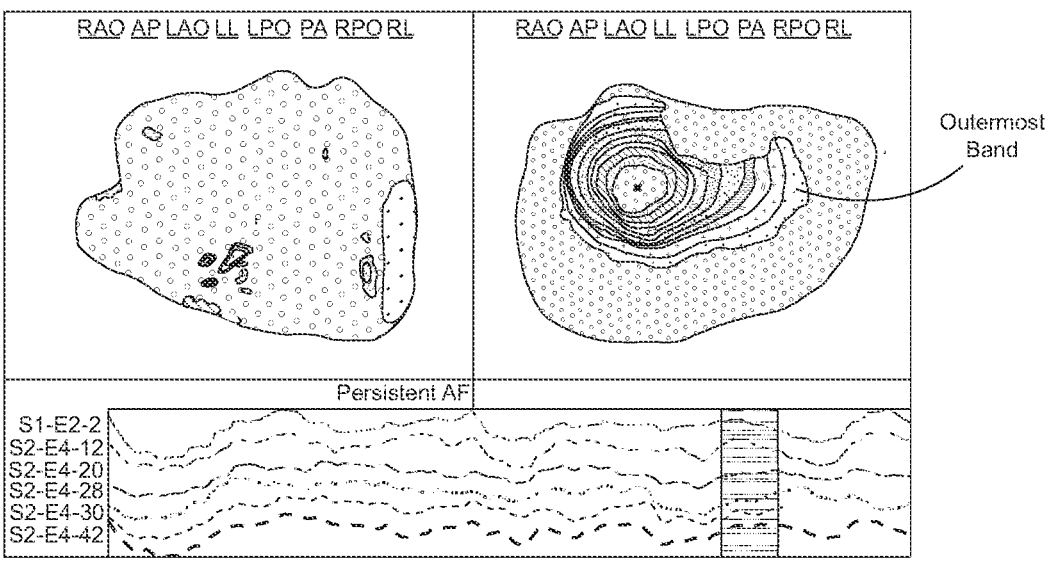
FIG. 12 is an embodiment of a display of views of cardiac activation data, in accordance with aspects of the inventive concept.

FIG. 12 is an embodiment of a display of views of cardiac activation data. In the right-side view, the heart is shown from a first perspective with various bands of activation shown. The outermost band is the activated node band. The subsequent bands represent recently activated states. The activation status relates to the time indicated by the sliding window overlaid on the EGM, which has a horizontal time axis. The width of the sliding window reflects the 50 ms window width, referred to as "Propagation History". In the left side view, a different perspective of the same heart is shown. This view shows that the activation wave has propagated around the heart. Various user-interactive devices can be provided in the display for manipulating the 3D images of the heart, e.g., rotating the images, adding labels to the images, and so on.

In various embodiments, the cardiac information dynamic display system can include video display control tools that enable a user to play, replay, rewind, fast forward, pause, and/or control the playback speed of the dynamic activation wave propagating over the heart.

Automatic annotation of the activation time is essential for creating a propagation history map. However, noise in the virtual EGM can introduce artifacts in the propagation history maps which not only causes visual noise, but also results in less accurate activation detection.

Median Filter for Propagation History Maps

A median filter can be applied to the propagation history maps. For each node in the cardiac anatomy, the propagation history value is updated to the median of the original propagation history values of the node and of its neighboring nodes. These neighboring nodes are defined as nodes within a certain distance of the node being updated. As this distance increases, there is more noise removal, but less local propagation history detail. For further filtering the median filter can be applied multiple times to a propagation history map.

One rationale for using a median filter to post process the propagation history is that the propagation history map can be considered a series of images. The noise in the propagation history is most similar to "salt and pepper noise" which is commonly referred to in image processing. Salt and pepper noise is difficult to remove with traditional low pass filters (blurring filters) without causing other artifacts such as distorted boundaries in images. A median filter can remove salt and pepper noise while maintaining sharp boundaries (see FIG. 13).

Figure 13:
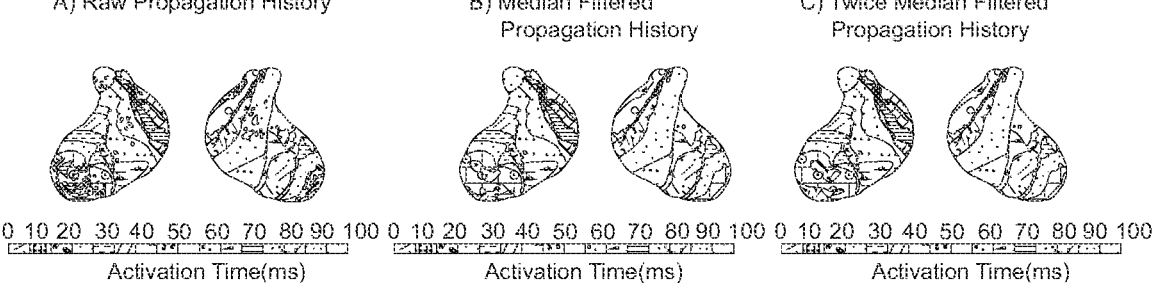
FIG. 13 shows some examples of median filter applied to propagation history maps, in accordance with aspects of the inventive concept.

FIG. 13 shows some examples of a median filter applied to propagation history maps. A) Raw frame of a propagation history map. B) A median filter has been applied to the propagation history in A), such that many artifacts are reduced as compared with A). C) A second median filter is applied to the image in B), resulting in fewer artifacts as compared with A) and C).

False Positive Activation Removal

Automatic annotation of the activation time is essential for creating a propagation history map. However, noise in the virtual EGM can introduce false activation which can lead to incorrect interpretation of the propagation history map.

In some embodiments, an algorithm is used to detect the noise from true activation by checking the amplitude of the electrogram in a time window around potential activations. If the electrogram passes an amplitude threshold, the potential activation is called a true activation. This size of the time window around potential activations acts not only as a strict amplitude threshold but also acts as a minimum slope threshold. Larger time windows allow for lower sloped activations (such as those found in slow depolarizing tissue) to be shown, whereas smaller time windows around an activation will find faster depolarized tissue regions.

FIG. 14 shows one example implementation of false positive activation annotations removal. A) Originally detected activations shown in green. B) Example of false positive removal from activation circled in A). Within time window the amplitude of the electrogram is checked. Since this activation does not meet amplitude threshold, it is removed in C). C) automatically detected activations after false positive removal. Activation that are of low amplitude/slope from A) are removed.

Registration Handling

In some embodiments, system 100 comprises a registration handling subsystem (e.g. algorithm) to correlate electric field measurements (voltage measurements) to locations, and to maintain coordinate registration between the localized intracardiac devices and the reconstructed cardiac surface displayed on the UI throughout a procedure, accommodating changing conditions, both intended and unintended, such as: loss of power, system hardware or software restart, variation in the localization source output, and/or variation in the localization field distribution within the body. The localization subsystem of system 100 serves an important role in the acquisition and analysis of cardiac information, such as to guide ablation catheters and/or provide accurate position information for mapping and other sensing catheters. The final step of localization is to calculate coordinates of electrodes or other catheter components from its localization voltage reading. The input and output are defined below:

Catheter Component Coordinates$_{(X,\ Y,\ Z)}$>=F(Catheter Localization Voltage ($V_x$, $V_y$, $V_z$)), where F is the function mapping from voltage space to coordinate space.

Mapping function F (registration) between voltage space and coordinate space is defined by the following factors:

1. The localization subsystem, for example as described in applicant's co-pending United States Provisional application Ser. No. 62,161,213, Localization System and Method Useful in the Acquisition and Analysis of Cardiac Information, filed May 13, 2015, the content of which is incorporated herein in its entirety for all purposes,
2. The patient.

Since function F differs under different conditions (e.g. different reference electrode 56 positions, different patient anatomy, and the like), it cannot be a static portion of system 100. As a result, the function F has to be determined dynamically, and saved properly to facilitate patient treatment and potentially post-procedural analysis.

In some embodiments, voltage-to-position mapping function F is configured as follows.

1. Function F contains information to convert voltage to coordinates, including but not limited to:
a. Catheters in use (e.g. type or model), a system input channel list and a list of excluded channels (e.g. channels with non-functional electrodes 12a as described herein).
b. Scaling transform between voltage and coordinates.
c. Optionally, positional or coordinate reference(s) measured or calculated from a set of system input channels (e.g. electrodes, patches, etc.), including a system input channel list, list of excluded channels and original or initial voltage.
2. Repository for Registration data.
a. Primary copy of Registration data is saved with a corresponding anatomical 3D model.
b. Secondary copy of Registration data is saved with each recording, which contains:
i. The contents from primary copy.
ii. Updates after the primary copy was taken, such as different excluded channels for catheters and positional reference information.
3. Registration Search Path When registration data is required for calculation, either for post-analysis or guiding ablation catheters in real time, a cardiac information algorithm (e.g. dipole density and/or surface charge density algorithm as described herein) will search for proper registration following the path below:

Secondary Copy

If no corresponding secondary copy is found, search for primary copy.

If no primary copy is found, display a warning message to user and use a default configuration.

4. Alignment of Independent Registration Configurations

When an independent primary configuration and an independent secondary configuration are mismatched, such as when an improper anatomy is assigned to an analysis recording, the cardiac information algorithm will perform a registration correction to align the secondary configuration with the primary configuration, or vice versa, such that the resulting coordinate systems for both configurations are unified and can be used in the same coordinate space.

5. Detection and Correction of Registration Changes

Under changing conditions such as such as loss of power, system hardware or software restart, variation in the localization source output, and/or variation in the localization field distribution within the body, the registration handling subsystem can detect the change, inform the user, automatically reload previous settings, automatically perform a correction to a state consistent with the configuration prior to the change, or any combination thereof. In some embodiments, the automatic correction can include measurement from an electrode and/or sensor within the body (such as an intracardiac electrode) and/or on or near the body surface (such as a localization source patch or ECG electrode).

Positional or Coordinate Reference

As a component of registration, a set of measured inputs can be used to stabilize, reduce, or eliminate undesirable, time-varying changes of the localization system. These can include periodic changes due to respiration or cardiac motion, discrete changes due to the introduction to, removal from, and/or manipulation of devices within the localization field (particularly with low input impedances), and/or slowly-varying changes related to physiological or clinical phenomena (e.g., patient perspiration, infusion of saline, interaction of electrogel, hydrogel, and/or adhesive layers of body surface patches or electrodes with the skin). The measured inputs can be:

1. used directly to offset time-varying changes using subtraction to eliminate common-mode signal components
2. used with weighting (or a linear model) where the weights are determined by:
   a. an analytical model, such as from field theory or principle component analysis
   b. an empirical derivation from a data set used to train a dynamic algorithm
   c. filtering
   d. a combination of a, b, and/or c
3. used with a model based on a higher-order function, perhaps a nonlinear model
4. used with a geometric transform, such as an affine transform, or geometric minimization fitting method The inputs can be composed entirely of electrodes internal to the body, or the inputs can be composed entirely of body surface patches and electrodes, or a combination of these.

Threshold values can be used to trigger user messages or warnings to the UI when the measured inputs deviate from the quantitative model or from the expected output.

In some embodiments, system 100 includes a physical position reference comprising a device (e.g. a device comprising at least one electrode), positioned at a fixed location within the coordinate system near an "area of interest" (e.g. an area where drift and/or other motion artifacts are to be compensated for, for example near and/or in a cardiac chamber). This device can be positioned in a portion of the anatomy such that it is unlikely to move relative to the area of interest, such as when positioned in the coronary sinus. The position of the device is then assumed to be stationary relative to the area of interest (e.g. by localization processor 46), and any motion of the device is determined to be caused by motion artifacts. These motion artifacts are removed from the position data (e.g. localization data) that is gathered relative to all other devices within the area of interest. Movement artifacts can be caused by: respiration; cardiac motion; absorption of sweat into localization patches; degradation of patch adhesion during a procedure; saline delivered during a procedure; a variation in body conduction; the introduction of one or more conductive and/or insulative materials into the patient (e.g. additional catheters); the introduction of one or more devices connected to low impedance ground sources into the patient; and combinations of one or more of these.

Alternatively or additionally, system 100 can include a "virtual coordinate" reference, also referred to herein as a "virtual position" reference. System 100 can be configured to "learn" (or be "trained") to provide a virtual position reference, as described herebelow. Physiologic and/or environmental effects (e.g. effects of respiration or other motion artifact-producing effects) on the localization system can be measured from the surface of the body using "artifact calibration signals" recorded by external electrodes positioned on the patient (e.g. surface patches X1, X2, Y1, Y2, Z1, Z2, and/or 58 described herein, and/or any other similar skin-placed patches). The artifact calibration signals can be recorded while a drive signal is provided to and/or between one or more of the external electrodes (e.g. a drive signal provided by localization signal generator 28). System 100 can be trained (e.g. as part of a calibration or "training" procedure) to recognize these effects, such that a physical position reference is not needed within the patient, instead a virtual position reference is calculated using signals measured by the external electrodes. To train system 100, a physical training device (e.g. device 10, an ablation catheter of system 100, and/or any electrode-containing catheter) is positioned within the patient, proximate an area of interest, and held stationary, and the physical training device is localized, as described herein, using system 100. Localization signals normally correlating to motion of the physical training device are assumed (e.g. by localization processor 46) to be caused by one or more artifacts of the localization system (i.e. since the physical training device was held stationary). During this localization, the external electrodes simultaneously record the artifact calibration signals. The localization signals recorded are then correlated to the simultaneously recorded artifact calibration signals, and mathematically processed to establish a representative relationship between the localization system and the artifact calibration signals recorded by the external electrodes. The representative relationship can comprise a transform to be applied to all devices within the localization field (e.g. the transform becomes a virtual positon reference). The mathematical processing can include: a fitting method; a series of weighted coefficients; a linear system; machine learning; adaptive fitting and/or filtering methods; principal components; filtering (e.g. low pass and/or high pass filtering); other mathematical methods; and/or combinations of one or more of these.

After training, the physical training device can be removed (or repurposed, for example if catheter 10 of system 100 was used as the physical training device), and system 100 can effectively localize devices within the field using the transform (e.g. with improved accuracy by accounting for motion artifacts and other physiologic and/or environmental effects). In some embodiments, the training can be manually and/or automatically repeated to confirm and/or update the transform. For example, system 100 can periodically perform a diagnostic (e.g. using one or more algorithms) to determine if any electrodes or devices positioned in the patient are being moved by a user, and if not, a training of system 100 as described hereabove can commence (e.g. in the background). Once the training is complete, the newly generated mathematical transform can be compared to the previous transform. If the transform is different, it can be updated with the newly calculated one. In some embodiments, buffers are used to store historical data in order to process data over a longer period (e.g. a transform can be adjusted over time based on cumulative training).

Manual Registration

Modeling and automated compensation to stabilize, reduce, or eliminate undesirable, time-varying changes of the localization system can result in a residual offset/error with a static or constant component. Any constant component, of the residual or a bulk compensation in-whole, can be applied by assigning a constant value per coordinate axis (i.e. a constant vector). This constant vector can be determined by user interaction with a user interface and system display for the purpose of manual registration. The system display can show one or more views of the localized devices in relation to a positionally stable or fixed object in the coordinate system, such as a heart chamber surface, model, and/or set of points.

The user's interaction with an input device, such as a mouse, keyboard, and/or touchscreen, can initiate a mode allowing the displacement of the localized devices relative to the fixed object. The initiation of the mode can be integrated in the workflow with key presses, button presses, and/or other commands, or can be a separate window or interface with a distinct entry and exit from the mode.

The displacement of the localized devices relative to the fixed object can be performed on recorded data or it can be applied to live, streaming data such that the localized devices continue to move as governed by their applied or imparted motion in the body—the displacement imparted by the user summed to the calculated coordinate position based on mapping function F, described above, and any other component of registration.

In some embodiments, the displacement is applied to the visual engine of the display only, and must be confirmed by the user before being applied to the mapping function F, or any other localization engine calculation. The application to the mapping function F can be temporary, or can be held in perpetuity, or until otherwise modified.

The user's interaction with the system can be visually or graphically guided by an acquired data set of surface information at, or near, the time of the interaction. The acquired data set of surface information can be provided by sensors or electrodes in contact with the surface, and/or it can be provided by a non-contact sensor or set of sensors. The non-contact sensor or set of sensors can be optical sensors, ultrasound transducers, and/or other ranging or imaging modality. The concurrent visual or graphical display of the acquired surface information can be used to aid the determination of the displacement to be applied by aligning to the two surfaces or objects. In some embodiments, the imaging modality can be ultrasound surface reflections. In one embodiment, a set of ultrasound vectors can be displayed with lengths equal to the range to the surface. The endpoints of the vectors can then be aligned with the fixed object, such as the heart chamber model, surface, and/or set of points. In another embodiment, a new surface can be reconstructed, in part or in full, and it can be used to determine the displacement to be applied by aligning the new surface to the fixed object or heart chamber surface, model, and/or set of points.

Automated or Assisted Imaging-Mediated Registration

The alignment of an acquired data set of surface information to a fixed object, such as a heart chamber model or surface, can be performed based on an algorithm. The algorithm can include a minimization of distances, angles, and/or other cost function or geometric quantity. The minimization can be performed on points, vectors, lines, planes, and/or other geometric structures. The algorithm can be analytical and/or iterative. The algorithm can also include the computation of an affine transform to modify the position, shape, scaling, and/or other geometric property of the acquired data set of surface information to improve the alignment. The geometric properties modified can include all affine transformations or be limited to one or more. In some iterative embodiments, criteria for discontinuing the iterations (an exit condition) are used. The criteria can include the error, minimum error, maximum error, mean squared error, root mean squared error, aggregate error, total error, and/or other condition of a cost function. In some embodiments, the minimization technique can use an iterative closest point algorithm.

In one embodiment, the alignment algorithm uses a set of newly acquired points from a multi-directional, non-contact measurement method, such as ultrasound ranging, which can be transformed to best match the fixed reference object (e.g. a heart chamber surface, model, or set of points). The transformation can be limited to a translation only. The newly acquired points can be compared directly to a set of initially acquired points. Alternatively, the newly acquired points can be used to compute a representative surface and compared to the set of initially acquired points, or the initially acquired points can be used to compute a representative surface and compared to the set of newly acquired points, or both newly and initially acquired points can be used to compute two representative surfaces to be compared.

Localization with Field Estimation

In some embodiments, system 100 comprises an Improved Field Estimation (IFE) Algorithm. Localization of a device or a component of a device within a body cavity or chamber using electrical impedance techniques requires accurate and precise understanding of the electrical field at all points within the chamber. Localization of devices can be performed using the method below or in combination, in part or whole, with the method described in International PCT Patent Application Serial Number PCT/US2016/032420, titled "Localization System and Method Useful in the Acquisition and Analysis of Cardiac Information", filed May 13, 2016, which is hereby incorporated by reference. Given the possibility of non-homogeneity of the field, the (relative) direction and magnitude of the field must be known in the space between any pair of points in order to obtain (relative) positions by integration of field gradients. In some embodiments, system 100 comprises an enhanced field characterization, for the purpose of catheter localization as described below.

A first step for localization of catheters can be characterization of the electric field within the cardiac chamber of interest. Catheter 10, in concert with the console 20 can be configured to detect multiple AC electric fields (e.g. three fields oriented along three mutually perpendicular or nearly perpendicular directions and distinguished by frequency) at multiple spatially distinct positions (e.g. the position of electrodes 12a, such as 48 electrodes 12a) over a spherical surface (e.g. an approximately 1 in. diameter spherical surface). With voltage samples obtained at each electrode 12a, at each of the known frequencies, a least squares and/or other error minimizing technique can be used to compute the direction, magnitude, and gradient of the electric field relative to the known geometry of array 12. As the array 12 moves through the body cavity or chamber, a record of the electric field relative to the array 12 geometry at each electrode 12a is obtained. Since the array 12 orientation is not known a priori, array 12 position and orientation relative to an arbitrarily chosen origin can be obtained by integration of the spatially varying field along a path connecting each electrode 12a with the origin.

See, as examples, the following reference may provide information related to the above approaches for mathematically solving such problems:

1. Kabsch, Wolfgang, (1976) "A solution for the best rotation to relate two sets of vectors", *Acta Crystallographica* 32:922 (with a correction in Kabsch, Wolfgang, (1978) "A discussion of the solution for the best rotation to relate two sets of vectors", "Acta Crystallographica", "A34", 827-828)

In some embodiments, the IFE algorithm processes data recorded during anatomy/geometry acquisition. In some embodiments, the IFE algorithm is capable of processing both continuous data and data interleaved with ultrasound data. In some embodiments, the IFE algorithm utilizes a positional reference to correct for common-mode error sources such as those that occur during respiration (mechanical/impedance) and/or cardiac motion. The positional reference can be a separate catheter that moves in synchrony (common-mode) with the array 12 when not manipulated.

In some embodiments, the IFE algorithm does not require an auxiliary internal device as a position reference. In some embodiments, calculation of array 12 position without requiring a fixed shape of array 12 is performed.

Figure 5:
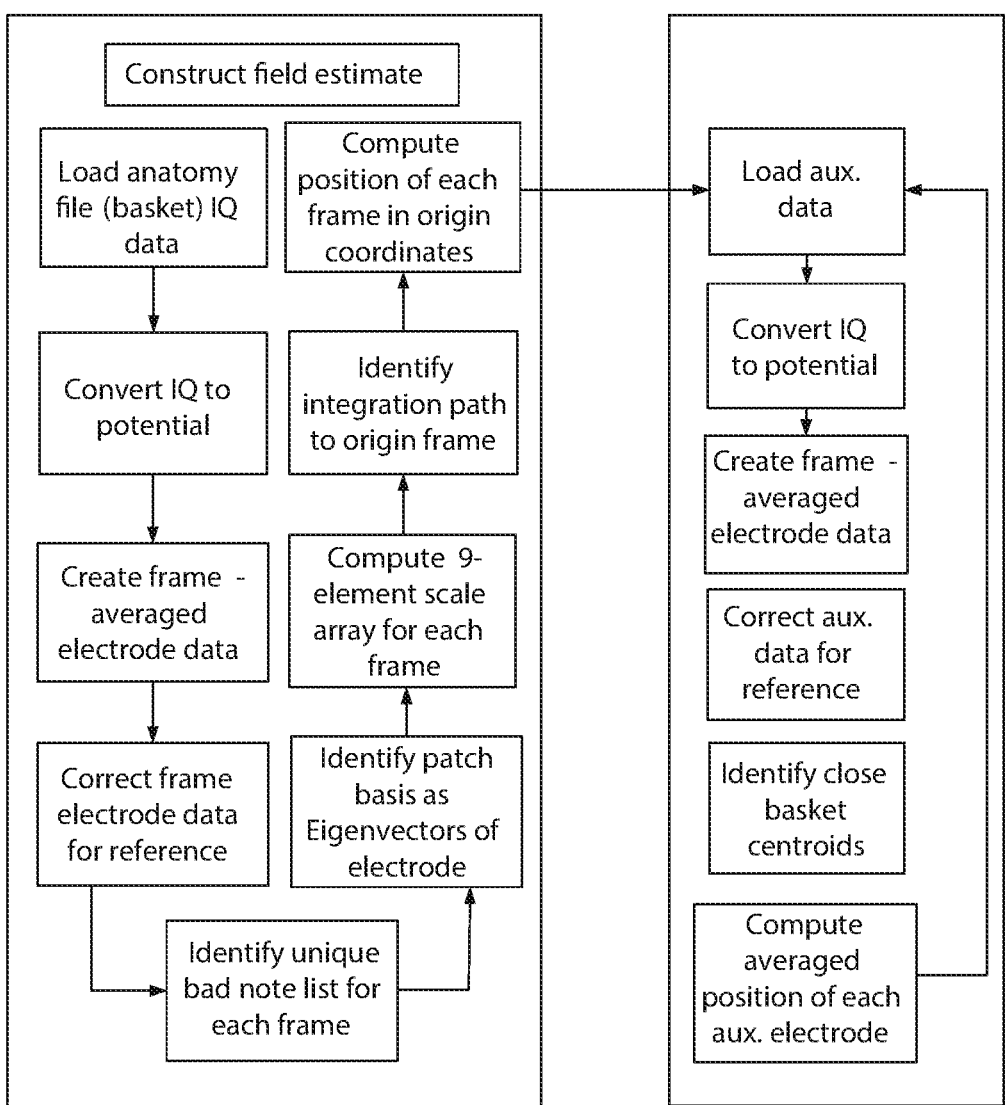
FIG. 5 is a flow chart of an algorithm for performing localization, in accordance with aspects of the inventive concept.

Referring to FIG. 5, a block diagram is illustrated, detailing an embodiment of a method of the IFE algorithm. The block diagram includes sections related to ultrasound and/or surface reconstruction, and describes flow control, field estimation, and auxiliary localization.

The IFE algorithm includes one or more inputs. For example, Idata and Qdata are an array of integers of size N x the number of channels (numCH)×3. The first dimension, N, is the number of samples, the second dimension is the number of channels, and the third dimension corresponds to the 3 localization axis frequencies. The I/Q data can originate from recorded files and/or from real-time streaming data. The IFE algorithm can include the input gain rawdataToVolts, which is a float that defines the ADC 24 count to voltage conversion gain of the system hardware. In some embodiments, gain rawdataToVolts comprises a value of approximately 0.52074e-6. The IFE Algorithm can include the input stdbskdata, an array of size number of electrodes 12a (e.g. 48)×3. The values will be standard (e.g. resiliently biased) XYZ positions of the electrodes 12a of array 12. These values are used to perform fitting and field calculations. The IFE algorithm can further comprise input refnodes aux, an integer array. The contents of refnodes aux designate indices of an auxiliary catheter electrodes that can be used for motion correction.

The IFE algorithm comprises one or more outputs. Outputs of the IFE algorithm are the coordinates of all connected electrodes in system 100 and field estimates (in the form of scale matrices) associated with every array 12 centroid position. Coordinates are given as an N×3 array of floats, and scale matrices are 9 element arrays associated with each frame of the anatomy/geometry recording.

In some embodiments, the IFE algorithm is configured as follows.

Field Characterization and Localization of Basket Centroids

An origin frame is identified. This identification can be taken as the first frame of the anatomy/geometry construction data record. All centroid and auxiliary position vectors will be referred to this frame of reference after transformation from local frames. The basis vectors in the origin frame are defined by the standard (e.g. biased) position measurements of electrodes 12a on array 12.

Field characterization (determination of field strength/orientation) at each centroid position:

Compute spatial field gradients at each centroid position (i.e. rate of change of position with change in potential). Each coordinate dimension (x, y, z) in the local reference frame will change with each of the source potentials producing a 3×3 array of scale factors. This matrix is the conversion from voltage to position in the standard array 12 reference frame attached to a particular centroid:

$$\begin{bmatrix} \dfrac{\partial x}{\partial Vx} & \dfrac{\partial x}{\partial Vy} & \dfrac{\partial x}{\partial Vz} \\[2mm] \dfrac{\partial y}{\partial Vx} & \dfrac{\partial y}{\partial Vy} & \dfrac{\partial y}{\partial Vz} \\[2mm] \dfrac{\partial z}{\partial Vx} & \dfrac{\partial z}{\partial Vy} & \dfrac{\partial z}{\partial Vz} \end{bmatrix}$$

The scale matrix is computed by expressing the position vector between pairs of electrodes 12a in the standard array 12 reference frame as a linear function of the difference in the three measured voltages between the same two electrodes:

$$dx_{ij} = \frac{dx}{dVx}dVx_{ij} + \frac{dx}{dVy}dVy_{ij} + \frac{dx}{dVz}dVz_{ij}$$

in which the subscripts 'i' and 'j' denote electrode 12a positions on the array 12. Each index runs over all electrodes 12a (e.g. 48 electrodes), excluding any identified as unusable by a non-functional electrode algorithm as described herein. This is performed for each possible pair of electrodes 12a:

$$\begin{bmatrix} dx_1 \\ \vdots \\ dx_n \end{bmatrix} = \begin{bmatrix} dVx_1 & dVy_1 & dVz_1 \\ \vdots & \vdots & \vdots \\ dVx_n & dVy_n & dVz_n \end{bmatrix} \begin{bmatrix} \dfrac{\partial x}{\partial Vx} \\[2mm] \dfrac{\partial x}{\partial Vy} \\[2mm] \dfrac{\partial x}{\partial Vz} \end{bmatrix} \gg dx = A\nabla x$$

In which 'del' represents differentiation of position with respect to each of the three source potentials, and dx represents the vector of (in this case) x coordinate differences. In the ideal case, we obtain NumChan$^2$ equations (where NumChan equals the number of electrodes 12a) for the three derivative terms on each coordinate axis. The resulting overdetermined system is solved in the least squares sense to compute the 9 'averaged' scale factors defined by the known position and potential, in three dimensions, of the electrodes 12a. Using singular value decomposition, A=U S V$^t$ and the derivatives along each coordinate axis are given by:

$$Vx = V S^{-1} U^t dx$$

$$Vy = V S^{-1} U^t dy$$

$$Vz = V S^{-1} U^t dz$$

Note that the matrix A is identical over the three coordinate axes so that the singular value decomposition need only be executed once. Robust scale factors are obtained unless a significant number of co-located electrodes are ignored (e.g. if all electrodes from 2 or 3 adjacent splines of array 12 are eliminated).

Matrix multiplication of a set of voltage values by the scale matrix produces a position in physical space relative to the origin of the local reference frame:

$$\begin{bmatrix} dx \\ dy \\ dz \end{bmatrix} = \begin{bmatrix} \frac{\partial x}{\partial Vx} & \frac{\partial x}{\partial Vy} & \frac{\partial x}{\partial Vz} \\ \frac{\partial y}{\partial Vx} & \frac{\partial y}{\partial Vy} & \frac{\partial y}{\partial Vz} \\ \frac{\partial z}{\partial Vx} & \frac{\partial z}{\partial Vy} & \frac{\partial z}{\partial Vz} \end{bmatrix} \begin{bmatrix} dVx \\ dVy \\ dVz \end{bmatrix}$$

The columns of the 9-element scale matrix are recognized as vectors obtained by moving along the gradient of the respective source voltage (e.g. the first column is a vector tangential to the gradient of the X source voltage). The field lines are not constrained to be homogeneous or orthogonal, and a complete description of the field would necessitate knowledge of the scale matrix at each point in space.

System 100 can be configured to perform the following steps.

Reconstruct array 12 electrode 12a positions associated with each centroid in the local coordinates using the local scale matrix. Local coordinates are again defined by the positions of the electrodes 12a in the standard array 12 (e.g. resiliently biased positions). Note that without knowledge of the E-field vectors with respect to some external reference frame, the orientation of each local reference frame is unknown.

Identify a path to the origin frame in voltage space. Moving along this path, find the centroid positions (in voltage space) which are closest to the identified path to origin. This set of centroids, including the target and origin, constitute the actual piecewise continuous path of integration to the origin. (see FIG. 6)

Figure 6:
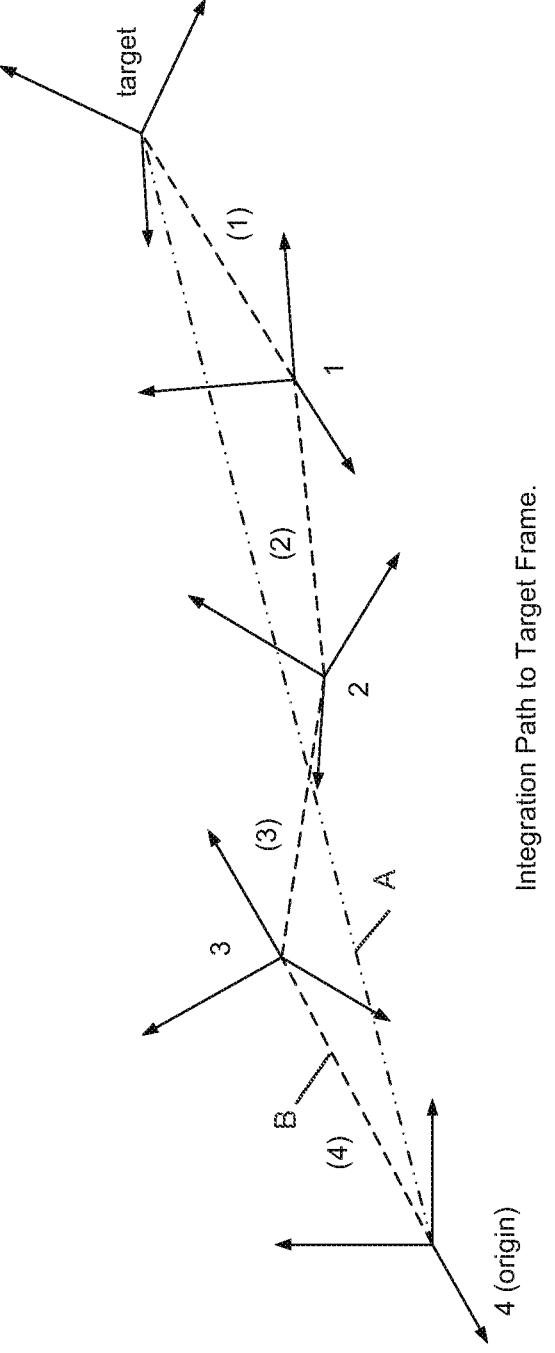
FIG. 6 is a 3D display of an integration path to a target frame, in accordance with aspects of the inventive concept.

Compute the distance between adjacent centroids on the integration path (segments 1-4 in FIG. 6) using the scale factors associated with the centroid closest to the origin (e.g. centroid 1 for segment 1). Each distance is a position vector expressed in the reference frame of the centroid closer to origin (as shown in FIG. 6). The position of the target centroid in the origin frame is the vector sum of the distances between adjacent centroids on the integration path, but these distances must first be expressed in a consistent reference frame, the origin frame. Thus, each distance interval along the integration path must be transformed into the origin frame.

To determine the coordinate transformation between each centroid and the origin frame, system 100 constructs a sequence of transformations between each pair of adjacent centroids along the integration path. The product of this set of transformations along the integration path is the required transformation to the origin frame.

Figure 7:
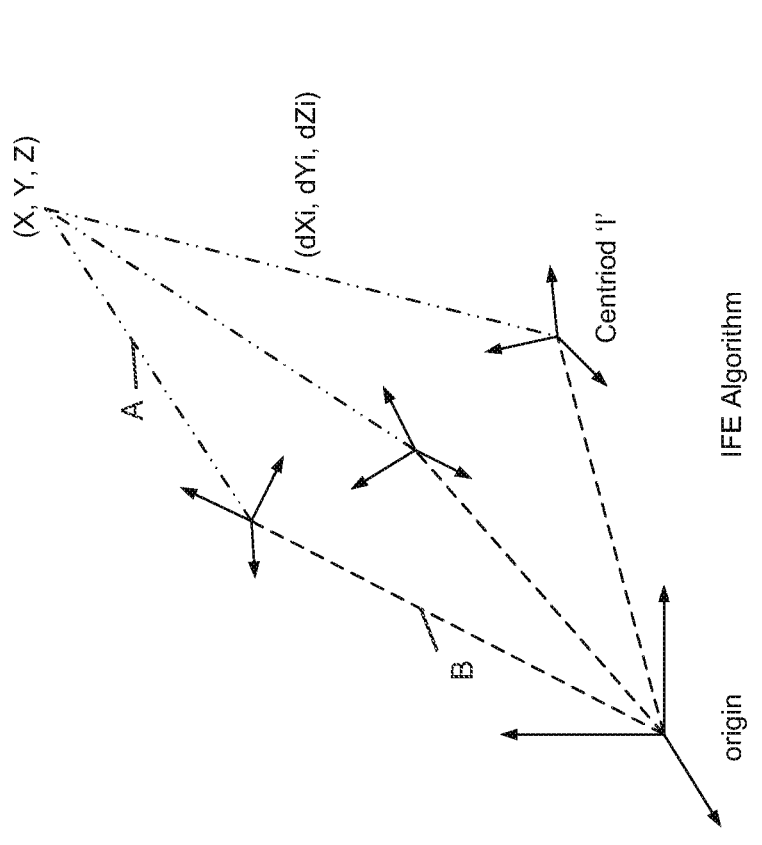
FIG. 7 is a 3D display of an integration path to a target frame, in accordance with aspects of the inventive concept.

Referring to FIG. 7, to transform the most distal position vector, the separation between the target frame and frame 1, back to the origin frame, we first find the transformation between frame 1 and frame 2.

This transformation is obtained by comparison of array 12 in both frames, reconstructed with the scale matrix of the more proximal frame (frame 2 in this example). System 100 reconstructs the array 12 in the more distal frame (e.g. frame 1) using the scale matrix associated with the more proximal frame (frame 2). Then, system 100 uses the Kabsch algorithm to align the two arrays 12 (i.e. the array 12 associated with frame 2, and the array 12 of frame 1 reconstructed with the scale matrix at frame 2). The resulting transformation transfers coordinates from the more distal frame (1) to the more proximal frame (2). System 100 uses the sequence of transformations obtained by aligning adjacent arrays 12 as described above to transform each distance interval (between centroids) back to the origin frame. Then, system 100 repeats the procedure for the next most distal position vector (segment 2, referring again to FIG. 6). The vector sum of the set of transformed distance intervals is the position of the target centroid in the origin reference frame. This process is repeated for each centroid using the uniquely identified path to origin and the associated set of coordinate transformations obtained by applying the Kabsch algorithm between adjacent centroids.

Thus, for each target frame, system 100 obtains a set of transformations which, when applied to a position vector obtained with the local scale factors associated with the target centroid, returns a position vector in the origin reference frame:

$$\begin{bmatrix} x' \\ y' \\ z' \end{bmatrix} = [T_{1,2}] \; [T_{2,3}] \; \dots \; [T_{n-1,n}] \begin{bmatrix} x \\ y \\ z \end{bmatrix}$$

where $[T_{1,2}]$ for example, represents the orthogonal (i.e. length preserving) transformation from reference frame 1 to reference frame 2, etc.

The net effect, referring again to FIG. 6, is to transform position vector 1 into the origin frame. Combined with similarly transformed position vectors 2-4, the (vector) sum is the position of the target frame in the origin coordinate system.

The orientation of the origin frame with respect to global coordinates as defined, e.g., by the potential excitation axes (i.e. the reference electrode 58 reference frame) is obtained by comparing the E-field vectors (columns of scale matrix in origin frame) to the basis vectors in the origin frame. If $\hat{e}_i$ and $e_j$ are unit basis vectors formed from E-field vectors in the origin frame and the coordinate axes in the standard array 12 definition, the components of this transformation are given by:

$$T_{i,j} = \hat{e}_i \cdot e_j$$

where 'i' and 'j' are vector indices (unrelated to the subscripts 1, 2, etc. in the transformations which identify the centroids along an integration path for localization of a target centroid). Note that both vectors must be given in a Euclidian reference frame in order for the inner product to be defined.

Although the E-field vectors in the origin frame are known (as the columns of scale matrix), in practice the E-field vectors can be approximated as the Eigen vectors of the covariance of array 12 voltage in the origin frame. These vectors are known in the origin reference frame, and the above transformation applies. This method has the advantage that Eigen vectors of the covariance matrix are orthogonal, and no subsequent orthogonalization is required.

Additional transformations to, e.g. the AP reference frame, are also obtained.

With the field characterized (e.g. the 9-element scale matrix known at each centroid location) and transformation of position vectors from each centroid (target frame) to the origin frame defined, the position of any electrode in the vicinity of the characterized field is obtained as follows (see FIG. 7).

Identify a subset of centroids which are 'close' to the target electrode in voltage space. A larger number of centroids does not necessarily guarantee more accurate localization, such as for the following reason: increased separation in voltage space is likely to result in reduced fidelity of the E-field characterization (i.e. the field at the centroid may not be representative of the field at the position of the electrode).

For each identified centroid, the potential offset from the mean basket position (i.e. array 12 position) is multiplied by the local scale matrix to obtain the position vector relative to that centroid, in local coordinates.

The sequence of transformations to the origin frame as described above (refer to FIG. 6), and augmented in each case by the transformation from the target frame to frame 1, provides the transformation of the electrode position from the target frame to the origin frame. The electrode position is then the average of the sum of centroid positions and local offsets (represented in the origin frame of reference):

$$X = \frac{1}{n}\sum_{i=1}^{n}(x_i + \Delta x_i)$$

The average of the above quantity over all the identified centroids is the estimated location of the electrode in the origin frame.

Note that non-homogeneity of the field in the volume of interest can render position estimates with increasing error as distance from the volume in which the field is well characterized increases.

Transformation to the patch or AP frame can also be obtained.

In-vivo application of the above described enhanced localization technique has demonstrated ~1 mm accuracy in a quiescent environment (i.e. an environment in which position can be held stable).

Field Characterization with Improved Resolution and Spatial Dimension

In the method described above for field characterization and localization of basket centroids, the estimation of the localization field utilizes a spatio-temporally correlated set of electric potentials measured from a device with a known geometry. Estimation of the field at the centroid of the known geometry offers stability and accuracy representative of the internal volume of the known geometry. Localization fields can vary across or near boundaries of impedance change, such as near the endocardial surface or ostia of connected anatomical structures such as veins, valves, and appendages. Estimation of the field at the centroid of a known geometry can limit the spatial dimension over which the full accuracy of field estimate is realized. The localization field in the interval region between the furthest positions of the centroid of the known geometry and the navigable volume of the device of known geometry is better characterized by the subset of electrodes directly sampling the region rather than by full representative volume of the measuring device.

To estimate local field variations with high resolution in the interval region, the field estimation can also be accomplished by decoupling the spatial and temporal correlation of field-sampling data from the measuring device. In some embodiments, the geometric constraint of the known geometry (e.g. of electrode array 12), such as the full distance matrix between all permutations of electrode pairs of the device, can be relaxed in favor of finer sampling resolution.

In one embodiment, this estimation of local field variations can be accomplished by using only the known distance between adjacent pairs of electrodes. With individual pairs of electrodes, the field variation is sampled only in the direction of the distance vector between the electrodes, and the uncertainty or error increases as a function of the angle between the sampled vector and the direction of field variation. The directional dependence can be reduced by eliminating the temporal correlation of sampled data and aggregating the field sampling data for multiple electrode pairs (and thus multiple sampled vectors) across time that pass through a confined volume of space. The confined volume of space can be constructed by dividing the coordinate system into a set of three-dimensional voxels. Over a period of time, the sampled localization field potentials for discrete electrode pairs can be "binned" (e.g. grouped into "bins") into the set of voxels. In some embodiments, the binning can be determined using a simplified, general localization method, such as that described above as field characterization and localization of basket centroids. The bins can be sized to enclose a statistically significant set of potential samples from the electrode pairs. The set of sampled vectors within the bin define an estimate of the local field. This estimate can be determined by applying SVD to a set of equations relating the spatial field gradient to the spatial and potential magnitude and direction of the sampled vectors. One example is shown in FIG. 18A.

In another embodiment, the sampled potentials from any individual electrode passing through a confined volume of space within the localization field, across time, can be aggregated. The confined volume of space, again, can be constructed by dividing the coordinate system into a set of three-dimensional voxels. Over a period of time, the sampled localization field potentials for any individual electrode can be binned into the set of voxels. In some embodiments, the binning can be determined using a simplified, general localization method, such as that described above as field characterization and localization of basket centroids. The bins can be sized to enclose a statistically significant set of individual electrode potential samples. The difference in potential between adjacent or nearby bins and their relative orientation and distance define an estimate of the local field. This estimate can be determined by applying SVD to an overdetermined set of equations relating the spatial field gradient to the differences in position and potential of the adjacent or nearby bins. One example is shown in FIG. 18B.

Localization of measured potentials, such as from a navigated auxiliary catheter, is accomplished by applying the gradient values known at each voxel to the measured potential.

Localization and Shape Modeling of Auxiliary Devices

Intracardiac field estimation improves accuracy of the location of auxiliary devices, such as lasso catheters or coronary sinus mapping catheters, by accounting for changes in the localization fields across the chamber. The method allows changes of the field across space to be incorporated into the localization of catheters placed close to the chamber wall and into veins/appendages/valves with less distortion. The field change is captured by the electrodes 12a (during the anatomy reconstruction) and processed to integrate field changes.

Figure 15:
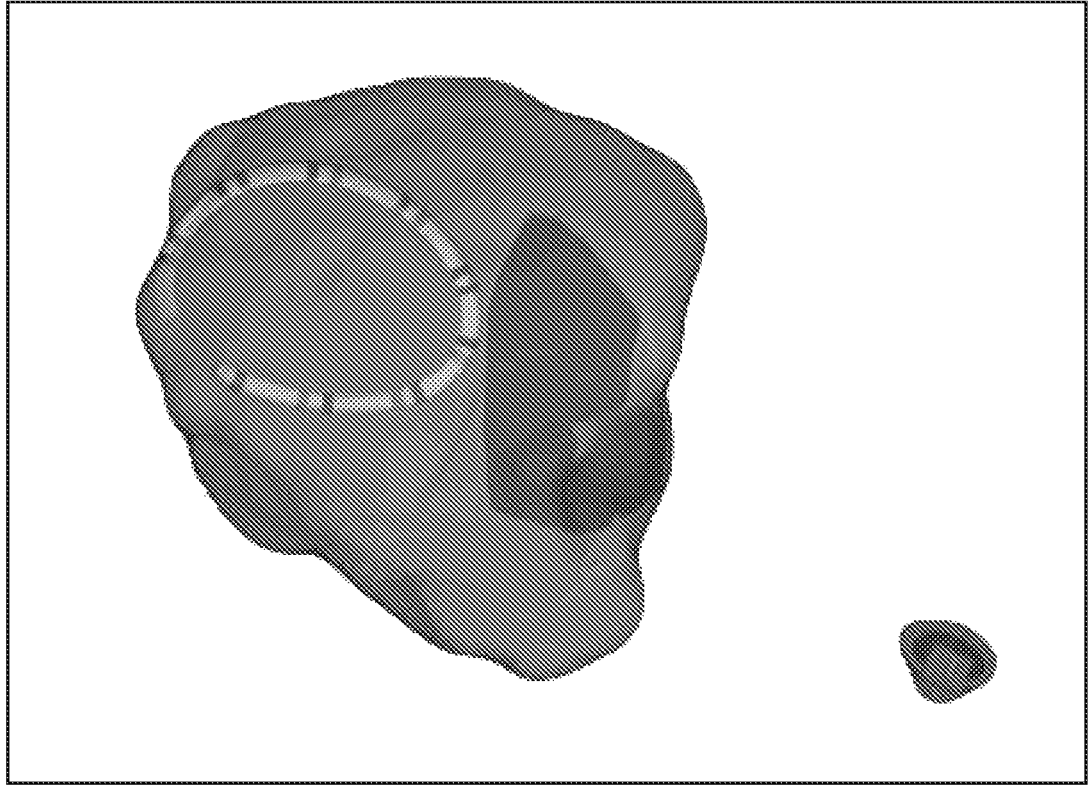
FIG. 15 shows a lasso type catheter, in accordance with aspects of the inventive concept.

In some embodiments, localized electrode positions can be obtained from auxiliary catheters, for example non-linear, nominally circular, 'lasso' type catheters shown in FIG. 15, and can be shape-modeled by a variety of methods, for example:

1. A cubic spline fitted independently to localized electrode data along each of the three spatial coordinate axes
2. A higher order (e.g. fourth or fifth order) polynomial fitted independently to localized electrode data along each of the three spatial coordinate axes
3. A circle of a priori unknown radius and orientation fitted to localized electrode data and the resulting circle can be modified to admit a helical deformation relative to the axis of rotational symmetry.

In some embodiments, the method of calculation for the shape-modeling can be a combination of methods. In some embodiments, the method for the shape-modeling can be changed based on measured or user-defined changes to the set of localized electrode locations, e.g. when a variable shape catheter is configured as a circular loop, a method appropriate for shape-modeling a loop is used; when the catheter is configured as a curve, a method appropriate for shape-modeling a curve is used; and when the catheter is configured as a line, a method appropriate for shape-modeling a line is used.

In some embodiments, the shape-modeling uses the physical specifications of an auxiliary catheter such as electrode spacing, electrode radius, electrode length, radius of curvature, etc. In some embodiments, the shape-modeling is calculated using the localized electrode positions of a subset of the physical electrodes available. In some embodiments, electrode positions can be excluded as 'invalid' from the shape-modeling calculation based on geometric and/or temporal criteria.

Figure 16:
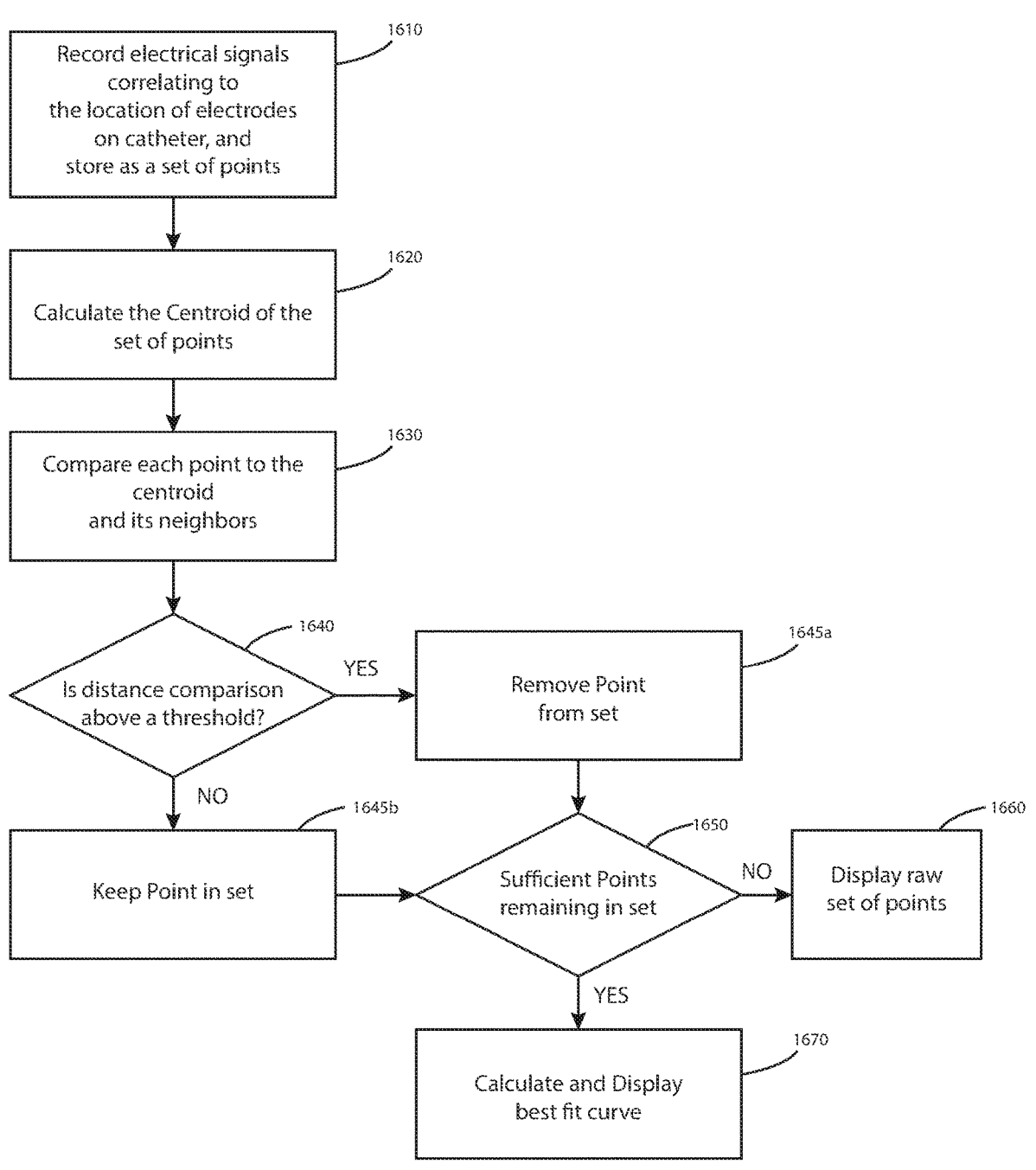
FIG. 16 is a flow chart showing a method of fitting points to a curve representing a catheter, in accordance with aspects of the inventive concept.

Referring to FIG. 16, a method of selecting points (e.g. 2D or 3D coordinates of a location) for shape modeling a catheter is shown. In Step 1610, electrical signals are recorded (such as by one or more components of system 100), correlating to the location of a plurality of electrodes positioned on a catheter positioned in a patient (e.g. in a heart chamber of the patient). The locations are stored as a set of points. In some embodiments, the catheter comprises a variable shape auxiliary catheter, comprising a plurality of electrodes along a portion of its length. The catheter can comprise a plurality of electrodes, such as a catheter including at least 8, 12, or 20 electrodes. In Step 1620, the centroid of the set of points is calculated. In Step 1630, each point in the set of points is compared to the calculated centroid, and/or to its neighboring points. In some embodiments, the distance between each point and the centroid is compared to a threshold, such as a threshold equal to two times the expected radius of the shape being modeled. In some embodiments, the distance between each point and its neighbors is compared to the same threshold, or a different threshold. In Step 1640, if the distance comparison exceeds the threshold, the point is determined to be invalid and removed from the set of points (Step 1645a). In some embodiments, a point is determined to be invalid if at least one, at least two, or all of the comparisons made exceed the compared thresholds, or if at least one of the comparisons exceeds the threshold.

Following the comparisons for all points in the set, it is determined if there are sufficient points remaining in the set to calculate a shape model (Step 1650). In some embodiments, the minimum number of points (e.g. electrodes) required to calculate the shape-modeling is based on the order of the polynomial used for the calculation. In some embodiments, the remaining points must be greater than 8 points, such as greater than 10 or 12 points. In Step 1660, if the minimum number of points required is not met, the system can display the raw position data (e.g. superimposed on a 3D or 2D display of the heart chamber), and not perform a shape modeling calculation. In Step 1670, if the minimum number of points is met, the system can perform the shape modeling calculation, and display the best fit model of the catheter. In some embodiments, the displayed output of the shape-modeling shows graphical representations of all electrodes on the physical catheter, whether they are connected to and localized by system 100 or not. In some embodiments, the electrodes that are connected to and localized by system 100 are graphically displayed differently than electrodes that are not, such as by a color, size, and/or shape difference.

Correction for Movement

Accurate catheter position and motion tracking in a 3D electrophysiological mapping system is essential for arrhythmia diagnostic and ablation treatment strategy. The system of the present inventive concept has high accuracy and can respond to motions sensitively. If the environment is noisy, atrial wall fibrillation can generate high frequency motions that are visually perceived as "jittering" of the catheter during the procedure. The "jittering" motion can distract the physician's attention and cause unnecessary tiredness due to visual fatigue.

In some embodiments, an algorithm of system 10 filters the localization signal to remove the jittering motion while maintaining proper responsiveness of the catheter movement. In order to filter out high frequency noise or motion it can be necessary to narrow the IQ-filter's bandwidth. However, this might introduce additional delay and lengthen response time. It is important to best balance the delay and frequency bandwidth of the filter. CIC (cascaded integrator-comb) filter is the one choice for this purpose. Comparing with IIR, mean and median filters, the CIC filter performs better in terms of the latency with similar reduction of the jittering motion. In addition, it runs quickly (e.g. efficiently) in both embedded (e.g. FPGA) and PC applications. The filter itself requires only additions and subtractions. Multiplication is only needed for output scaling, if needed, to make the filter gain to be 1.

The characteristics of CIC filter are determined by three parameters. With different parameter combination, the filter gives different bandwidth and noise attenuation, while keeping computational complexity simple. The three parameters are: deferential delay (DD), number of sections (Nsect), and down sampling number (Nds).

Scaling Algorithm

System 100 can use an inverse solution to compute cardiac information, such as the charge density distribution and/or surface charge density distribution on a heart chamber surface, such as an atrial chamber surface. The position of electrodes 12a within the chamber (e.g. atria) and the geometry of the chamber surface (e.g. an atrial surface) are the two essential inputs for the formulation of the inverse solution. As the array 12 can be positioned in different locations inside the chamber, the distance from the chamber surface to the closest electrodes 12a can vary significantly. This variation affects the resolution of the inverse solution. For example, the amplitude of reconstructed charge density tends to be more predominant in areas that are spatially close to the electrodes 12a than areas that are spatially far away from electrodes 12a.

System 100 can comprise a scaling algorithm described herebelow that uses a Weighted Minimum Norm estimate method to alleviate distance influence on the forward matrix (pre-scaling); then a uniformly distributed charge source is used to compute post scale values used to adjust the output from the inverse solution accordingly (post-scaling). This technique significantly improves the localization accuracy of focal sources using the inverse solution.

The scaling algorithm can operate (at a minimum) on recorded data after proper signal filtering. In some embodiments, the algorithm further performs V-wave subtraction, as described hereabove. In these embodiments, the algorithm can assume the user selected proper segment on the EGM that corresponding the V-wave, and/or the algorithm assumes the V-wave are consistent through the recording.

Figure 8:
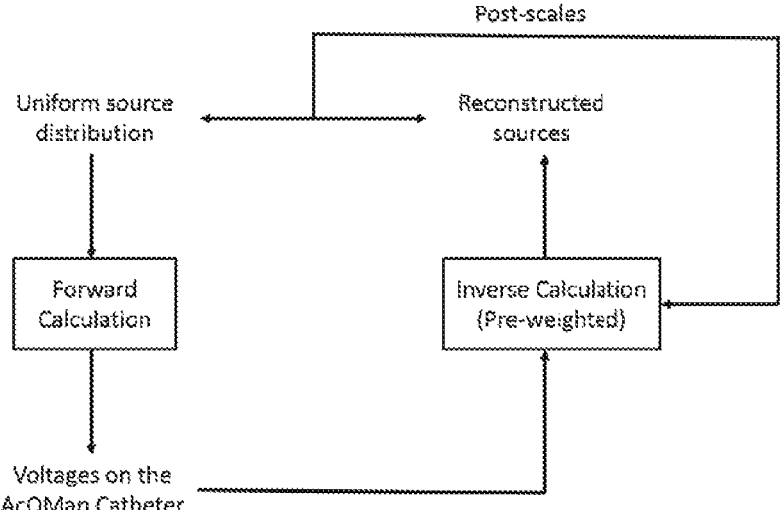
FIG. 8 is a flow chart of a scaling algorithm, in accordance with aspects of the inventive concept.

Referring to FIG. 8, a block diagram illustrates an embodiment of a series of steps of the scaling algorithm, including a pre-scaling and post-scaling.

The scaling algorithm of system 100 can comprise one or more inputs. In some embodiments, an input of the scaling algorithm is the same or similar to a charge density algorithm of system 100, such as when the scaling algorithm includes inputs related to the positions of the array 12 electrodes 12a. The inputs can be vertices and/or triangles that define the chamber surface geometry (e.g. atrial surface geometry). The inputs can include EGM measured from the array 12 electrodes 12a.

The scaling algorithm of system 100 can provide one or more outputs, such as an output comprising surface charge density, dipole density and/or other cardiac information related to the chamber surface.

In some embodiments, the scaling algorithm comprises two major components. First, the weighted minimum norm estimate is used to improve the Tikhonov regularization method; then a uniform source distribution is used to compute post scale values used to adjust the cardiac information (e.g. charge density) from the first step.

Forward Problem (Described in Terms of Charge Density on an Atrial Surface)

The linear relationship between the charge density s and the measured potentials $\phi$ on the catheter is described by the following equation:

$$\phi = As \tag{4}$$

where A is the measurement matrix which encodes the relationship between charge density on the atrial surface and potentials on each electrode 12a, which not only relates to the distance from the electrode 12a to atrial surface but also the atrial geometry. By giving a known source s and the positions of electrodes 12a, the voltages measured on electrodes 12a can be predicted by equation (4).

With the voltage measured on electrodes 12a, system 100 can compute the charge density (and/or the dipole density) on the atrial surface using an inverse solution. A regularization algorithm can be used, since the linear system is under-determined. In some embodiments, the scaling algorithm uses the Weighted Minimum Norm Estimate for the regularization.

Weighted Minimum Norm Estimate (WMNE)

The scaling algorithm can use a weighted minimum norm estimate (WMNE) to compensate the distance effects by introducing a weighted matrix in the objective function:

$$\min \|As - \phi\|_2^2 + \lambda^2 \|Ws\|_2^2;$$

where the weighted matrix $W \in R^{n \times n}$ is a diagonal matrix with diagonal elements as column norms of A.

$$w_{ii} = \|A(:,i)\| = A(:,i)^T A(:,i), i = 1, 2, \ldots, n$$

The solution for (5) is $$\hat{s}_{WMNE} = (W^T W)^{-1} A^T (A(W^T W)^{-1} A^T + \lambda^2 I_m)^{-1} \phi; \tag{6}$$

Denoting $G = (W^T W)^{-1} = \text{diag}(1/\|A(:,i)\|^2)$, i=1, 2, . . . , n, then (6) can be rewritten as:

$$\hat{s}_{WMNE} = GA^T (AGA^T + \lambda^2 I_m)^{-1} \phi \tag{7}$$

The forward matrix can be rewritten using singular value decomposition as $A = U\Sigma V^T$, and substituted back to (7), resulting in a simplified solution for WMNE $$\hat{s}_{WMNE} = GV_m \Sigma_m (\Sigma_m V^T GV \Sigma_m + \lambda^2 I_m)^{-1} U^T \phi; \tag{8}$$

Post Scaling

Once the charge density is calculated using the Weighted Minimum Norm Estimate regularization method, system 100 can compute post scale values to adjust the charge density amplitude. First, system 100 uses a uniform charge distribution to compute the voltage on the array 12 electrodes 12a. Then the voltages due to the uniform source can be used compute the calibration charge density. Comparing the calibration charge density with the uniform charge density, the post scale values can be computed. Finally, the charge density on the atrial surface can be adjusted using the post scale values.

By pre-weighting the measurement matrix to compensate the source depth and post-scaling the reconstructed source to eliminate the system error, the pre-post scaling technique increases the sensitivity to sources that are spatially far from the electrodes 12a. Both simulations and clinic studies by applicant have demonstrated these improvements.

Improved High Pass Filter with Reduced Artifacts

Biopotential signals, such as intracardiac electrograms and surface ECG signals, can contain a set of undesirable signal components, such as a differing magnitude of DC-offset between channels that manifest as a baseline spread, respiration and low frequency drift. These signal components are often composed of relatively low frequencies, such as frequencies <=0.5 Hz, as compared to the spectral content of cardiac activation morphologies. High pass filters (HPF) are a common signal processing tool used to remove or reduce low frequency information from a signal. However, conventional high pass filters can also introduce artifacts into the morphology of the EGM/ECG signals, which can affect the accuracy and resolution of a 3D electrophysiology map. High pass filters often have difficulty concurrently delivering a high stopband attenuation, sharp transition band, and low signal distortion in a single design.

In some embodiments, bio filter 33, bio signal processing 34, or bio processor 36 can comprise an improved high pass filter that reduces the undesired low-frequency signal components described above with high stopband attenuation, sharp transition band, and low signal distortion. A low pass filter is used to remove frequency components above a designated frequency, such as frequencies in the range 0.01-2.0 Hz, such as 0.5 Hz. The output of the low pass filter is then subtracted from the original signal. The low pass filter can comprise two stages, with unique cutoff frequencies and operating at different sampling rates. The two-stage arrangement allows a greater transition band with less distortion as compared to a standard high pass filter while maintaining a low computational complexity, allowing the filter to be implementable in software or firmware. This filter preserves the morphology, signal amplitude, and flatness of the baseline of biopotential signals as compared to a standard high pass filter.

Inverse-Based Far-Field Source Rejection

Far-field activation from sources outside a region of interest in 3D electrophysiology maps can be rejected by performing a field calculation against an artificially located far-field source. As an example, the measurement of activation in a cardiac chamber of interest, a surface A, such as an atrium, can include contribution from sources in another chamber, such as a ventricle. The activation from far-field sources in the ventricle can then be improperly assigned to sources on the atrial surface, A, when mapping the activation pattern of the atrium. In some embodiments, the system 100 can include a method (e.g. an algorithm) to assist in rejecting the activation from far-field sources from the map of the chamber of interest by performing the following steps:

1. Create an additional source region B (a point, a set of points, or a surface) and append to the anatomical surface A using an anatomically accurate relative orientation, such as the location of the valve when the chamber of interest is an atrium and the far-field sources originate from a ventricle.
2. Perform the inverse solution on the union of surfaces A and B.
3. Present the resultant map for surface A only
    i. the far-field source that is, by nature, common-mode to the measured electrograms should be assigned to sources on surface B, reducing any far-field artifact on the map of the chamber of interest.
4. Perform a forward-solution from sources on surface A only to produce electrograms without the far-field component, e.g. for an inverse-based V-wave removal.

The described method can reduce the artifacts or residuals on both the maps and the electrograms caused by filter- or template-based approaches.

Surface Reconstruction with Connected Structures

Reconstruction of an anatomical chamber or surface as described in International PCT Patent Application Serial Number PCT/US2016/032017, titled "ULTRASOUND SEQUENCING SYSTEM AND METHOD", filed May 12, 2016, may lack detail in connected or adjacent structures. As an example, the reconstruction of a left atrium may accurately produce a representation of the atrial body, but the attached venous structure may lack definition beyond the vein ostia. The system 100 can include a method (an algorithm) that incorporates one or more of the following to improve the anatomical definition of connected structures.

The method can include data processing of the cloud of surface points to create the primary surface (the surface reconstructed per PCT/US2016/032017) that identifies regions that include surface points from within/near or comprising a connected structure. In some embodiments, the data processing can incorporate the spatial distribution of surface points in the region. In some embodiments, the data processing can incorporate the spatial distribution of the surface points in the region relative to the primary surface.

The method can also include data processing of the localization data sampled by a device within the chamber of interest, such as a basket mapping catheter and/or an auxiliary diagnostic catheter, distributed throughout the volume of the chamber. In some embodiments, this localization data is provided from the data recorded during the surface reconstruction process. In some embodiments, this localization data is provided from data recorded during an independent acquisition. In some embodiments, field characteristics can be approximated by one or more methods disclosed above in the description of Intracardiac Field Estimation. In some embodiments, regions that include and/or are adjacent to surface points from within/near and/or comprising a connected structure are identified based on differences in the localization field in those regions, intrinsically imposed by the anatomical presence of the connected structure. In some embodiments, a principal direction vector describing the orientation of the connected structure can be determined by the local difference in the estimated intracardiac localization field relative to the surrounding region, spatial distribution of surface points in or near the region, the principal components of the surface points in or near the region, the surface characteristics of the primary surface, the location or orientation of the surface points in the region relative to the primary surface, the location or orientation of the set of field estimates from the sampled localization data, or a combination of these.

The method can further include a processing step to reject surface points from consideration based on the local difference in the estimated intracardiac localization field relative to a surrounding region, spatial distribution of surface points in or near a region, the principal components of the surface points in or near a region, the surface characteristics of the primary surface, the location or orientation of the surface points in a region relative to the primary surface, the location or orientation of a set of field estimates from a region, the location or orientation of a set of sampled localization data from a device within the chamber of interest, the range data from a set of ranging sensors (such as ultrasound transducers) or a combination of these.

The method can further include a processing step to reconstruct a representative surface or surface segment comprising one or more of the identified regions of surface points from within, near, and/or comprising a connected structure. In some embodiments, the representative surface is reconstructed from the one or more identified regions of surface points, independent of information from other surface data. In some embodiments, the processing steps for the representative surface incorporate information from the primary surface. This process can be repeated for each connected structure. In some embodiments, the reconstruction of the representative surface can utilize a meshing algorithm, such as a ball-pivot or alpha-shapes algorithm. In some embodiments, the reconstruction of the representative surface can utilize an iterative fitting or deformation algorithm, such as an algorithm that begins with a generalized surface shape, modifies one or more regions of the surface shape to the set of points, estimates a cost function such as a distance-error, evaluates the cost function against an ending criteria such as a threshold, and iteratively continues with the determination of a next modification to the surface shape if the end criteria is not met. In some embodiments, the reconstruction of the representative surface can utilize an analytical set of spatial series basis functions, such as a spherical harmonic expansion, to approximate a best-fit surface to the set of points.

The method can also comprise a processing step to combine or merge one or more representative surfaces and/or surface segments of connected structures to the primary surface, or a portion thereof. In some embodiments, the merging of surfaces is performed concurrently with the reconstruction of the representative surface and/or surface segment for each connected structure. In some embodiments, the merging of surfaces is performed using a mesh blending procedure. In one embodiment, the merging procedure can include one or more of the following steps:

1. A coarse mesh encompassing both the primary surface and the set of identified surface points from within, near, and/or comprising the connected structure is created to union the two structures using a mesh generation algorithm, such as an alpha shapes algorithm.

2. A best-fit shell to the identified surface points is determined using a fitting algorithm, such as principal component analysis. The best-fit shell can have a simple shape such as an ellipsoid, cylinder, sphere, or similar geometry.

3. A subset of triangles of the coarse mesh is identified at the intersection with the best-fit shell as the opening, or ostium, of the connected structure.

4. The portion of the coarse mesh beyond the ostium is retained and is connected to the primary surface via the triangles along the ostium.

5. Interior triangles are removed based on the continuous surface normal direction, using the surface normal of the triangles at the ostium as a guide.

6. Holes in the resulting surface are closed.

7. The resulting surface is smoothed, re-meshed, or both.

Referring now to FIG. 19, a method of recording cardiac activity and displaying a "beating" heart anatomic model is illustrated, consistent with the present inventive concept. Method 1900 comprises: recording cardiac activity data over multiple cardiac cycles, including both electrical activity data and wall position data; analyzing the electrical activity data to determine discrete segments of the phase of the recorded cardiac cycles; segmenting the wall position data per the discrete phase segments; generating an anatomic model of the cardiac chamber(s) for each discrete phase component; and displaying a beating anatomic model based on the recorded cardiac activity data.

In Step 1910, cardiac activity data is recorded, such as data recorded using one or more recording devices of system 100 (e.g. catheter 10), as described herein. Electrode array 12 can comprise one or more electrodes 12*a* and/or one or more ultrasound transducers 12*b*. System 100 can be configured to localize electrode array 12 within a cardiac chamber (i.e. determine the position and orientation of array 12 relative to a localization field generated within the patient), and record cardiac activity data of the patient. Cardiac wall position data ("anatomic" data) can be recorded via the one or more ultrasound transducers 12*b*, as described herein. Simultaneously (or relatively simultaneously, such as in an interleaved pattern), cardiac electrical activity data ("biopotential" data) can be recorded via the one or more electrodes 12*a*, also as described herein. In some embodiments, data is recorded for a period of time (e.g. over multiple cardiac cycles), the data is manipulated as described immediately herebelow after a complete dataset has been recorded, and a beating anatomic model is generated and displayed as a "recorded" video. Alternatively or additionally, a first subset of the data is recorded and manipulated (e.g. analyzed), a subsequent, second subset of data is recorded, and a beating anatomic model can be generated and displayed based on both the first subset of data and the second subset of data. In this configuration, a "live view" beating anatomic model can be displayed (e.g. a view with a short delay between the actual anatomic motion and the corresponding video representation).

In Step 1920, the recorded biopotential data is analyzed, such as by a processor of console 20 of FIG. 1, to determine the time periods, or segments, representing various phases of the cardiac cycle (e.g. phases of the heart beat). For example, recorded biopotential data of a regular and/or near regular heart rhythm (e.g. sinus rhythm or flutter), can be segmented into a periodic set of time segments, representing phases of the cardiac cycle. In some embodiments, these segments repeat with little variation from cycle to cycle. In some embodiments, the biopotential data is analyzed to determine a key time index of a unique phase of the cardiac cycle (e.g. the rise or fall of the V-wave), and the data between each sequential key time index identified is segmented into a set number of variable duration time segments. Alternatively, the data between each sequential key time index identified is segmented into a variable number of set duration time segments.

In Step 1930, the recorded anatomic data is aggregated, per the time segments determined in Step 1920. For example, for each common time segment of each recorded cycle, the recorded anatomic data, comprising a set of points representing at least a portion of the cardiac surface during each time segment, is aggregated to form a set of anatomic data comprising points from multiple cycles representing a common time segment (e.g. a common phase of the cardiac cycle). This process is performed for each time segment, for each recorded cycle, and compiled into a dataset, such as a dataset comprising multiple "bins". The total number of bins can be set to equal the average number of time segments of the recorded cycles. In some embodiments, for example when the biopotential data is segmented into set duration segments, sequential cycles can comprise more or less segments than the number of bins, and the data can be adjusted to account for the difference. For example, if a cycle comprises more than the number of bins, the additional segments can be skipped (e.g. ignored). The additional segments can be skipped by removing the additional segments from the "end" of the cycle, and/or an algorithm can be used to determine the segments to be skipped, for example if three additional segments exist in a cycle comprising 33 segments, segment 11, 22, and 33 can be skipped. Additionally or alternatively, additional time segments can be "assigned" to a different bin, for example the last bin or the last two bins of the cycle. In some embodiments, the bins to which the additional segments are assigned are dithered.

In some embodiments, if a cycle comprises less than the number of bins, the time segments can be distributed into a subset of the bins. The distribution can be evenly sampled (e.g. earlier segments are "assigned" to earlier bins), or the segments can be analyzed, and assigned to bins based on having similar properties to data (e.g. data already present) in the bin to be assigned.

In Step 1940, for each bin, the data contained therein is used to create an anatomic model of the heart chamber(s) for the associated time segment of the cardiac cycle represented. In some embodiments, the anatomic model is created as described herein and/or in reference to applicant's co-pending U.S. patent application Ser. No. 15/128,563, titled "Cardiac Analysis User Interface System and Method", filed Sep. 23, 2016, the content of which is incorporated herein by reference in its entirety for all purposes. In some embodiments, a "foundational model" is created, comprising a model created from a single bin, representing a single time segment, for example the time segment representing systole or diastole. Anatomic models representing the remaining bins can be generated based on the foundational model, such as by using a conformal mesh. Each vertex of the foundational model can be projected along its normal axis, inward and outward, and each vertex can be adjusted along the projection to match and/or at least approximate the data in subsequent bins, such as to create anatomic models representing the data in each bin, based on the foundational model. One or more smoothing filters can be used to refine (e.g. smooth) the anatomic models created. For example, a low pass filter can be used to adjust the location of each vertex of each anatomic model, based on the distance from a fixed location (e.g. the coordinate origin), to each vertex throughout each anatomic model. Such filtering can produce "smoother" and/or more cohesive motion when the anatomic models are displayed as a dynamic model (also referred to as a beating heart model herein), such as in step 1950.

In Step 1950, the sequential anatomic models, each representing a phase of the cardiac cycle, are displayed as a dynamic model. In some embodiments, electrical data, such as calculated data based on the recorded cardiac activity data as described herein (e.g. voltage data, dipole density data, and/or surface charge data) is superimposed on the dynamic model. The superimposed images allow an operator to visualize one or more characteristics of the recorded anatomy, such as electrical-mechanical coupling and/or delay. In some embodiments, system 100 processes the data representing the dynamic model to determine one or more metrics relating to the electrical activity, and/or the size, shape, and/or motion of the anatomy. For example, system 100 can measure and/or display one, two or more of: ejection fraction, stroke volume, chamber volume, chamber dimensions, regional wall displacement, velocity, or other index/representation of loss of function or stiffness, and the like. Certain physiologic parameters can be calculated and displayed by system 100 as a function of time, such as a chamber volume (e.g. atrial volume). For example, an atrial or other chamber volume can be presented (e.g. as a curve) in a graph representing chamber volume versus time. Functional characteristics, such as displacement or velocity of the wall at each vertex or region (instantaneously over a window of time) can be displayed as a map (e.g. a color map) depicting a representation (e.g. an index) of contractility. The difference and/or change in functional characteristic before and after a clinical event, such as an ablation procedure, can be similarly displayed as a color map depicting regions of altered function arising from the clinical event. Additionally or alternatively, one or more surface dynamics can be measured and/or displayed, such as tissue stress or strain, blood velocity, regional wall contractility or other index/representation of loss of function or stiffness.

System 100 can be configured to determine metrics related to the size, shape, and/or motion of the patient's heart, such as by creating a dynamic model as described hereabove. Assessment of these metrics can be performed by system 100 as part of a safety algorithm (e.g. of processor 26 or other component of console 20). The safety algorithm can be run continuously, or at least when a procedure is being performed on a patient, such as cardiac procedure performed using a cardiac ablation device (e.g. an endocardial ablation catheter or an epicardial ablation device). The cardiac ablation device can be connected to console 20 (e.g. when console 20 is configured to provide energy to an ablation device) or an energy delivery device operably connected to console 20 (e.g. such that console 20 can control the energy delivery to the cardiac ablation device). When an unsafe or otherwise undesired condition is detected, system 100 can alert a user (e.g. via an audible, visual, and/or tactile user output component of user interface 27) and/or adjust (e.g. cease or at least reduce) operation of the cardiac ablation device. For example, system 100 can be configured to detect an undesirable condition selected from the group consisting of: tamponade (e.g. due to pericardial bleeding); stroke; a deviation from a stable hemodynamic condition; decrease in ejection fraction; decrease in stroke volume; decrease in wall motion; undesirable decrease in chamber volume (e.g. undesirable decrease in average chamber volume); undesirable increase in chamber volume (e.g. undesirable increase in average chamber volume); and combinations thereof. The undesirable condition can be a condition of a global heart chamber characteristic (i.e. full chamber) or regional heart chamber characteristic (e.g. portion of a chamber wall). In some embodiments, an undesirable condition is a decrease in atrial volume (e.g. a decrease in atrial volume at comparable heart rates) that is indicative of decrease atrial filling which can correlate to a bleed resulting in tamponade. In some embodiments, system 100 is configured to detect tamponade (e.g. as described hereabove), and alert a user and/or deliver (or cause the delivery of) a coagulant or other treatment (other drug or an interventional treatment) to manage the bleeding and/or the tamponade.

Figure 21:
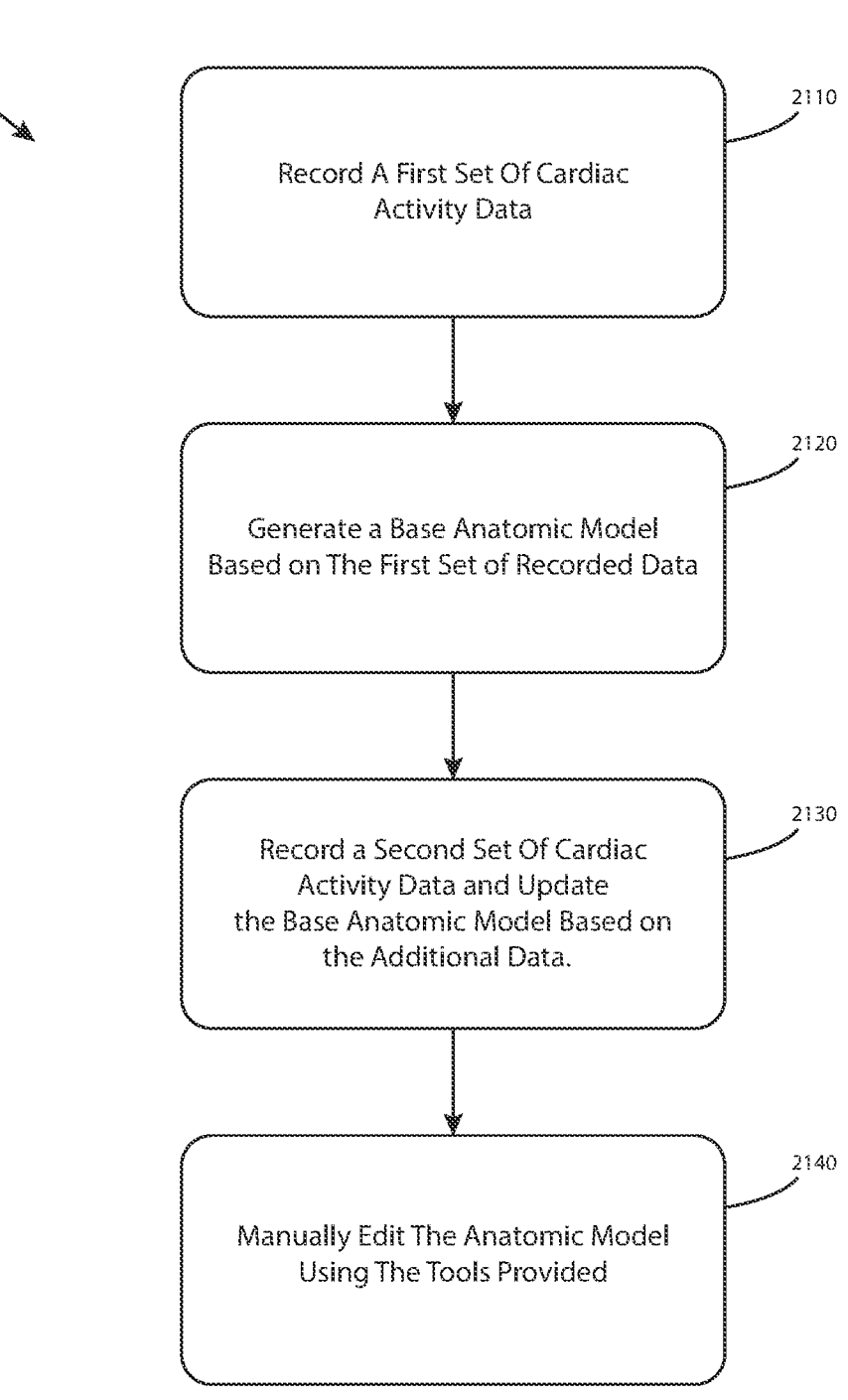
FIG. 21 is a flow chart of an embodiment of a method for editing a model of the heart, in accordance with aspects of the inventive concept.

In some embodiments, one or more of the sequential anatomic models can be refined by a user, for example using meshing and/or smoothing techniques, such as described herebelow in reference to FIG. 21.

Figure 20:
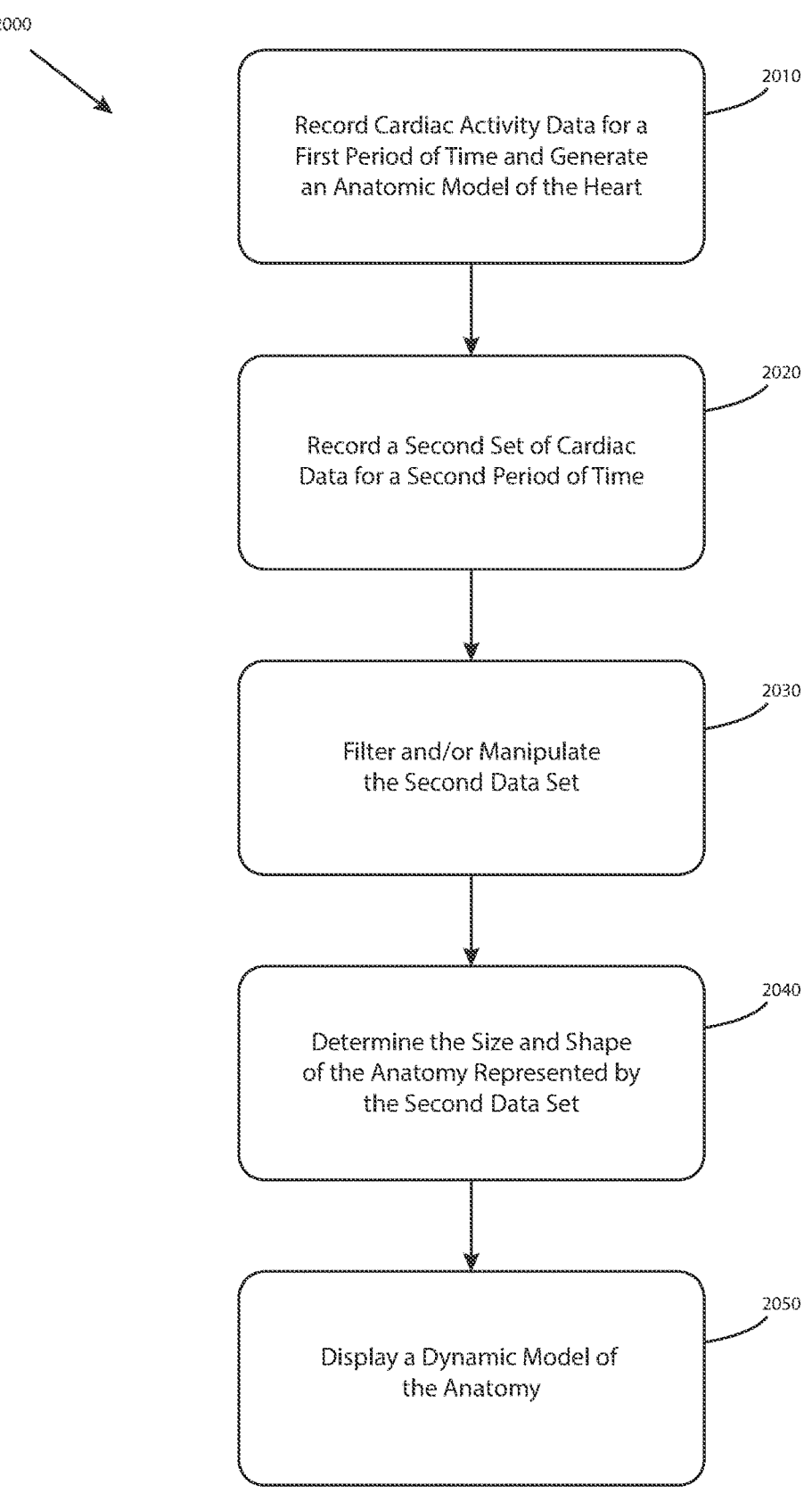
FIG. 20 is a flow chart of an embodiment of a method for displaying a dynamic model of the heart, in accordance with aspects of the inventive concept.

Referring now to FIG. 20, a method of recording cardiac activity data and updating an anatomic model of the heart (e.g. a chamber of the heart) based on a "snapshot" of the data is illustrated, consistent with the present inventive concepts. Method 2000 comprises: recording cardiac activity data and generating an anatomic model of the heart; recording a "snapshot" of cardiac activity data, including wall position data; filtering the recorded data; determining an approximation of the size and shape of the recoded anatomy from the snapshot of data; and updating the anatomic model based on the approximated size and shape of the anatomy.

In Step 2010, cardiac activity data is recorded, such as data recorded using one or more recording devices of system 100 (e.g. catheter 10), as described herein, and an anatomic model of the heart is generated. Electrode array 12 can comprise one or more electrodes 12a and/or one or more ultrasound transducers 12b. System 100 is configured to localize electrode array 12 within a cardiac chamber (i.e. determine the position and orientation of array 12 relative to a localization field generated within the patient), and record cardiac activity data of the patient. Cardiac wall position data ("anatomic" data) can be recorded via the one or more ultrasound transducers 12b, as described herein. Simultaneously (or relatively simultaneously, such as in an interleaved pattern), cardiac electrical activity data ("biopotential" data) can be recorded via the one or more electrodes 12a, also as described herein. A first set of data can be recorded for a first period of time, such as for at least 5 seconds, 15 seconds, or 30 seconds, or for less than 1 minute or less than 5 minutes. A static anatomic model of the heart (e.g. a chamber of the heart from which the data is recorded) is generated using the first set of recorded data, such as a model representing shape of the chamber at systole, diastole, and/or an intermediate shape between these two phases. Methods of generating the static model are described herein, as well as applicant's co-pending applicant's co-pending U.S. patent application Ser. No. 15/128,563, titled "Cardiac Analysis User Interface System and Method", filed Sep. 23, 2016, the content of which is incorporated herein by reference in its entirety for all purposes. In some embodiments, the anatomic model is generated from CT and/or MRI data recorded prior to and/or during method 2000. Alternatively, the anatomic model can comprise a generic anatomic model configured to be updated by method 2000. In some embodiments, the static anatomic model can be refined by a user, for example using meshing and/or smoothing techniques, such as described herebelow in reference to FIG. 21.

In Step 2020, a second set of data can be recorded for a second period of time, such as a time period shorter than the first period of time. In some embodiments, the second set of recorded data represents an instantaneous "snapshot" of the cardiac chamber, such as when the second period of time comprises a time period less than 0.5 seconds, such as less than 100 ms, or less than 30 ms. The second recorded data set can comprise a sparse sampling of the cardiac chamber, such as a sampling comprising less than 96 samples (i.e. less than 96 ultrasonic measurements). The second recorded data set can comprise multiple ultrasonic measurements made from electrode array 12 in multiple directions simultaneously and/or nearly simultaneously, such as to allow for an approximation of the size and/or shape of the anatomy from the sparse sampling of the anatomy, as described herebelow.

In Step 2030, the second recorded data set can be filtered, and/or otherwise manipulated. In some embodiments, one or more ultrasonic reflections can be missing from the dataset (e.g. if a reflection was never detected in response to an ultrasonic pulse or "ping"), and system 100 can be configured to "fill in" the missing data as described immediately herebelow. In some embodiments, a fixed value can be inserted, such as a fixed value determined by system 100 to minimize negative effects of subsequent calculations performed on the data set, such as a fixed value representative of a "middle" or neutral (not systole and not diastole) position of the anatomy. In some embodiments, a fixed value based on a historic average value (e.g. based on an average value from the first data set) can be inserted to replace a missing data point. In some embodiments, a fixed value based on a single historic value can be inserted, such as the "most recent" valid data point (e.g. most recently recorded valid data point, from the transducer with the missing data). In some embodiments, the missing data can be inserted using a fitting algorithm, such as an interpolation algorithm, such as an algorithm using a linear, spline, piecewise continuous, and/or other interpolation method. In some embodiments, the missing data can be inserted based on a value determined by an adaptive and/or a machine learning algorithm, such as an algorithm based on one or more subsets of valid data within the data set.

In Step 2040, the size and/or shape of the anatomy represented by the second recorded data set is determined. In some embodiments, an "envelope-type" algorithm, such as a convex hull, can be implemented to determine a rough estimate of the size and shape of the anatomy, by encapsulating all measured ultrasonic points within a complex shape. Alternatively or additionally, a stress/strain model can be applied to the static model generated from the first data set, and a push/pull algorithm can be applied to the stress/strain model using the second data set, such as to find a conforming "fit" of the stress/strain model to the second data set of "instantaneous" points.

In some embodiments, the static model can be represented by a mesh of vertices, $P_{Original}(x,y,z)$, that can be "updated" to $P_{Instant}(x,y,z)$ by the equation:

$$P_{instant}(x,y,z)=P_{original}(x,y,z)+\Delta P,$$

where $\Delta P$ is estimated by using the second recorded data set, and the change in each vertex in $P_{Original}(x,y,z)$ is constrained to be in the local normal direction. $\Delta P$ can be defined as a combination of functions, the global anatomy fit, regional anatomy fit, temporal, and spatial smoothing with weighting parameters, $\lambda_n$:

$$\Delta P=\lambda_1(F_{GlobalFit})+\lambda_2(F_{RegionalFit})+\lambda_3(F_{Spatial\ Smoothing})+\lambda_4(F_{TemporalSmoothing})$$

For example, a global fit function could be implemented using the mean or median separation of each ultrasound data point to its closest location on the anatomy. A regional fitting can be used to build a relationship between each ultrasound point and the vertices on the anatomy. This relationship can be built by defining a function (e.g. inverse distances or Gaussian) between all the ultrasound points of the second data set and the vertices of the static model. Once this relationship between the measurements and the anatomy is made, the anatomy can be deformed. The lambda values weight different aspects of the solution, or could themselves be functions of the vertex and can be set due to confidence in the ultrasound measurement or due to distance of the nearest ultrasound measurement.

In some embodiments, the static model can be represented by a mesh of vertices, $P_{Original}$, that can be "updated" to $P_{Instant}(t)$ by:

$$P_{instant}(t)=P_{original}+\Delta P(t),\qquad(1)$$

where $\Delta P$ is estimated by using all or a subset of the instantaneous ultrasound data points (the second data set of points). The formulation in equation (1) allows the static mesh to become a deformable mesh, where the deformation is due to changes in ultrasound range data that relates to changes in cardiac wall position (thus contractility and volume). In some embodiments, there will be fewer ultrasound data points than vertices, therefore $\Delta P(t)$, will need to be estimated at most locations.

The unknown $\Delta P(t)$ can be estimated using interpolation and/or extrapolation methods, energy function minimization, and/or with data models such as stress strain relationships. The interpolation and/or extrapolation methods can include inverse distance weighting, closest neighbors inverse distance weighting, basis function interpolation, and/or kriging. The basis function interpolation implementation can include defining a basis function (such as spherical harmonics basis functions), and using these functions to estimate the unknown data points. An energy (cost function) formulation can also be used to determine the $\Delta P(t)$ that minimize the instantaneous energy $$E_{Instant}(x,y,z,t) = \frac{\sum_{n=1}^{M} w_n E_n(x,y,z,t),}{\sum_{n=1}^{M} w_n}\qquad(2)$$

where different energies can be defined, $E_n$, with weights, $w_n$, indicating the relative influence of the energy term on the total energy. The weight terms, $w_n$ can also be a function of other measurable quantities. An example of an energy term could be $E_{datafit}$, which can be defined as the error between the ultrasound range data and their corresponding vertex on the anatomy. Another energy term can be defined as $E_{OriginalShape}$ which could be defined as the deviations from the original anatomy's spatial gradients. The overall energy with these terms could then be defined as $$E_{Instant}(x,y,z,t) = \left(\frac{1}{w1+w2}\right)w_1 E_{data\ fit}(x,y,z,t) + w_2 E_{Original\ Shape}(x,y,z,t).\qquad(3)$$

A model based deformation approach can include defining a stress/strain model of the anatomy. With the known deformations, the stress/strain can be estimated at each location. The stress/strains can then be interpolated or an energy function can be built and minimized, to determine the stress and strain at each vertex. The vertex positon can then be updated to correspond with the estimated stress/strain. Once Δ P(t), is computed for every vertex and timepoint, several metrics can be computed such as, instantaneous blood volume, active and passive blood volume emptying, and/or regional based contractility.

In some embodiments, an interpolation based deformable mesh is configured as described immediately herebelow. For each time instant, the coordinates of the ultrasound trans-ducers within the cardiac chamber are determined. For each time instant, the vector vec$_n$ that defines the M mode line of site of the ultrasound transducer and the ultrasound range data USpos$_n$ is determined for each ultrasound transducer. The intersection between the M mode ultrasound transduc-ers and the static cardiac anatomy is determined. The closest vertices, vertex n to the intersections of the ultrasound vectors(vec$_n$) and the anatomy is determined. The distance, dist$_n$, between the ultrasound range data, USpos$_n$, and ver-tex$_n$ is computed. ΔP(n, t) is assigned as the projection of dist$_n$ and the local surface normal at vertex$_n$. Once all ΔP(n, t) are determined for the valid ultrasound data, interpolation to the rest of the vertices is determined with closest neigh-bor's inverse distance scaling. The volume of the anatomy is computed with updated vertex positions for every time instant.

In Step 2050, a dynamic anatomic model can be dis-played, based on the first data set and updated by the second, similar to as described hereabove in reference to Step 1950 of FIG. 19.

Referring now to FIG. 21, a method of generating and editing an anatomic model of the heart is illustrated, con-sistent with the present inventive concept. Method 2100 comprises: recording a first set of cardiac activity data, including wall position data; creating a base anatomic model of the heart (e.g. a chamber of the heart) based on the first set cardiac activity data; collecting additional cardiac wall position data and updating the base anatomic model; and editing the base anatomic model, such as via a graphical user interface.

In Step 2110, a first set of cardiac activity data is recorded, such as data recorded using one or more recording devices of system 100 (e.g. catheter 10), as described herein. Elec-trode array 12 can comprise one or more electrodes 12a and/or one or more ultrasound transducers 12b. System 100 is configured to localize electrode array 12 within a cardiac chamber (i.e. determine the position and orientation of array 12 relative to a localization field generated within the patient), and record cardiac activity data of the patient. Cardiac wall position data ("anatomic" data) can be recorded via the one or more ultrasound transducers 12b, as described herein. Simultaneously (or relatively simultane-ously, such as in an interleaved pattern), cardiac electrical activity data ("biopotential" data) can be recorded via the one or more electrodes 12a, also as described herein. As used herein, anatomic data can refer any data collected by system 100, such as by electrode array 12 or other data collecting device of system 100, that is used to generate the anatomic model. Anatomic data can include data from the group consisting of: data comprising surface points (e.g. surface locations) measured via ultrasound; volume data determined using a localization method, such as by tracking the position, over time, of an electrode within the chamber (e.g. the cardiac chamber comprising at least the volume of the convex hull of the collected positions of the electrode); data comprising surface points collected using a localization method, such as data points collected via a contact sensing catheter of system 100 used with a localization system; data taken from external to the body (e.g. using an external visualization device), such as MRI and/or CT data; and combinations of one or more of these.

In Step 2120, a base anatomic model of the heart is generated (e.g. comprising a set of vertices and polygons defining a 3D surface), based on the first set of recorded data. As described herebelow, method 2100 is used to generate and edit a static anatomic model of the heart (e.g. a chamber of the heart from which the data is recorded), such as a model representing a shape of the chamber at systole, diastole, and/or an intermediate shape between these two phases. Methods of generating the static model are described herein, as well as in applicant's co-pending U.S. patent application Ser. No. 15/128,563, titled "Cardiac Analysis User Interface System and Method", filed Sep. 23, 2016, the content of which is incorporated herein by reference in its entirety for all purposes. Additionally, method 2100 can be iterated (e.g. iterated through sequential static anatomic models representing sequential phases of the cardiac cycle) to generate and edit a dynamic model of the chamber, such as a dynamic model described herein. In some embodiments, the base anatomic model comprises an anatomic model imported into system 100 from an external imaging source, such as an MRI and/or CT.

In some embodiments, the static anatomic model com-prises a model generated using a method of "building" a complex 3D geometry around a set of points while or after they are collected, such as by using an alpha-shapes method and/or a "growth" method. For example, a static model of the chamber during diastole (i.e. the phase of the heartbeat when the heart muscle relaxes and allows the chambers to fill with blood, and the chamber is at its largest) can be built using a growth method as described immediately herebelow. In these embodiments, as the first set of data is recorded, the set of points are considered to exist exclusively within the chamber, and a fitting algorithm, such as a convex hull, inclusive of all (excluding outliers) points collected, throughout all phases of the heartbeat, can be considered to represent the chamber at its largest volume (i.e. diastole). In some embodiments, a similar method can be used, and a gating mechanism, such as a gating mechanism based off of the cardiac electrical activity data, can be incorporated to include only points collected during a particular phase of the heartbeat (e.g. during systole, when the chamber is at its smallest volume).

In Step 2130, a second set of cardiac activity data ("addi-tional" data) is recorded, and the base anatomic model can be updated based on the additional data. In some embodi-ments, such as when the base anatomic model comprises an MRI and/or CT image, additional data can be used to register the imported model to the anatomy within the coordinate system of system 100. Additionally or alternatively, addi-tional data can be used to "fill in", or increase the resolution of an area of the anatomic model. For example, system 100 can inform a user (e.g. via a user interface) of an area of low data density (e.g. a sparsely sampled area). The user can collect additional data correlating to that area, such as by directing (e.g. steering) catheter 10 "towards" the area indicated, and recording additional data. The additional data collected can be compiled with the first set of data to generate an improved base anatomic model. Alternatively, the base anatomic model can be updated using the additional information. In some embodiments, the user can resample an area, for example when the user suspects an issue with the model. The additional data can be used to confirm the accuracy of the base anatomic model and/or update the base anatomic model.

In Step 2140, system 100 can provide one or more manual and/or automatic tools for editing the base anatomic model, such as via a graphical user interface and one or more user input devices, such as a mouse, keyboard, touch screen display, and the like. As described herebelow, user "actions" are performed using controls, programs and/or algorithms included in and/or as enabled by system 100. In some embodiments, it can be advantageous to add one or more structures (e.g. "anatomical projections") to the base anatomic model, such as to represent the pulmonary veins and/or at the left atrial appendage. System 100 can enable the user to add "simple" geometric projections (e.g. projections with a base shape, projected along a straight or nearly straight path, with little or no change in the base shape along the projection), and/or more complex geometric projections, such as projections formed by adding "stress" along a user defined vector to deform the base anatomic model, both as defined herebelow.

In some embodiments, the user defines a projection to be added to the base anatomic model by inputting the point of intersection of the projection, the vector (direction and length) of the projection, and the shape of the projection. The point of intersection can be selected by selecting a vertex of the base anatomic model. The user can define the vector of the projection by orienting the base anatomy in a particular position on the screen (e.g. by rotating the model so the desired vector is in the "up" direction, or "into" the screen", etc.), or by "drawing" the desired vector (e.g. by creating a line in 3D space by selecting a first point and a second point), or by any other method of defining a vector. The user can adjust the length and direction of the vector, such as by "dragging" the terminal point of the vector, along the direction of the vector (to change the length of the vector), or freely in space (to change the direction and/or length of the vector). The user can then define the base shape to be projected along the vector, by drawing a shape, highlighting a portion of the base anatomic model, or selecting portions (e.g. one or more vertices and/or polygons) of the base anatomic model. The user can define the base shape using one or more drawing tools provided by system 100, such as to draw a circle, ellipse, or other defined shape, or a free form shape. This drawn shape can be projected along the vector to select the vertices of the anatomic model enclosed within the projection, and those vertices can be projected along the vector to form the final projection to be added to the base model. In some embodiments, the projection follows the user defined shape (e.g. the system does not limit the projection to the enclosed vertices), and the system performs a fitting function (e.g. a fillet) to approximate the transition between the base model and the projection. In some embodiments, the user can define the base of the projection by using a gross selection tool to select (or deselect) vertices of the base model using a "paintbrush-like" function. Additionally or alternatively, the gross selection tool can include a "lasso" type editing function, automatically selecting vertices enclosed within a group of selected vertices. Additionally or alternatively, the user can define the base of the projection by individually selecting vertices and/or polygons of the base anatomic model, such as with a fine selection tool.

In some embodiments, projecting the vertices of the base anatomic model allows the system to process (e.g. refine) the improved anatomic model as a single "mesh" (the set of polygons defining the 3D surface), such that the projections are processed with the remainder base model of the anatomy. Processing can include but is not limited to: smoothing, remeshing, sub-division, hole closing, isolated or floating triangle identification and removal, and the like. Additionally or alternatively, the projections can be processed separately from the remainder of the base model, such that the user defined structures are not modified when processing the improved anatomic model.

In some embodiments, system 100 enables the user to perform one of the following actions: confirm a created projection (e.g. save the projection to the improved model); clear a created projection and/or the anatomical points used to create the projection and create a new projection; define the "behavior" of a projection with respect to the display of electrical activity on the model (e.g. treat the projection as a "hole" in the anatomic model without displaying electrical activity); modify geometric parameters of a projection, such as length, scaling of the cross-section, point of intersection, and/or vector direction of structure; delete previously created structures; erase anatomical points; remove sections of a projection and/or other parts of the anatomic model; modify a region of vertices or polygons by 'pushing or pulling' the elements using a user-input device, such as a mouse; and combinations of one or more of these.

One or more of the steps to create the improved anatomic model can be performed semi-automatically and/or automatically ("automatically" herein). In some embodiments, an automatic modification by system 100 to the base model can be overridden by the user. In some embodiments, one or more of the parameters for defining a projection, such as its direction, shape, size, length, cross-section, location, and/or intersection, can be defined automatically by system 100, based on one or more inputs, such as the first set of anatomic data. In some embodiments, as described hereabove, the user can collect additional data points to update the anatomic model, and system 100 can automatically update the anatomic model, such as by adding a projection to the model. System 100 can update the model based on this additional data a rate of once per 1 millisecond to once per 10 seconds, such as once per 100 ms or 500 ms, based on the incremental acquisition of the data (e.g. based on how quickly data is collected and/or how quickly additional data is determined by system 100 to warrant an update to the model). System 100 can determine if the additional data correlates to a projection based on one or more properties of the data. For example, the additional data alone can comprise a set of data correlating primarily to a segment of the anatomy best modeled as a projection from the base anatomic model, and that data represents a shape (e.g. a shape approximating the anatomy) with one or more principal components.

System 100 can be configured to extract these one or more principal components and determine one or more properties of the projection to be added to the anatomic model. For example, a principal component vector of the data can be used to determine the primary axis of the structure. The point of intersection of the projection can be determined by the intersection of the primary directional vector with the base anatomic model. The shape of the projection can be determined by a cross section, outer boundary, or other measure of the additional data. A cross-section or outer boundary method of determining a parameter of the projection can utilize a plane, normal to the base model at the point of intersection and/or normal to the directional vector of the additional data, for determining the shape of the projection. In some embodiments, these methods can utilize a subset of vertices of the base model within a threshold from the point of intersection to define the projection. In some embodiments, these methods can utilize only a subset of the additional data determined to be "outside" the base model. In some embodiments, the projection can be based on the dot product of the vector between a point in the additional data and the nearest base model vertex, and the normal vector from the base model vertex.

In some embodiments, projections are added by system 100 using a bounding method as described herebelow. A bounding surface is determined using a convex hull that bounds a set of all anatomy data "points" (e.g. from the first set of data and any additional data gathered). A bounding surface is determined using an alpha shape that bounds a set of anatomy points. Internal vertices and triangles are removed from the data, and a subset of the data can be excluded from the projections to be created, such as subset of points determined to be internal to the base anatomy, or a subset of points within a distance from the surface of the base anatomy. A subset of vertices (a "patch") of the base anatomy intersected by the bounding surface is removed from the base anatomy creating a hole and/or a boundary with which to connect the created structure. The boundaries of the hole created on the base anatomy and the edges of the created structure can be blended to produce a "water-tight" boundary (e.g. a seamless boundary). In some embodiments, a new alpha shape can be calculated by system 100 from the improved anatomy, creating a new improved anatomy, filling any potential holes created by the addition of the projection(s). In some embodiments, the automated anatomy can change or update dynamically with the acquisition of additional data and/or the erasure (e.g. by the user) of vertices or data points.

While the foregoing has described what are considered to be the best mode and/or other preferred embodiments, it is understood that various modifications can be made therein and that the invention or inventions may be implemented in various forms and embodiments, and that they may be applied in numerous applications, only some of which have been described herein. It is intended by the following claims to claim that which is literally described and all equivalents thereto, including all modifications and variations that fall within the scope of each claim.

We claim:

1. A cardiac information processing system, comprising:
a catheter including an array of electrodes having a known spatial configuration in three-dimensional space and a plurality of ultrasound transducers configured to record cardiac activity data over multiple cardiac cycles, including electrical activity data and wall position data; and
a cardiac information console, comprising:
a signal processor configured to:
perform an inverse solution using Singular Value Decomposition to calculate sets of cardiac activity data at a plurality of time intervals using the recorded cardiac activity data;
process the electrical activity data to determine discrete time segments representing phases of the multiple cardiac cycles, by determining a time index that is a unique phase of the cardiac cycle and segmenting data between each sequential pair of time indices into a predetermined number of time segments;
segment the wall position data into datasets, wherein each dataset comprises a set of points representing at least a portion of a cardiac surface during one of the discrete time segments;
aggregate the wall position data and segment the aggregated wall position data into multiple bins, each bin including anatomic data from one of the discrete time segments;

when there are more or less discrete time segments than the number of bins, adjust the recorded cardiac activity data to account for the difference;
create an anatomic foundational model from cardiac activity data from a single bin representing a single discrete time segment; and
generate anatomic models representing the remaining bins based on the foundational model using a conformal mesh, wherein the signal processor is configured to project each vertex of the foundational model along its normal axis, inward and outward, and to adjust each vertex along a projection to match at least approximately the cardiac activity data in subsequent bins, thereby creating anatomic models representing the cardiac activity data in each bin based on the foundational model; and
a user interface module configured to display a beating anatomic model of at least one cardiac chamber as a sequence of the generated anatomic models.

2. The system of claim 1, further comprising a three-dimensional array comprising a plurality of biopotential electrodes and a plurality of ultrasound transducers.

3. The system of claim 1, wherein one or more sensors are configured to record cardiac electrical activity data and the wall position data in an interleaved pattern.

4. The system of claim 1, wherein the discrete time segments are a periodic set of time segments.

5. The system of claim 1, wherein the key time index of the unique phase of the cardiac cycle is a rise or fall of a V-wave of the cardiac cycle.

6. The system of claim 2, wherein:
the signal processor is configured to set a total number of the multiple bins equal to an average number of time segments of the recorded multiple cardiac cycles.

7. The system of claim 6, wherein:
if a number of discrete time segments is more than the number of bins, the signal processor is configured to skip additional discrete time segments; and/or
the signal processor is configured to remove the additional discrete time segments from an end of the cardiac cycle; and/or
the signal processor is configured to apply an algorithm to determine the discrete time segments to be skipped and the algorithm applies a pattern that is based on a number of the additional discrete time segments; and/or
the signal processor is configured to assign one or more of the additional discrete time segments to a different bin.

8. The system of claim 6, wherein, if a number of discrete time segments is less than the number of bins, the signal processor is configured to distribute the discrete time segments into a subset of bins.

9. The system of claim 8, wherein:
the signal processor is configured to evenly sample the discrete time segments and evenly distribute the discrete time segments among the subset of bins;
and/or the signal processor is configured to assign the discrete time segments to bins that have similar properties to cardiac activity data in the bin to be assigned.

10. The system of claim 2, wherein the signal processor is configured to, for each bin, use the wall position data contained in the bin to create the anatomic model of the at least one cardiac chamber for the associated discrete time segment of the cardiac cycle represented.

11. The system of claim 2, wherein the signal processor is configured to use one or more smoothing filters to refine the anatomic models created.

12. The system of claim 11, wherein the signal processor is configured to use a low pass filter to adjust a location of each vertex of each anatomic model, based on a distance from a fixed location and/or a coordinate origin to each vertex for each of the anatomic models created.

13. The system of claim 1, wherein the cardiac information console is configured to superimpose the electrical activity data on the beating anatomic model.

14. The system of claim 13, wherein:

the electrical activity data comprises surface charge data and/or dipole density data; and/or the cardiac information console is configured to determine one or more metrics relating to the electrical activity data superimposed on the beating anatomic model, including one or more of a size, a shape, and/or a motion of the at least one cardiac chamber; and/or the cardiac information console is configured to measure and/or display one or more of: ejection fraction, stroke volume, chamber volume, chamber dimensions, regional wall displacement, and/or velocity; and/or the cardiac information console is configured to calculate and display atrial and/or other chamber volume as a function of time.

15. The system of claim 13, wherein the cardiac information console is configured to display functional charac-teristics, including one or more of displacement and/or velocity of a cardiac wall at each vertex as a color map depicting a representation of contractility.

16. The system of claim 15, wherein the cardiac infor-mation console is configured to display a difference and/or change in displacement and/or velocity of the cardiac wall before and after an event as a changed color map depicting regions of altered functional characteristics arising from the event.

17. The system of claim 13, wherein the cardiac infor-mation console is configured to measure and/or display one or more surface dynamics, including one or more of a tissue stress or strain, a blood velocity, and/or a regional wall contractility.

18. The system of claim 1, wherein the cardiac informa-tion console is configured to detect an undesirable condition selected from a group consisting of: tamponade; stroke; a deviation from a stable hemodynamic condition; decrease in ejection fraction; decrease in stroke volume; decrease in wall motion; undesirable decrease in chamber volume; undesirable increase in chamber volume; and combinations thereof.

\* \* \* \* \*